(12) United States Patent
Eggers et al.

(10) Patent No.: US 6,219,567 B1
(45) Date of Patent: Apr. 17, 2001

(54) MONITORING OF TOTAL AMMONIACAL CONCENTRATION IN BLOOD

(75) Inventors: Philip E. Eggers, Dublin; Andrew R. Eggers, Ostrander; Eric A. Eggers, Columbus, all of OH (US); Scott P. Huntley, Danville, CA (US)

(73) Assignee: Cardiox Corporation, Menlo Park, CA (US)

( * ) Notice: Subject to any disclaimer, the term of this patent is extended or adjusted under 35 U.S.C. 154(b) by 0 days.

(21) Appl. No.: 09/337,382

(22) Filed: Jun. 21, 1999

(51) Int. Cl.$^7$ .................................................... A61B 5/00
(52) U.S. Cl. ........................ 600/322; 600/341; 600/348; 600/364
(58) Field of Search .................................. 600/309, 310, 600/311, 312, 317, 322, 329, 341, 345, 347, 348, 364, 353

(56) References Cited

U.S. PATENT DOCUMENTS

| | | | |
|---|---|---|---|
| 4,703,756 | * 11/1987 | Gough et al. | 600/347 |
| 4,834,101 | * 5/1989 | Collison et al. | 600/353 |
| 5,434,084 | * 7/1995 | Burgess, Jr. | 600/329 |
| 5,453,248 | 9/1995 | Olstein . | |
| 5,536,783 | 7/1996 | Olstein et al. . | |
| 5,607,644 | 3/1997 | Olstein et al. . | |

OTHER PUBLICATIONS

Assadi, A. "Interaction of Planar Polymer Schottky Barrier Diodes with Gaseous Substances." *Sensors and Actuators B*, 1994; 20: 71–77.

Bachman C. "Diagnosis of Urea of Cycle Disorders." *Enzyme* 1987; 38: 233–241.

Banister EW. Cameron BJC. "Exercise–Induced Hyperammonemia: Peripheral and Central Effects." *International Journal of Sports Medicine* 1990; 11: S 129–S 142.

Batshaw ML, Brusilow SW. "Valproate–Induced Hyperammonemia." *Annals of Neurology* 1982; 11: 319–321.

Batshaw ML. "Hyperammonemia." *Current Problems in Pediatrics* 1984; 14 (11): 1–69.

Batshaw ML, Monahan PS. "Treatment of Urea Cycle Disorders." *Enzyme* 1987; 38: 242–250.

Batshaw ML. "Inborn Errors of Urea Synthesis." *Annals of Neurology* 1994; 35: 133–141.

Bessman AN, Evans JM. "The Blood Ammonia in Congestive Heart Failure." *American Heart Journal* 1955; 715–719.

Breningstall, GN. "Neurologic Syndromes in Hyperammonemic Disorders." *Pediatric Neurology* 1986; 2: 253–62.

Brockmoller J, Roots I. "Assessment of Liver Metabolic Function." *Clinical Pharmacokinetic Concepts* 1994; 27 (3): 216–248.

(List continued on next page.)

*Primary Examiner*—Eric F. Winakur
(74) *Attorney, Agent, or Firm*—Mueller and Smith, L.P.A.

(57) ABSTRACT

Total ammoniacal concentration (TAC) in blood is measured and displayed on a repetitive basis by a controller driven sensor arrangement which may be utilized either with a catheter structure or with a bypass system. The catheter based sensors may be employed with a peripheral region of the vascular system of the body. Repetitive measurements are carried out and these measurements are subjected to a moving average filtering procedure, whereupon the filtered TAC values are displayed numerically and graphically. The controller functions to compute the rate-of-rise of TAC and compares that value with a threshold rate-of-rise valuation which is inputted by the practitioner. Threshold values for TAC also may be inputted and the system not only provides alarm warnings for threshold excursions in TAC above threshold or excursions in rate-of-rise of TAC above threshold but also provides a visual cuing as a warning that TAC is elevating from one filtered measurement to the next.

164 Claims, 26 Drawing Sheets

OTHER PUBLICATIONS

Brusilow SW, Batshaw ML, Waber L. "Neonatal Hyperammonemic Coma" *Advances in Pediatrics* 1982; 29: 69–103.

Brusilow, SW, Danney, M, Waber, LJ, et al. "Treatment of Episodic Hyperammonemia in Children with Inborn Errors of Urea Synthesis." *The New England Journal of Medicine* 1984; 310: 1630–1634.

Burtis CA, Ashwood ER (eds.). Teitz *Textbook of Clinical Chemistry* (second edition). Philadelphia: W.B. Saunders Company, 1994, pp. 1487–1489.

Burton, BK. Abstract of "Inborn Errors of Metabolism in Infancy: A Guide to Diagnosis." *Pediatrics* 1998; 102(6).

Canzanello VJ, Rasmussen RT, McGoldrick MD. "Hyperammonemic Encephalopathy During Hemodialysis." *Annals of Internal Medicine* 1983; 99 (2): 190–191.

Cha, GS, Liu, D, Meyerhoff, ME, et al. "Electrochemical Performance, Biocompatibility, and Adhesion of New Polymer Matrices for Solid–State Ion Sensor." *Analytical Chemistry* 1991; 63(17): 1666–1672.

Chaves–Carbollo, E. "Detection of Inherited Neurometabolic Disorders." *Pediatric Neurology* 1992; 39 (4): 801–820.

Ciana, LD, Caputo, G. "Robust, reliable biosensor for continuous monitoring of urea during dialysis." *Clinical Chemistry* 1996; 47 (7): 1079–1085.

Clark, LC, Lyons, C. "Electrode Systems for Continuous Monitoring in Cardiovascular Surgery." Annals New York Academy of Sciences. pp. 29–45.

Cunningham, FG, McDonald, PC, Gant, NF, Williams *Obstetrics*. Appleton & Lange Norwalk: 1989.

Diamond DA, Blight A, Ransley PG. "Hyperammonemic Encephalopathy: A Complication Associated with the Prune Belly Syndrome." *Journal of Urology* 1989; 142: 361–362.

Duarte J, Macias S, Coria F, Fernandez E, Claveria LE. "Valproate–Induced Coma: Case Report and Literature Review." *Annals of Pharmacotherapy* 1993; 27: 582–583.

Evans, J, et al. "Altered Liver Function of Chronic Congestion Heart Failure." *American Journal of Medicine* 1952; 13: 704–712.

Ferenci, P, Herneth, A, Steindl, P. "Newer Approaches to Therapy of Hepatic Encephalopathy." *Seminars in Liver Disease*. 1996; 16 (3): 329–338.

Fonseca–Wollheim F. "The influence of pH and various anions on the distribution of NH4+ in human blood." *European Journal of Clinical Chemistry and Clinical Biochemistry* 1995; 33 (5): 289–294.

Fricker R, Doptis P, Hornak M, Li C. "Development of an optimized ammonia assay for the Kodak Ektachem Analyzer." *Clinical Chemistry* 1990; 36 (6): 1072.

Furst, P, Josephson, B, et al. "Nitrogen Balance after Intravenous and Oral Administration of Ammonium Salts to Man." *J. Appl. Physiol.* 1969; 26(1): 13–22.

Gowenlock AH, McMurray JR, McLauchlan DM (eds). *Varley's Practical Clinical Biochemistry* (sixth edition). Boca Raton: CRC Press, Inc., 1988. pp. 742–749.

Green A. "When and how should we measure plasma ammonia?" *Clinical Biochemistry* 1988; 25: 199–209.

Hindfelt, B. "The Distribution of Ammonia between Extracellular and Intracellular Compartments of the Rat Brain." *Clinical Science and Molecular Medicine* 1975; 48: 33–37.

Hsia YE. "Inherited Hyperammonemic Syndromes." *Gastroenterology* 1974; 67: 347–374.

Huizenga JR, Tangerman A, Gips CH. "A Rapid Method for Blood Ammonia Determination Using the New Blood Ammonia Checker (BAC) II." *Clinica Chimica Acta* 1992; 210: 153–155.

Imler M, Frick A, Schliener JL, Stahl A. "An Automated Microassay for Blood Ammonia." *Journal Clinical Chemistry and Clinical Biochemistry* 1979; 17: 247–250.

Losefoshn M, Hicks JM. "Ektachem Multilayer Dry–Film Assay for Ammonia Evaluated." *Clinical Chemistry* 1985; 31 (12): 2012–2014.

Jacquez, JA, Poppell, JW, Jeltsch, R. "Solubility of ammonia in human plasma." *Journal of Applied Physiology.* 1959; 14(2): 255–258.

Jurgens, P. "New Aspects on Etiology, Biochemistry and Therapy of Portal Systemic Encephalopathy: A critical Survey." *Nutrition* 1997; 13: 560–570.

Kasal C. "Agent Ammonia: A New Total Liquid Assay System for Blood Ammonia Levels for the Abbott Spectrum." *Clinical Chemistry* 1988; 34 (6): 1188–1189.

Kotin P, et al. "Cardiac or congestive cirrhosis of the liver." *American Journal of Pathology* 195 1; 27: 561–570.

Kubasik NP, Lisuzzo CW, Same DG, et al. "Multilayered film analysis: Evaluation of ammonia and creatinine slides." *Chemical Biochemistry* 1984; 17: 15–18.

Lahdesmaki, I, Lewenstam, A., Ivaska, A. "A polyprrole-–based Amperometric Ammonia Sensor." *Talanta* 1996; 43: 125–134.

Lamiell JJ, Ducey JP, Freesekepczyk BJ, Musio FO, Hansberry KL. "Essential amino acidinduced adult hyperammonemic encephalopathy and hypophosphatemia." *Critical Care Medicine* 1990; 18 (4): 451–452.

Leonard JV. "Hyperammonemia in childhood." In: Clayton BE, ed. *Chemical Pathology and the Sick Child.* Oxford: Blackwell, 1984: 96–119.

Leevy, CM, Leevy, CB, Howard, MM. "Indocyanine Green and the Liver." *Problems in Liver Diseases*. Stratton Intercontinental Medical Book Corporation. New York: 1977.

Lockwood, AH, McDonald, JM, etal. "The Dynamics of Ammonia Metabolism in Man." *Clin. Invest.* 1979; 63:449–460.

Martin, WJ, Matzke, GR. "Treating Severe Metabolic Alkalosis." *Clinical Pharmacology* 1982; 1: 42–48.

Msall M, Batshaw ML, Suss R, Brusilow SW, Mellits ED. "Neurologic Outcome in Children with Inborn Errors of Urea Synthesis: Outcome of Urea–Cycle Enzymopathies." *New England Journal of Medicine* 1984; 310: 1500–1505.

Nelson, RM, Seligson, D. "Studies on Blood Ammonia in Normal and Shock States." *Surgery.* 1953; 34(1): 1–8.

Oster J, et al. "Exacerbation of Hepatic Encephalopathy by Chronic Renal Failure." *Clinical Nephrology* 1978; 9: 254–257.

Ozand PT, Gascon GG. "Organic Acidurias: A Review Part 2." *Journal of Child Neurology* 1991; 6: 288–303.

Queres, JC. "Hyperammonemia and Helicobacter pylori." *The Lancet* 1995; 346:713.

Quiles R, Fernandez–Romero JM, Fernandez E, De Castro MDL. "Continuous flow assay of ammonia in plasma using immobilized enzymes." *Analytica Chimica Acta* 1994; 294 (1): 43–47.

Ratnaike RN, Buttery JE, Hoffman S. "Blood Ammonia Measurement Using a Simple Reflectometer." *Journal of Clinical Chemistry and Clinical Biochemistry* 1984; 22 (1): 105–108.

Russell, A. The Implications of Hyperammonemia in Rare and Common Diseases, Including Migraine.

Ryder KW, Olson JF, Kahnoski S. "Hyperammonemia After Transurethral Resection of the Prostate: A Report of 2 Cases." *Journal of Urology* 1984; 132: 995–997.

Tanner, RL. "Ammonia Metabolism." *American Journal of Physiology* 1978; 235(4) F265–F277.

Thomas DW, Sinatra FR, Hack SL, Smith TM, Platzker ZCG, Merritt RJ. "Hyperammonemia in Neonates Receiving Intravenous Nutrition." *Journal of Parenteral and Enteral Nutrition* 1982; 6 (6): 503–506.

Van Thiel, DH. "Assessment of Liver Function: The Current Situation" *J. Okla. State Med. Assoc.* 1995; 88: 11–16.

Vellekoop, MJ, Lubking, GW, et al. "Integrated–circuit–compatible Design and Technology of Acoustic–wave–based Microsensors." *Sensors and Actuators A* 1994; 44: 249–263.

Walser M, Stewart PM. "Organic Acidaemia and Hyperammonemia: Review." *Journal of Inherited and Metabolic Disease* 198 1; 4 (4): 177–182.

Wilkerson, JE, Batterton, DL, Horvath, SM. "Exercise–Induced Changes in Blood Ammonia Levels in Humans." *European Journal of Applied Physiology.* 1977; 37: 255–263.

Wilson, BE, et al. "Rapidly Fatal Hyperammonemic Coma in Adults—Urea cycle enzyme deficiency." *West J. Med.* 1994; 161: 166–168.

Yang, VC, Ma, S, et al. "A Novel Electrochemical Heparin Sensor." *ASAIO Journal* 1993; 39: M195–M201.

Yoshida EM, Ostrow DN, Erb SR, Fradet G. "Hyperammonemia After Heart–Lung Transplantation." *Gastroenterology* 1997; 112 (6): 2162.

Zhang, SF. "Evaluation of fluorescent dyes for in vitro pH measurement." *Med. & Biol., Eng. & Comput.* 1994, 32: 224–227.

\* cited by examiner

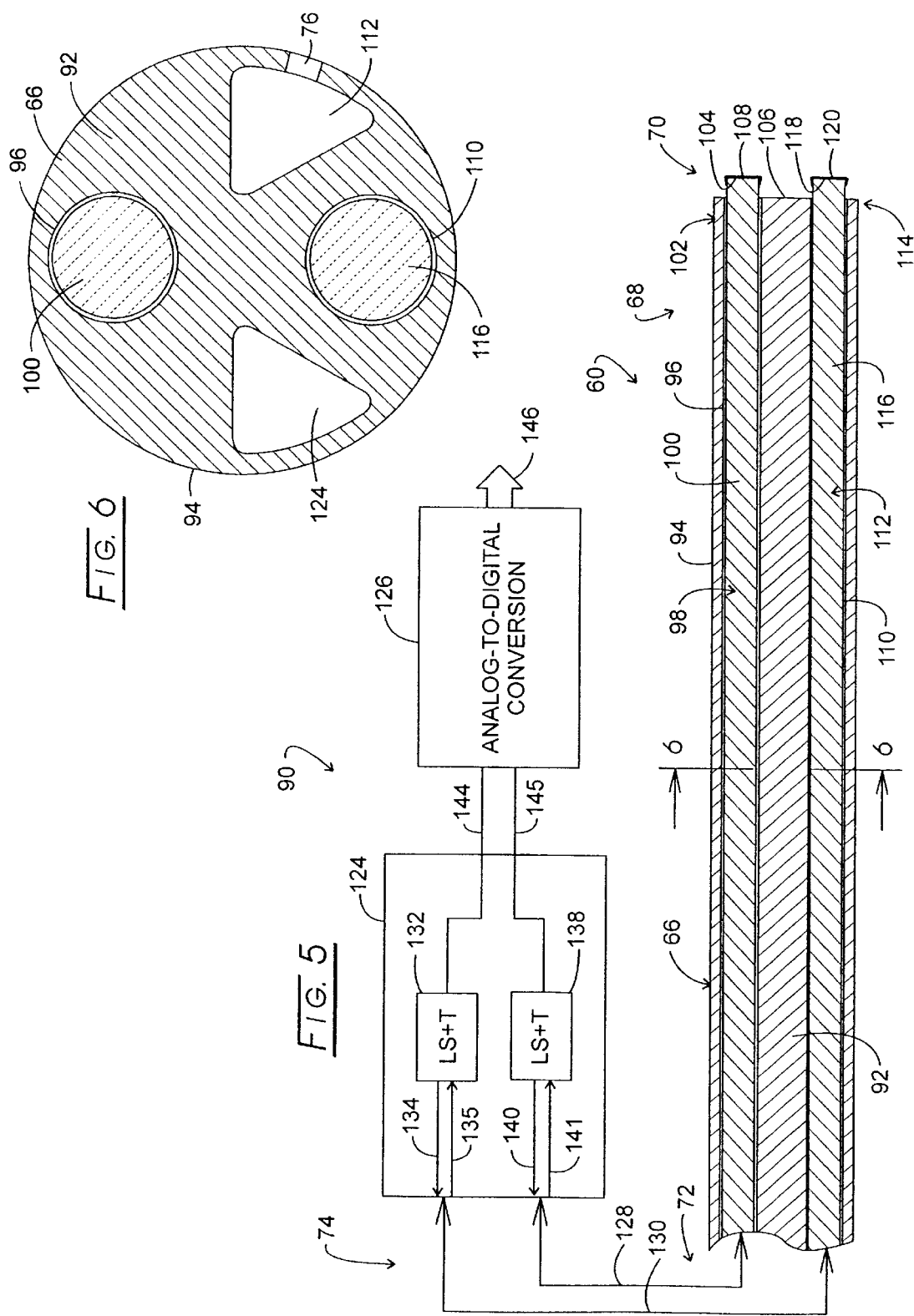

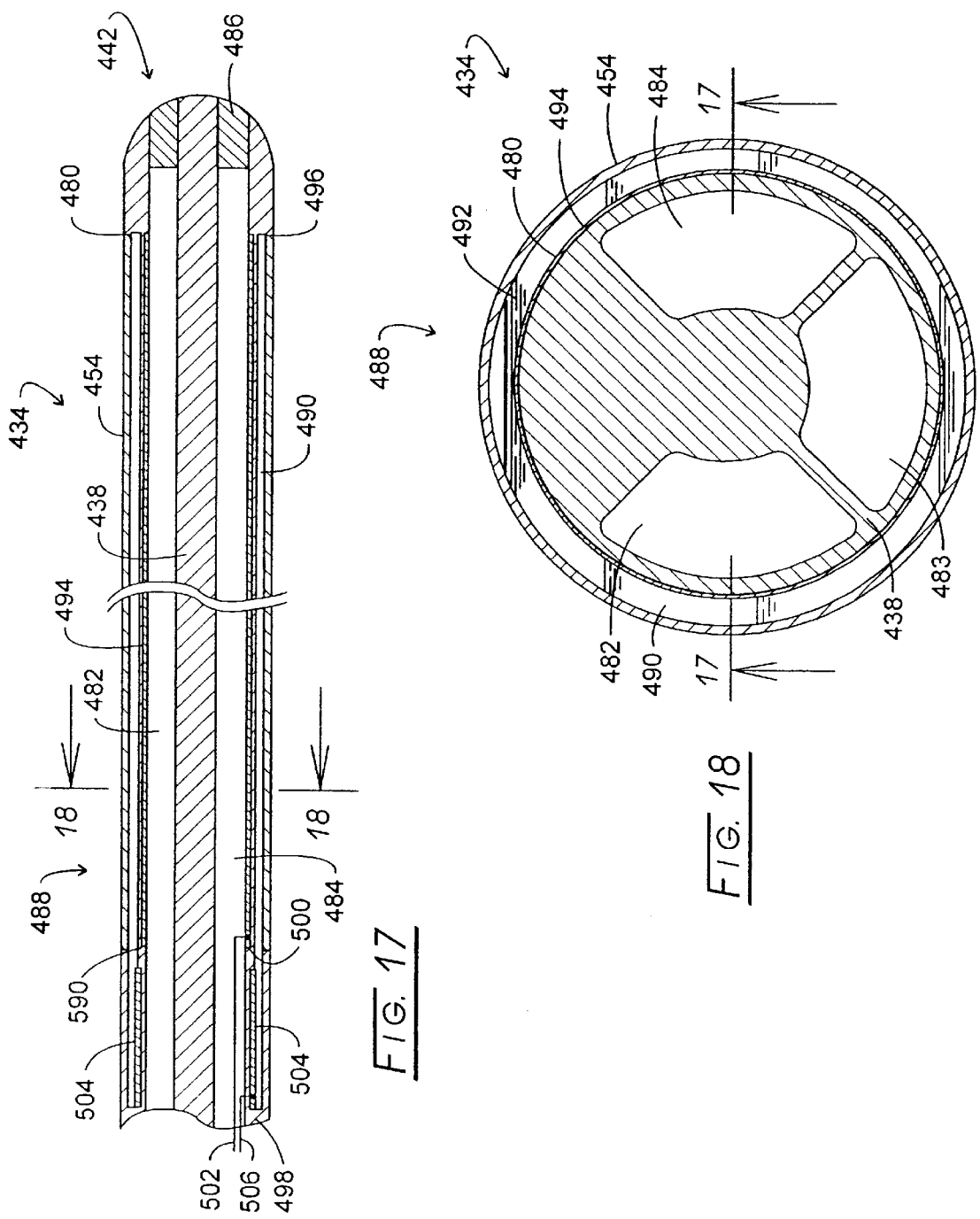

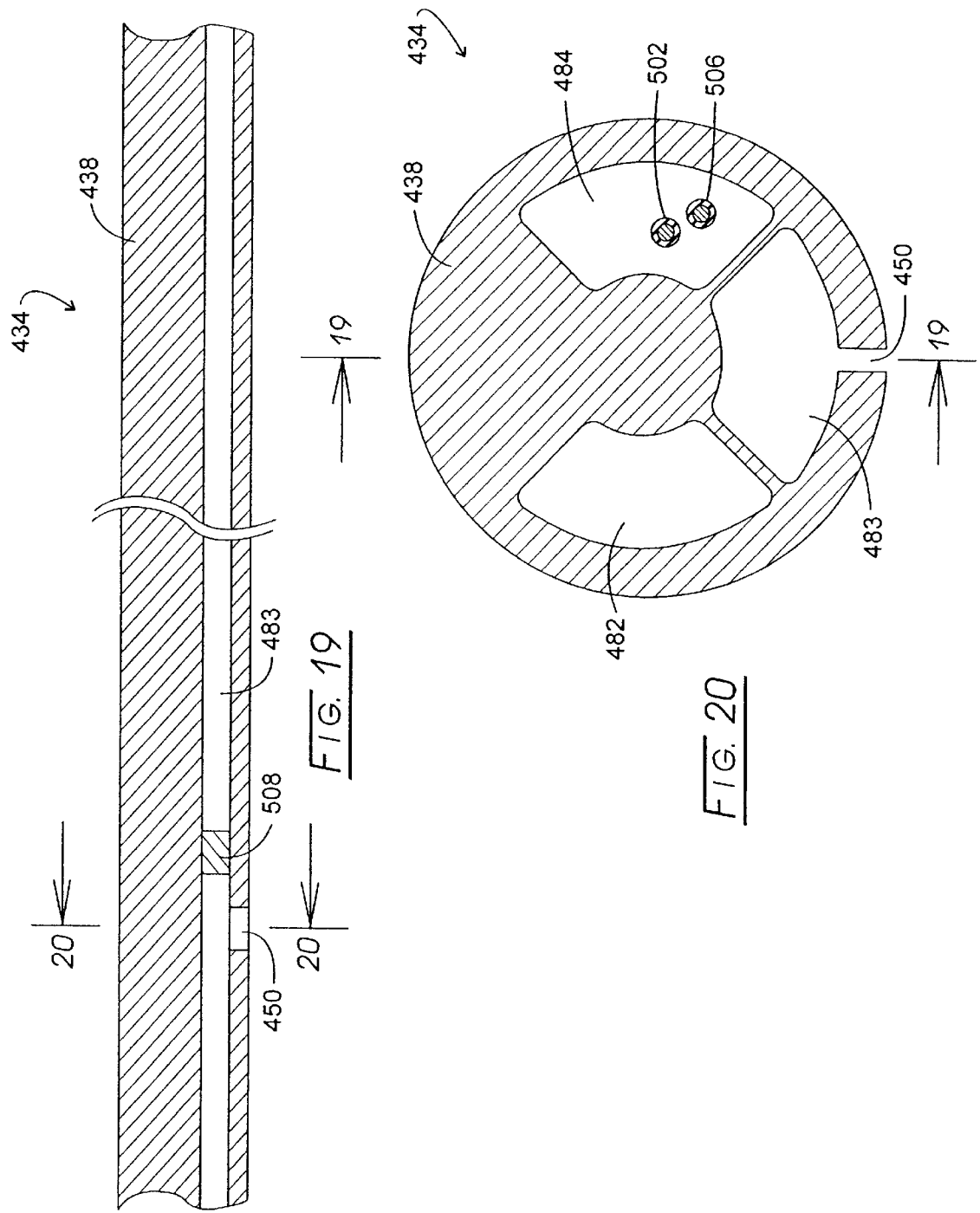

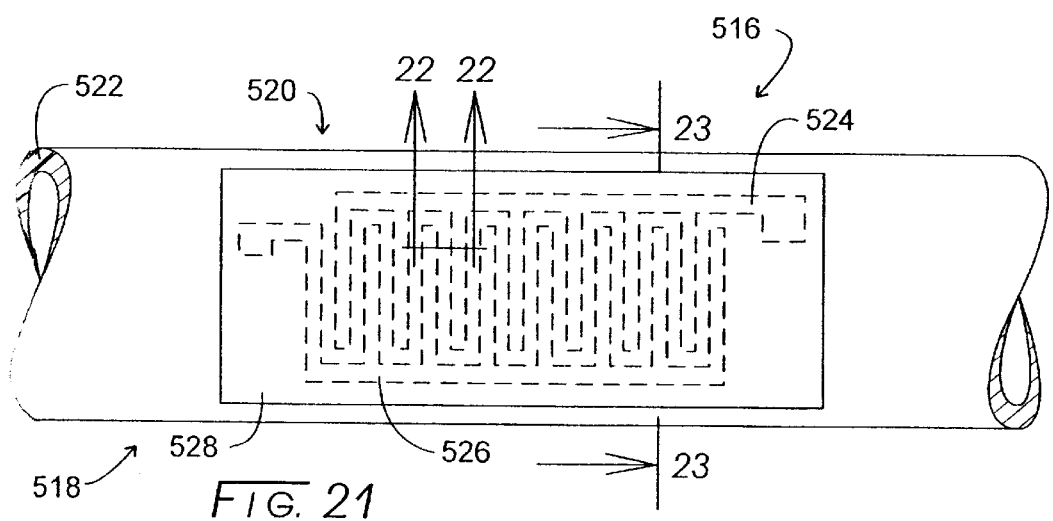
FIG. 21
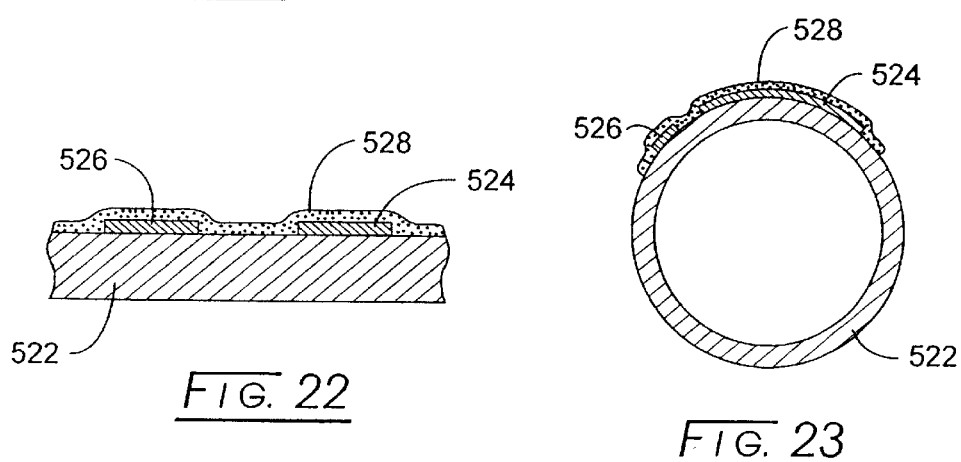
FIG. 22
FIG. 23
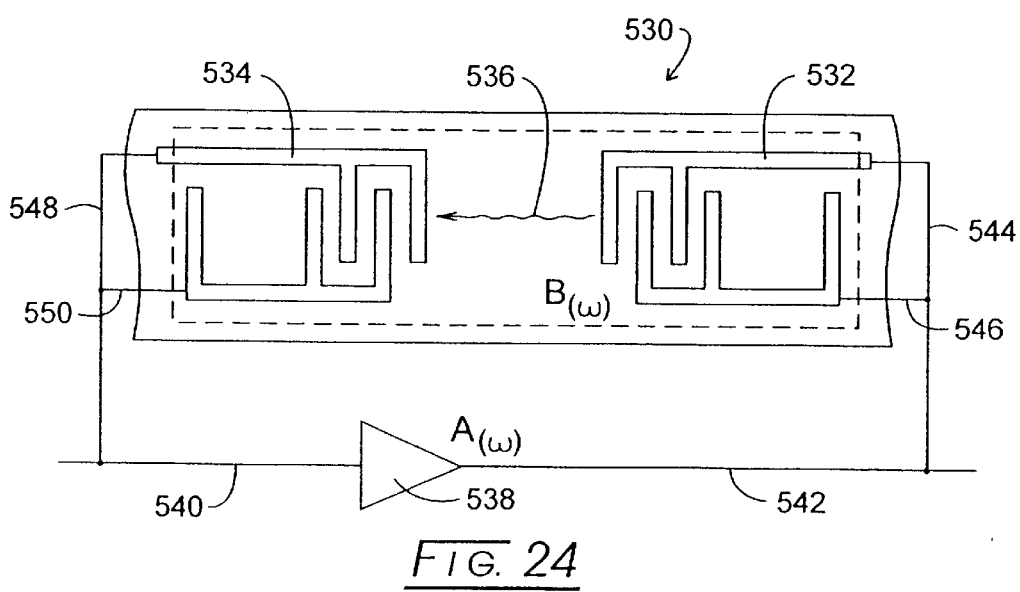
FIG. 24

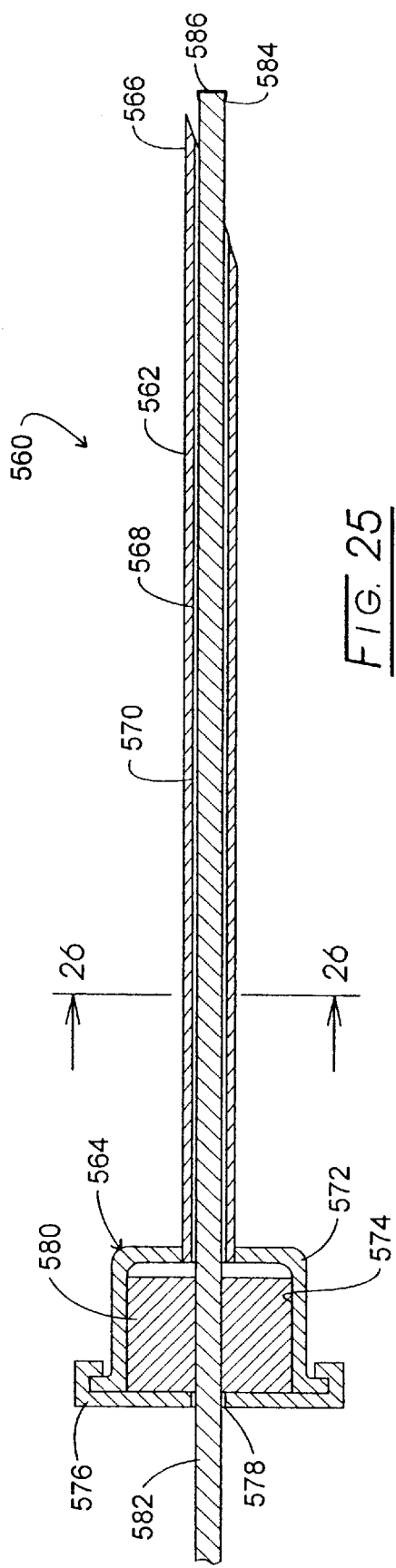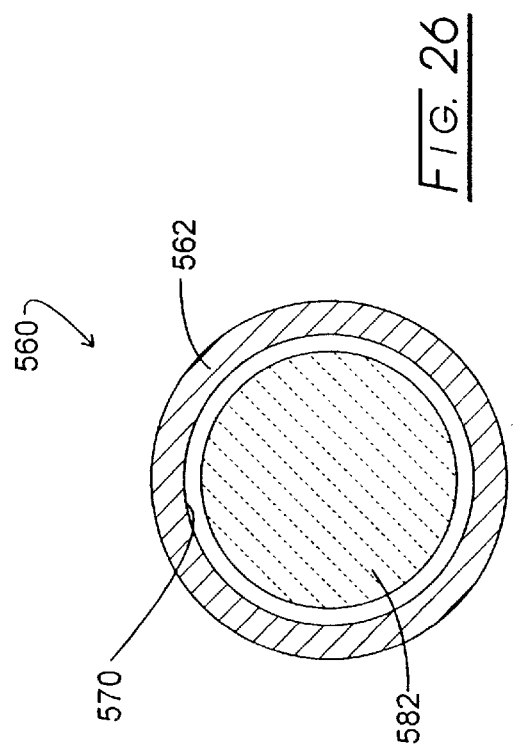

MONITORING OF TOTAL AMMONIACAL CONCENTRATION IN BLOOD

CROSS-REFERENCE TO RELATED APPLICATIONS

STATEMENT REGARDING FEDERALLY SPONSORED RESEARCH

Not applicable.

BACKGROUND OF THE INVENTION

Ammoniacal levels (often referred to as "ammonia") are found normally in the body and ordinarily are not harmful, yet in increased concentration become toxic. Hyperammonemia is the clinical condition associated with increased plasma ammoniac levels which manifests itself in vomiting, lethargy, confusion, and coma. Prognosis for patients suffering from hyperammonemia depends on prompt detection and aggressive treatment. Once it has been recognized that a patient is suffering from hyperammonemia, there are alternatives available for lowering the level of ammoniac component present in the blood. If undetected or untreated, however, continuing hyperammonemia may result in severe brain damage or death.

Hyperammonemia is not a diagnosis, rather it is a condition which may result from one of any number of underlying causes which range from inherited abnormalities, to acquired diseases, to inducement during the course of treatment for other illnesses. The normal ammoniacal concentration ranges from 15 to 35 $\mu$mol/liter in adults and 20 to 50 $\mu$mol/liter in children. A patient may experience a symptomatic range including vomiting, loss of muscle coordination, irritability and hyperactivity at 100 or above $\mu$mol/liter, vomiting and lethargy at 200 $\mu$mol/liter, and coma at or above 300 $\mu$mol/liter. While these ammoniacal concentration levels may seem high, being double to six times the normal levels in a healthy adult, ammoniacal concentration levels for inherited disorders have been reported being over 1000 $\mu$mol/liter to as much as 4000 $\mu$mol/liter.

The highest levels of ammoniacal concentration are reported in cases of transient hyperammonemia where concentration may rise to 2000 to 4000 $\mu$mol/liter, nearly 100 times greater than normal. This occurs with one type of transient hyperammonemia whose cause, while still uncertain, has been linked to transient abnormalities of the urea cycle, delayed development of an affecting enzyme outside the urea cycle, tissue hypoxia or poor perfusion through the liver. Another type of transient hyperammonemia involves ammoniacal concentration levels which are approximately twice the normal level, but which generally decreases to normal without treatment.

Inherited disorders of the urea cycle also may cause hyperammonemia in both adults and children, although the most severely affected are present in the neonatal period. If there is a deficiency in one of the urea cycle enzymes, inadequate urea will be formed and nitrogen, in the form of an ammoniacal concentration, will accumulate in all cells of the body. Congenital deficiencies of each of the five enzymes in the urea cycle have been identified. In children, high levels of ammoniac concentration often will manifest itself as a catastrophic illness known as hyperammonemic coma. Morbidity has been associated with the duration of hyperammonemic coma rather than with the specific enzyme deficiency causing the level of ammoniacal concentration elevation.

Another inherited disorder associated with hyperammonemia is organic acidemias, which is a defect in the metabolism of amino acids and fatty acids. A metabolic crisis may be precipitated by excessive protein intake, intercurrent infections, incorrect diet or incorrect medications. For more information on hyperammonemia caused by inherited disorders, see:

1. Ballard, R. A., et al. "Transient Hyperammonemia of the Preterm Infant." New England Journal of Medicine. 1978; 299: 920–925.
2. Batshaw, M. L., et al. "Treatment of urea Cycle Disorders." Enzyme. 1987; 38: 242–250.
3. Leonard, J. V. "Hyperammonemia in Childhood." Clayton, B. E., ed. Chemical Pathology and the Sick Child Oxford: Blackwell, 1984: 96–119.

In addition to inherent abnormalities, hyperammonemia may be caused by acquired diseases or conditions. The leading cause of hyperammonemia in adults is intrinsic liver disease. Acute liver disease being caused by viral hepatitis, drug overdose, reaction to anesthetic agents or medications, and obstruction of bile duct, while the most common causes of chronic liver disease in adults include cirrhosis, infection, excessive protein intake, diuresis, and sedative drugs. Renal failure can precipitate or exacerbate hepatic encephalopathy by excessive production of ammonia. Other diseases or conditions, such as leukemia, urinary tract infections, congestive heart failure, physical trauma to the liver or kidneys, or disseminated herpes simplex infection also may cause hyperammonemia.

A final category of causes for hyperammonemia is inducement during treatment for other illnesses. Sodium valproate is an anti-epileptic agent used to control generalized seizures and other refractory types of seizures which has been reported to cause high levels of ammoniacal concentration in the blood. Hemodialysis may lower ammoniacal concentration levels in patients with hepatic encephalopathy, however, the opposite may be found during hemodialysis with sorbent-based low-volume dialysate regeneration systems. With these systems, urea is converted to ammoniacal components which then are absorbed by a cationic exchange resin. If the absorption rate of the resin is exceeded, these components continue to be converted but diffuses from the dialysate into the patient. Hyperammonemia is also a risk during transurethral resection of the prostate using glycine irrigant due to the metabolic decomposition of glycine into ammoniacal components. Heart and lung transplantation may be accompanied by hyperammonemia, which if not promptly and aggressively treated, can be a life threatening complication.

While the foregoing is not an exhaustive list of potential causes of hyperammonemia, these examples illustrate the wide variety of sources of increased ammoniacal concentration levels and the seriousness of the resulting condition. Fortunately, once a hyperammonemic episode has been identified, a number of intervention alternatives are available to lower ammonia levels. For example, in urea cycle disorders these include limiting nitrogen intake, improving the quality of protein ingested, supplying deficient metabolites, providing alternate pathways for waste nitrogen excretion and removal of nitrogen, i.e., by peritoneal dialysis or hemodialysis. Cases of acute hyperammonemia may require mannitol infusions to control intracranial pressure. With ammoniacal concentration levels decreased to within acceptable bounds, the underlying cause may be addressed.

Several conventional methods currently are available to measure the ammoniacal concentration level present in a patient. Most of these require some form of separation process before analysis. Ammonia gas and ammonium ion are separated from their matrix either by absorption onto a resin or by conversion to ammonia using alkali followed by gaseous diffusion. The ammonia gas concentration may then be quantified colorimetrically or by an ion-specific electrode. Alternatively, enzymatic methods are available which involve the formation of reaction product, proportional to the presence of ammonium ion, which is measured spectrophotometrically or fluorimetrically. While these methods may measure ammoniacal concentration levels with a certain degree of accuracy if performed properly, there are several documented sources of error which may affect the accuracy of the ammonia measurement. One source of error with existing enzyme techniques is that ammonia, as a combination of the gaseous and ionic state, is generated by the deamination of endogenous amino acids in the sample as soon as the blood is withdrawn. Delays greater than 15 minutes before centrifuging of the sample have been reported as causing a clinically significant increase in measured ammoniacal concentrations. Other sources of error include variations in test strip or reagent consistency used to indicate analyte, inconsistencies in indicator sensing means, variations in homogeneity of ammonia distribution in the blood sample, and variation due to the background levels of ammonia gas in the laboratory environment at the time of actual specimen assay. For discussion of current ammoniacal concentration measurement techniques and devices, see:

4. Burtis, C. A. and E. R. Ashwood, eds. *Teitz Textbook of Clinical Chemistry* (second edition). Philadelphia: W. B. Saunders Company, 1994. pp. 1487–1489.

5. Iosefoshn, M. "Ektachem Multilayer Dry-Film Assay for Ammonia Evaluation." Clinical Chemistry. 1985; 31 (12): 2012–2014.

6. Quiles, R., et al. "Continuous flow assay of Ammonia in Plasma Using Immobilized Enzymes." Analytica Chimica Acta 1994; 294 (1): 43–47.

Even assuming an accurate measurement, the time and expense associated with these types of analysis limit their repeatability during a given time period. The assay process can take 30 minutes or more once the sample is introduced into the analyzer. The expense involved with each blood sample includes the cost for the ammoniacal concentration assay as well as hospital staff time and expenses associated with withdrawing a blood sample, centrifuging the blood sample in a refrigerated centrifuge, and transporting the blood sample to the hospital's laboratory for assay. Given that these procedures are relatively expensive and labor intensive, blood ammoniacal concentration measurements are necessarily performed on an infrequent basis, typically several times per day. As such, trending, which would indicate the necessity for intervention where a patient's ammoniacal concentration level begins to rise but before a dangerous condition is reached, is not possible.

In view of the problems associated with existing blood ammoniacal concentration measurement techniques, a need exists for an approach which is more accurate, less expensive, and less time-consuming. Such an approach could consequently be performed more frequently allowing the practitioner to monitor trends in a patient's ammoniacal level and to provide more timely diagnosis and treatment.

BRIEF SUMMARY OF THE INVENTION

The present invention is addressed to a system and method for monitoring total ammoniacal concentration (TAC) in blood. Utilizing either catheter borne or bypass containing sensors, the system employs a controller to obtain TAC values at highly desired relatively short measurement frequency intervals. In general, the sensors of the system are configured and controlled to measure the value of a select ammoniacal component, either ammonia gas ($NH_3$) or the ammonium ion ($NH_4^+$). A preferred sensor structure employs fiberoptic technology to repeatedly measure ammonia concentration. Utilizing the measured pH level in the blood, those ammonia component concentration values then are converted to TAC using the Henderson-Hasselbalch relationship. The value of blood pH may be acquired separately or may be monitored simultaneously with the monitoring of the ammonia component, using for example, fiberoptic technology in conjunction with the sensing function.

The relatively higher TAC measurement frequency permits the use of moving average filtering employing a predetermined number, n, of measurement values in a first in-last out queue of values which is averaged. These filtered TAC values are associated with the real time occurrence of each of the noted first measurements and are submitted to memory as well as to a display function. The processor driven controller further provides a graphics developed trend readout, plotting TAC with real time of measurement. Responding to input supplied by the practitioner, the controller provides an alarm output when measured total ammoniacal concentration equals or exceeds a designated threshold. This controller function further performs rate-of-rise of TAC values and will respond to a practitioner input threshold for such rate-of-rise values to provide an alarm. Also, the processing function of the controller will provide a warning output as a visual cue indicating the occurrence of a rising TAC level from one measurement to a next.

A further feature of the invention is to provide a method for monitoring the ammoniacal concentration in blood within the vascular system contained bloodstream of the body, such system directing blood exhibiting a given pH value along given path directions and extending to peripheral regions of such body without the immediate region of the heart, comprising the steps of:

(a) providing a catheter assembly having a proximal end region, a measurement region spaced therefrom extending to a tip, having a first sensor channel extending from the proximal region to the measurement region, an ammoniacal component sensor supported by the first sensor channel, having an ammoniacal component responsive forward assembly at the measurement region contactable with flowing blood within the bloodstream, the sensor assembly being controllable to provide ammoniacal sensor outputs at the proximal end region;

(b) providing a controller actuable to control the ammoniacal component sensor assembly to derive the ammoniacal sensor outputs over a sequence of measurement intervals, and responsive to the ammoniacal sensor outputs to derive a sequence of total ammoniacal concentration values over a measurement period and deriving display signals corresponding with that sequence of values;

(c) providing a display assembly responsive to the display signals to derive a visibly perceptible information output corresponding therewith;

(d) positioning the catheter assembly measurement region within the bloodstream and preferably at one of the peripheral regions however, the catheter may be of a variety having components located within the heart; and (e) actuating the controller to derive the display signals and effect derivation of the perceptible information output.

Other objects of the invention will, in part, be obvious and will, in part, appear hereinafter. The invention, accordingly, comprises the system and method possessing the construction, combination of elements, arrangement of parts and steps which are exemplified in the following detail description.

For a fuller understanding of the nature and objects of the invention, reference should be made to the following detailed* description taken in connection with the accompanying drawings.

BRIEF DESCRIPTION OF THE DRAWINGS

FIG. 5 is a partial sectional view of the forward end region of the catheter of FIG. 4;

FIG. 6 is a sectional view taken through the plane 6—6 in FIG. 5;

FIG. 17 is a partial sectional view of the catheter of FIG. 16 taken through the plane 17—17 in FIG. 18;

FIG. 18 is a sectional view taken through the plane 18—18 in FIG. 17;

FIG. 19 is a partial sectional view of a catheter taken through the plane 19—19 shown in FIG. 20;

FIG. 20 is a sectional view taken through the plane 20–20 shown in FIG. 19;

FIG. 21 is a schematic diagram of a Schottky diode-based ammoniacal component concentration sensor;

FIG. 22 is a sectional view taken through the plane 22—22 shown in FIG. 21;

FIG. 23 is a sectional view taken through the plane 23—23 shown in FIG. 21;

FIG. 24 is a schematic representation of an acoustic wave-based ammoniacal concentration sensor;

FIG. 25 is a sectional view of a catheter of minimal dimension employed with the system and method of the invention;

FIG. 26 is sectional view taken through the plane 26—26 shown in FIG. 25;

DETAILED DESCRIPTION OF THE INVENTION

Figure 1:
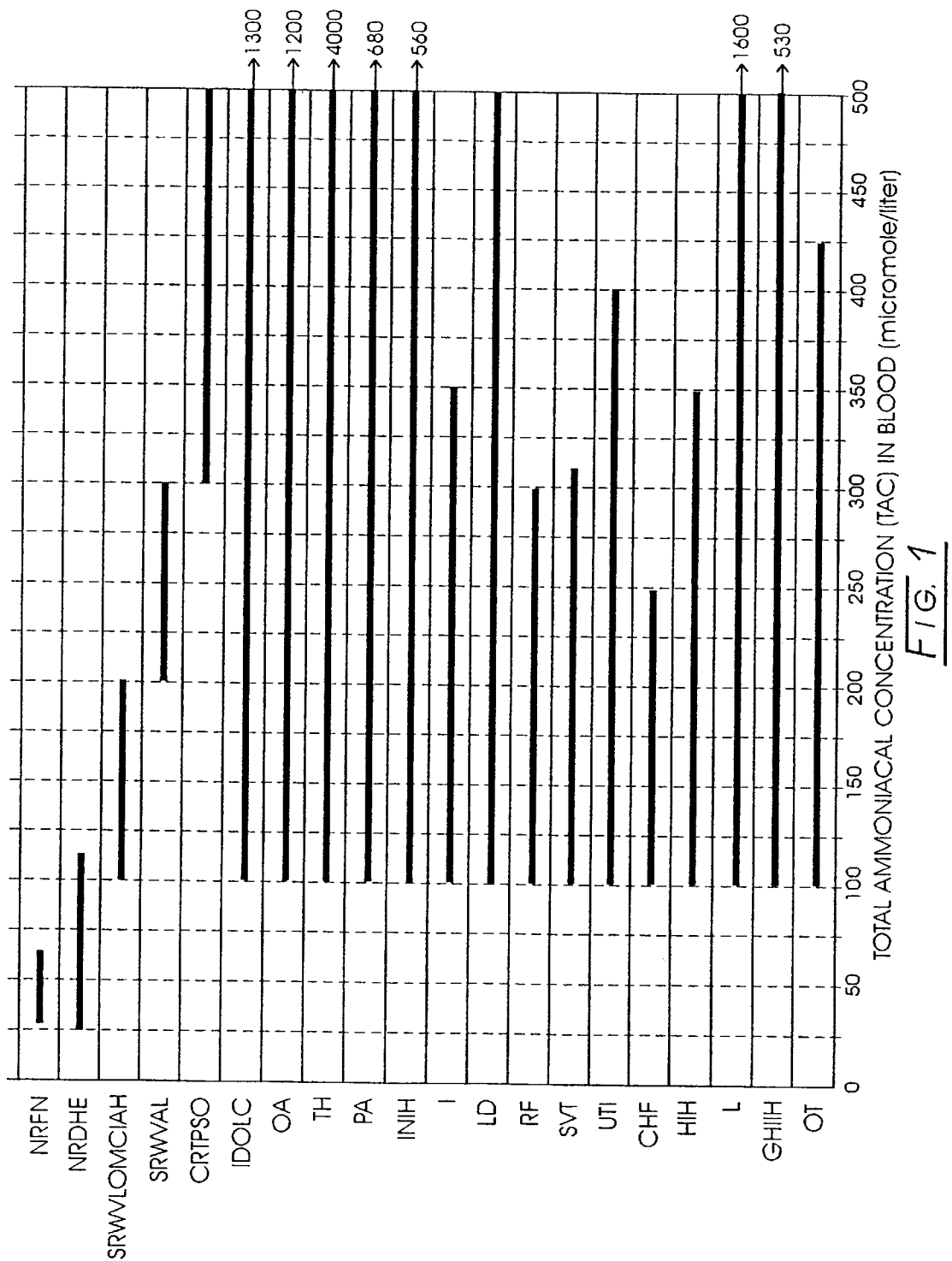
FIG. 1 is a chart illustrating blood ammonia levels for normal ranges and ranges associated with various diseases.

The system and method of the invention looks to a relatively rapid succession of measurements of total ammoniac content in the blood over an extended measurement interval. The multiple measurement approach generally will be seen to employ a control arrangement wherein total ammoniacal concentration ($C_{TAC}$) is computed in conjunction with a processor driven controller. Relatively normal or asymptomatic ranges for this total ammoniac concentration have been the subject of prior investigation, as well as higher values associated with symptomatic conditions. Practitioners using the system will desire to determine baseline values for TAC which may be somewhat unique to the preexisting condition of the patient. Accordingly the system provides for a manual inputting of a threshold level for total ammoniac concentration, $C_{th}$. Election by the clinical practitioner of appropriate thresholds for inputting to the system, will be carried out in cognizance of exhibited total concentration levels as well as reported symptomatic levels. Referring to FIG. 1, total ammoniacal concentration levels are charted in bar graph form. In the figure, a compilation is provided showing not only normal level ranges, but also, asymptomatic ranges to the highest levels heretofore reported in literature. Conditions, whether normal or otherwise, are shown as abbreviations developed with respect to the first letter of each word describing the condition. In Table 1 below, these abbreviations are listed in combination with their associated definitions.

TABLE 1

| | |
|---|---|
| NRFA | NORMAL RANGE FOR ADULTS |
| NRFC | NORMAL RANGE FOR CHILDREN |
| NRFN | NORMAL RANGE FOR NEONATES |
| NRDHE | NORMAL RANGE DURING HEAVY EXEXCISE |
| SRVWLOMCIAH | SYMPTOMATIC RANGE WITH VOMITING, LOSS OF MUSCLE COORDINATION, IRRITABILITY AND/OR HYPERACTIVITY |
| SRWVAL | SYMPTOMATIC RANGE WITH VOMITING AND LETHARGY |
| CRTPSO | COMATOSE, RESPONSIVE TO PAINFUL STIMULI ONLY |
| IDOUC | INHERITED DISORDERS OF UREA CYCLE |
| OA | ORGANIC ACIDEMIAS |
| TH | TRANSIENT HYPERAMMONEMIA |
| PA | PERINATAL ASPHYXIA |
| INIH | INTRAVENOUS NUTRITION INDUCED HYPERAMMONEMIA |
| I | INFECTON/SEPSIS |
| LD | LIVER DISEASE |
| RF | RENAL FAILURE |
| SVI | SODIUM VALPORATE THERAPY |
| UTI | URINARY TRACT INFECTIONS |
| CHF | CONGESTIVE HEART FAILURE |
| HIH | HEMODIALYSIS INDUCED HYPERAMMONEMIA |
| L | LEUKEMIA |
| GUIH | GLYCINE UPTAKE INDUCED HYPERAMMONEMIA |
| OT | ORGAN TRANSPLANT |

For patients undergoing total ammoniacal content monitoring from a starting condition representing normality, the practitioner typically will elect a threshold under which the system provides an alarm somewhere between total ammoniac concentrations (TAC) of about 100 $\mu$mol/liter to about 150 $\mu$mol/liter. At blood ammoniacal levels between about 200 and 350 $\mu$mol/liter, the patient generally presents as asymptomatic as represented in the table. However, it should be observed that during normal heavy exercise, ammoniacal levels will elevate, for example, to levels above 100 $\mu$mol/liter. When patients present exhibiting total ammoniacal content levels well above these lower thresholds, then to avoid the irritation of a constantly published alarm, the threshold may be established at elevated levels. The system also will indicate a warning, for example, as may be generated by an amber illuminator indicating that the ammoniacal levels are increasing from measurement to measurement. Additionally, the system looks to an increase over a set threshold for rate-of-rise of total ammoniacal level to alert the practitioner with an appropriate alarm.

Advantage also may be taken of the relative rapidity of measurement of total ammoniacal content (TAC) by deriving real time based trending which may be visually represented in graphical format in a display readout which also, will provide real time and total ammoniacal content values in numeric form. To avoid distractive overly rapid numeric changes for TAC, the system preferably employees a moving average filtering approach wherein an inputted number, n, of successive TAC values are averaged and that average is updated with each measurement on a first in last out basis. Thus, readability of the numeric data is improved and any erratic readings are somewhat accommodated for.

Figure 2:
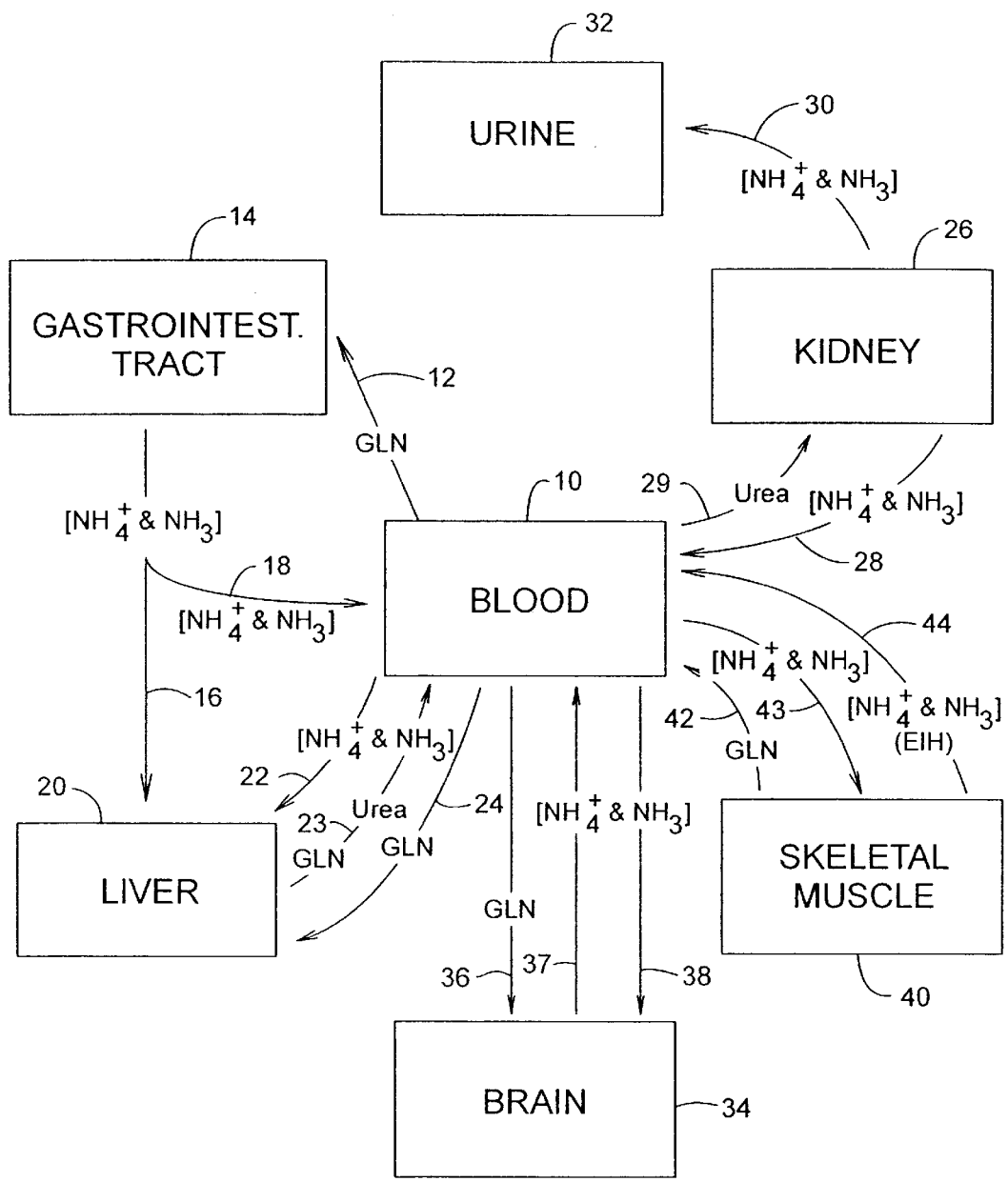
FIG. 2 is a block diagram illustrating various sources, metabolism sites, and clearance pathways for ammoniacal products in the human body.

The role of ammoniacal fluid in body physiology has been subject of extensive investigation. See, for example: Lockwood, A. H. et al., "The Dynamics of Ammonium Metabolism in Man—Effects of Liver Disease and Hyperammonenia," *J. Clin. Inves.*, Vol. 63, pp 449–460, 1979. Under resting conditions, most blood ammoniac content is of dietary origin. Normal digestive processes generate ammoniacal concentration from ingested protein, while bacteria in the gastrointestinal track generates ammoniacal concentration by metabolizing protein products of dietary protein digestion and urea. An illustration of the major organs of ammonia/ammonium formation, utilization and circulation is presented in FIG. 2. The figure includes representations of the various forms of nitrogenous compounds, e.g., ammonia gas ($NH_3$), ammonium ion ($NH_4^+$) or related nitrogenous by-products. Ammonia/ammonium metabolically formed in a given organ of the body generally is widely distributed. In FIG. 2, the blood pool or blood system is represented at block 10. Blood pool 10 is depicted supplying glutamine (GLN) to the gut or gastrointestinal tract as represented at arrows 12 and bock 14. Ammonia/ammonium generated in the gut as at 14 from protein digestion and deamination of glutamine (GLN) enters the portal venous circulation as represented at arrow 16 and 18 and is involved in the liver function as represented at block 20. The metabolic relationship of the blood pool or blood system 10 with the liver is represented by arrows 22–24. Metabolic interaction with the kidney as at block 26 is represented at arrows 28 and 29, while catabolic ammonium is excreted as represented at arrow 30 and block 32. Transport to and from the brain with respect to the blood pool is represented at block 34 and arrows 36–38. A similar metabolic interrelationship with respect to skeletal muscle is represented at block 40 and arrows 42 and 43. Exercise induced hyperammonemia (EIH) will witness a transfer of ammonium ion into the blood supply as represented at arrow 44. It may be observed that such relatively short excursions thus are readily tolerated by the body. See generally "Exercise-Induced Hyperammonemia: Peripheral and Central Effects," Bannister, et al., Int.J. of Sports Medicine, Vol. 11, pp 5129–5142 (1990). Under conditions typical of patients in an intensive care unit, resting muscles take up ammonia/ammonium from the circulating blood wherein the substance enters into protein synthesis via ketoglutaric and glutamic acid. When the muscle begins working again, ammonia/ammonium is once again released from the muscle into the bloodstream. If additional ammonia/ammonium (in the form of ammonium salt solution) is injected into a peripheral vein, the added ammoniacal content is brought directly to tissue via the blood where it may be retained and eventually used for amino acid and protein synthesis. See: Furst, P. et al. "Nitrogen Balance After Intravenous and Oral Administration of Ammonia Salts in Man," *Journal of Applied Physiology*, Vol. 26, No. 1, pp 13–22 (1969).

Figure 3:
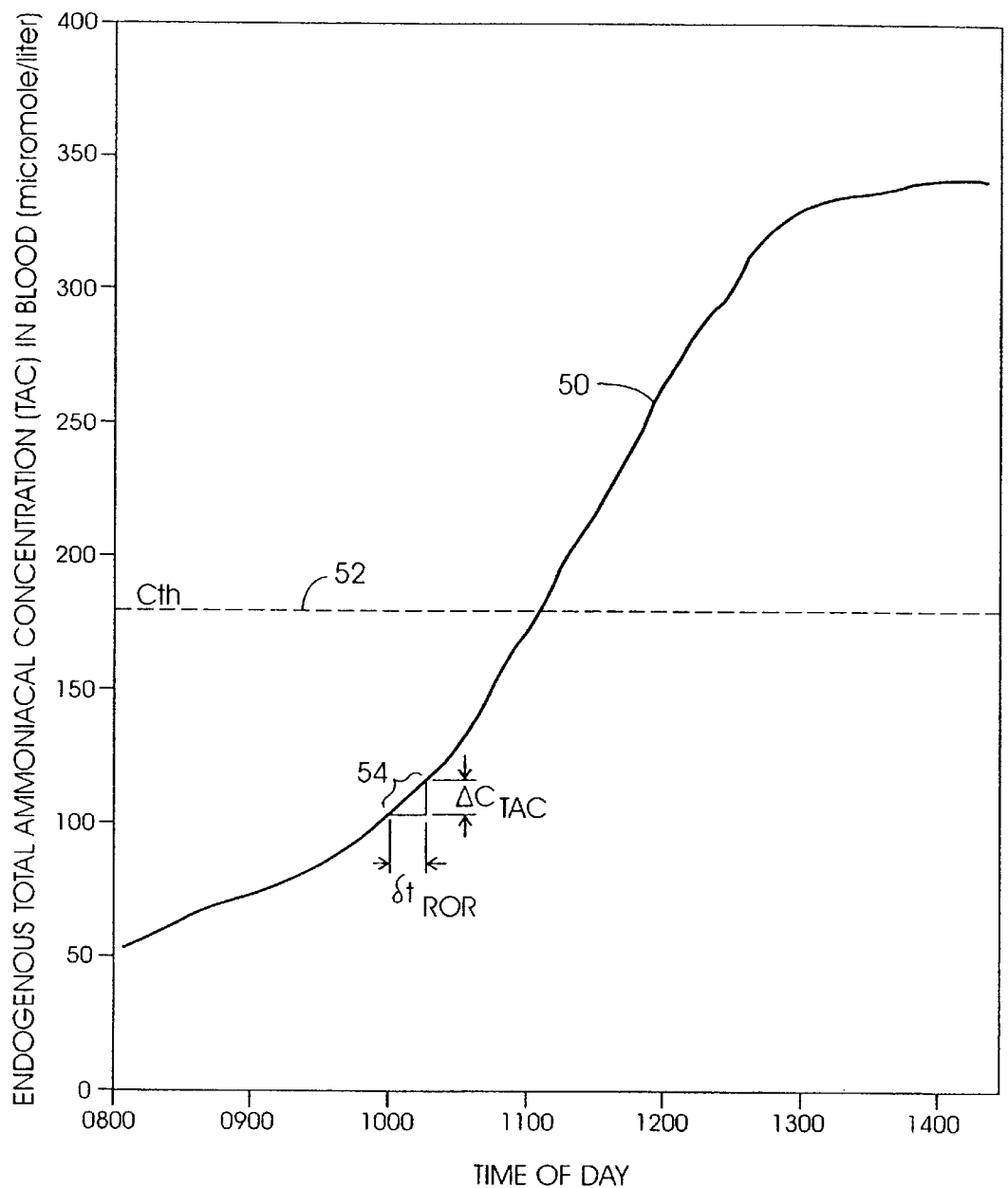
FIG. 3 is a stylized graph showing a rate-of-rise for endogenous total ammoniacal concentration (TAC) with respect to real time.

The availability to the practitioner of displayed trends in total ammoniacal concentration (TAC) in blood as well as the opportunity to establish thresholds both with respect to TAC level and threshold rates of elevation of TAC are of value in establishing a prompt treatment of such elevating TAC level conditions. Additionally, a warning (preferably non-audible) to the practitioner that such TAC levels are elevating is of value for achieving an early as possible treatment of excessive ammoniacal levels. These levels may rise at a relatively rapid pace. Looking to FIG. 3, an idealized curve 50 drawn from both literature and animal studies with respect to the introduction of ammoniacal levels is presented in conjunction with a similarly typical time of day representation. When the patient presents with such rapidly elevating TAC levels, the alarms and warnings will be generated. In this regard, the blood TAC threshold value, $C_{th}$ is represented at dashed line 52 at a level of about 180 $\mu$mol/liter. The rate of increase of TAC level, for example, taken over time interval commencing at a time of day of about 1000 is represented at the curve region 54. Such rate is determined as a division of the change in blood total ammoniacal concentration identified in simple form as "$\Delta C_{TAC}$" is divided by the time interval "$\delta t_{ROR}$". Where the rate-of-rise, as computed, exceeds a rate-of-rise inputted by the practitioner as a threshold, then an alarm is developed which may be either or both audible and visual in cuing extent.

The instrumentation employed for carrying out sequential measurements of total ammoniacal concentration in blood (TAC) may involve relatively short inline catheter structures carrying at least a sensor channel which incorporates a sensor responsive to one component of the ammoniacal concentration in blood. That component, for example, may be ammonia ($NH_3$) or ammonium ($NH_4^+$). Because of variations in vascular system vessel cross-sectional sizes and the presence of branching and hydraulic impedance phenomena, the instrumentation also may employ devices insertable within the vascular system which are quite diminutive in diametric size, so as to present minimum impedance to bloodflow. Where, for example, neonate infants are involved, peripheral vascular diametric extent may be quite small necessitating such diminutive size. Further, the system looks to the utilization of its sensing capability with blood by-pass devices which may assume a variety of mechanical designs. Typically catheters will be employed in conjunction with the vascular system at a peripheral region of the body which is considered to be a region remotely disposed from the heart. In general, this type of interaction with the bloodstream or blood from the bloodstream may be considered to be less invasive.

Figure 4:
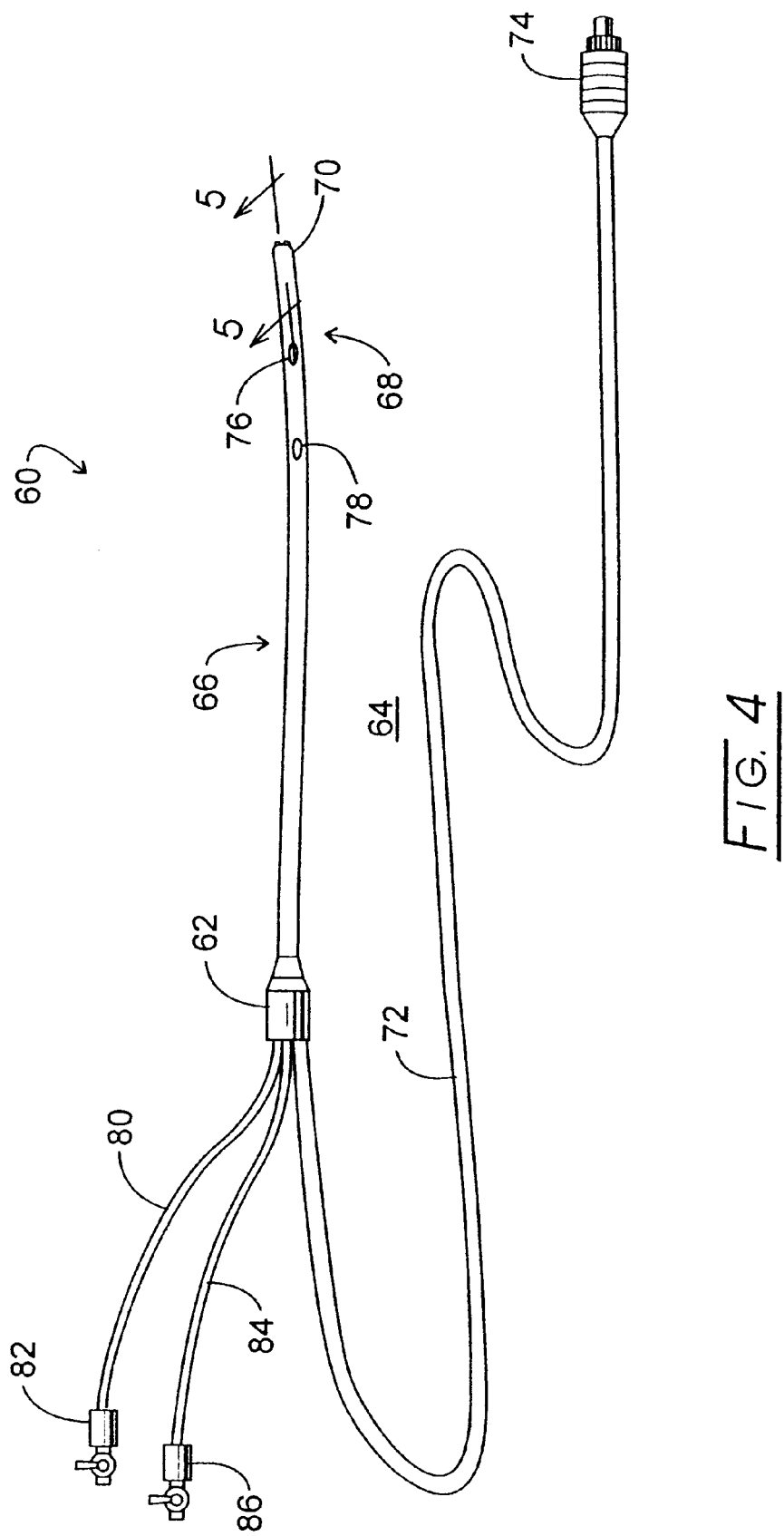
FIG. 4 is a pictorial view of a catheter employed with the system and method of the invention.

Referring to FIG. 4, a catheter assembly is represented generally at 60. Assembly 60 is configured for insertion within the bloodstream of the vascular system located in a peripheral region of the body. Such a region will, for example, be in a forearm radial artery or ulnar artery. Where excessive blood hydraulic impedance is encountered, the sensing components may be extended into the brachial artery. Having a body portion 66 intended for vascular positioning which is of somewhat short lengthwise extent, for example, five to ten inches, this portion extends from a base 62 within a relatively extended proximal region represented generally at 64 to a measurement region 68 extending, in turn to a tip 70. Located within the measurement region 66 and, preferably, extending from tip 70, are two fiberoptic channels (not shown) which extend to base 62 for further continuous communication with a fiberoptic cable 72 terminating in a fiberoptic connector 74. Connector 74 is configured for insertion within a two channel fiberoptic input of a controller. Two additional or auxiliary channels may be provided within the structure 66 which terminate, for example, in a distal auxiliary port 76 and a proximal auxiliary port 78. Distal auxiliary port 76 extends to a flexible tubular conduit 80 coupled in fluid transfer relationship with the channel at base 62. Conduit 80, terminates in a connector and valve assembly 82. In similar fashion, the auxiliary channel extending to proximal port 78 in turn, leads to base 62 at which position it is connected in fluid transfer association with a conduit 84 terminating, in turn, at a connector and valve assembly 86. These auxiliary channels may, for example, be employed for the purpose of withdrawing blood for sampling, for the infusion of irrigants, or delivery of medicants.

Referring to FIGS. 5 and 6, the structure of catheter 60 extending from its measurement region 68 is revealed in sectional fashion. Additionally, in the former figure, signal treating aspects of a controller function represented at 90 are depicted. In general, the body portion 66 of the catheter assembly 60 is formed of a medical grade polymeric material which is slightly flexible, permitting sufficient flexure for facile insertion through an introducer into a vascular vessel for contact of the measurement region 68 with the bloodstream. The polymeric body portion 66 is shown having an outer cylindrical surface 94. Formed typically by extrusion through the body portion 66 is a first sensor channel 96 which extends from the base 62 (FIG. 4) to tip 70 and which serves to support an ammoniacal component sensor assembly represented in general at 98 and seen to be comprised of a fiberoptic strand 100 extending to an ammoniacal component responsive forward assembly represented generally at 102. Assembly 102 includes the confronting face or tip surface 104 of the fiberoptic strand 100 which is seen to be extending slightly forwardly of the forward surface 106 of the body portion 66 of catheter 60. Forward assembly 102 further includes a membrane 108 which, inter alia, forms a blood confronting surface of an ammoniacal component concentration reactor which may take a variety of configurations. For example, the elected ammoniacal component may be ammonia ($NH_3$) and the reactor may be selected to be a gaseous ammonia sensitive dye which may be captured by the membrane either by admixture therewith or by encapsulating the dye intermediate the membrane 108 rear face and the forward face 104 of the fiberoptic strand 100. For the former approach, the dye is deposited upon the membrane surface for migrating into its pore structure. This approach has been observed to improve response time. With the above arrangement, the fiberoptic strand 100 functions as a transmission assembly for conveying a signal corresponding with the output condition of the reactor along the body portion 66 to connector 74. (FIG. 4).

Positioned diametrically opposite the first sensor channel 96 is a second sensor channel 110 again extending from the forward surface 106 of body portion 66 to the base 62 (FIG. 4). Sensor channel 110 functions to support a pH sensor structure represented generally at 112. Structure 112 includes a pH responsive forward assembly represented generally at 114 formed including the forward portion of a fiberoptic strand 116, the forward face 118 of which is seen to protrude slightly from forward surface 106 of catheter body portion 66 at tip 70. Forward assembly 114 of the sensor 112 may assume a variety of configurations for carrying out in vivo measurement of pH. In this regard, typically, a pH-sensitive indicator is immobilized on the face 118. Light energy of a selected wavelength is guided along the fiberoptic strand 116 to excite the indicator which then fluoresces and resultant emission intensity is a function of the pH of blood within the bloodstream. To provide the forward assembly structure 114, the face 118, supporting the indicator is covered with a hydrogen ion permeable membrane represented at 120 which is impermeable to the other constituents of blood.

FIG. 6 reveals the distal auxiliary port 76 extending through the outer cylindrical surface 94 of the body portion 92. Port 76 is in fluid transfer communication with an auxiliary channel 122 which extends to the base 62 and thence to a fluid transfer communication with conduit 80. In similar fashion, the proximal auxiliary port 78 (FIG. 4) is in communication with auxiliary channel 124 which extends, in turn, to face 62 and thence to a fluid communication with conduit 84.

FIG. 5, shows that the fiberoptic components of ammoniacal sensor assembly 98 and pH sensor assembly 112 extend to signal treatment components of a controller function, as represented in block form, at 124 and 126. Cable 72 (FIG. 4) is symbolically represented by dual arrows 128 and 130, the former extending from the ammoniacal sensor assembly 98 and the former from the pH sensor assembly 112. The signal treatment function represented at block 124 includes a light source (LS) and transducing (T) network 132, the interactive association with arrow 130 being represented by dual lines 134 and 135. In similar fashion, arrow 128 is seen to be operationally associated with a light source (LS) and transducing (T) network 138, the interactive operational association with arrow 128 being shown by lines 140 and 141. For the fiberoptic embodiment shown, networks 132 and 138 function to interrogate the reactor components of forward assemblies 102 and 114 to provide an analog signal at outputs represented at respective lines 144 and 145. These analog signals then are converted to digital form as represented at the analog-to-digital conversion block 126. The resultant digital data then is submitted for processing as represented at arrow 146.

The type of sensor technology employed with the ammoniacal concentration monitoring may vary somewhat and is generally selected with respect to the ammoniacal component, i.e., ammonia gas ($NH_3$) or ammonium ion ($NH_4^+$) being monitored. The system and methodology of the invention may be employed with catheters, certain of which may be of very minimal outer diametric extent to avoid undue blood hydraulic impedance, and also may perform in an ex vivo fashion. In the latter regard, a bypassing approach may be employed not only with respect to ameliorating the noted hydraulic effect but also may be used in conjunction with pre-established bypass related modalities such as in dialysis procedures where hyperammonemia may present itself or in such modalities as heart bypass procedures wherein organ failure may be manifested in elevation of ammoniacal levels. The forward assemblies of the sensor systems should be located within the blood being evaluated in a manner optimizing their performance. Thus, where the sensors are employed with catheters, such devices should be in an orientation wherein their principal sensing surface confronts the direction of bloodflow as opposed to being in an orientation where blood flows over their rearward portion and a tip located sensing surface. The later kind of orientation in the bloodstream tends to develop depletion regions at a forward sensing surface. Where measurement occurs ex vivo and is carried out in conjunction with flowing blood, the same geometry of bloodflow and sensor association is preferred. Positioning the forward assembly sensing tip or face in less than desired orientations has been found to extend the interval required to achieve measurement value equilibrium. In general, the optical sensors include: direct spectrometric sensors; indirect spectrometric sensors; transmission spectrometric sensors; transmission/reflective spectrometric sensors; colorimetric sensors; and fluorometric sensors. Such sensors are described in conjunction with schematic representations of them in the figures to follow.

Figure 7:
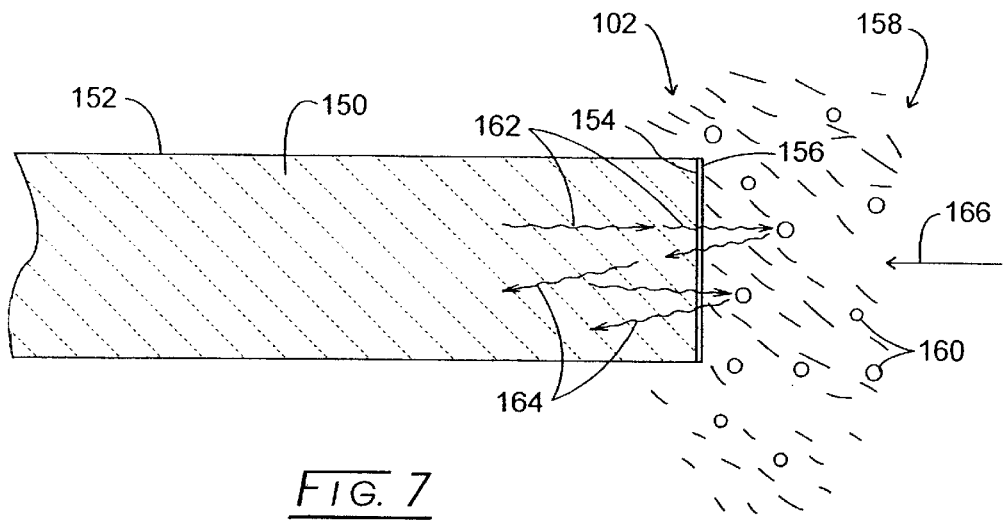
FIG. 7 is a schematic representation of a front end assembly of a concentration sensor employed with the invention.
Figure 8:
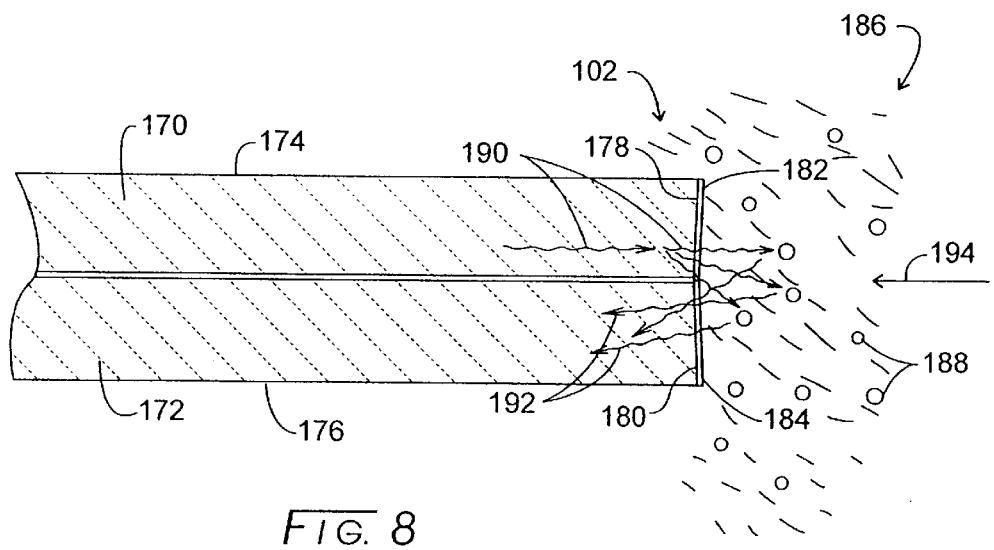
FIG. 8 is a schematic representation of the front end assembly of a concentration sensor which may be employed with the invention.

Considering initially the direct spectrometric sensors, reference is made to FIGS. 7 and 8. In FIG. 7, the forward assembly of one such ammoniacal component concentration sensor is revealed. This sensor, for example, directly measures the ammonia gas component of the blood. With this arrangement an optical fiber 150 is employed. Fiberoptic component 150 is mounted within a sensor channel, for example, as represented at 96 in FIGS. 5 and 6. Component 150 is surrounded along its lengthwise extent by a sheath 152. Tip or forward face 154 of component 150 is coated with a very thin, optically transparent coating 156. Coating 156 is an anti-coagulant such as heparin which functions to reduce the possibility of deposits such as fibrin or blood coatings over the tip 154. The embodiment of FIG. 7 is one wherein there is a simultaneous transmission of light at one or more predetermined wavelengths and reflectance reception of that light. In this regard, the bloodstream is schematically represented in general at 158. The ammonia gas ($NH_3$) component of the bloodstream is analyzed with the instant embodiment and particles of that gas are represented at 160. For the preferred embodiment wherein ammonia gas is the elected ammoniacal component, analysis is made by light transmission to and reflectance from the ammonia gas particles 160. Light transmission is schematically represented in the figure as wave arrows 162, while reacting reflectance or reflections are represented by the wave arrows 164. This latter reflective illumination as represented by the arrows 164 will exhibit a spectrum which is characteristic of the ammonia component and the intensity of the spectral portions thereof will be related to the concentration of ammonia 160 within blood 158. As noted above, it is preferred that the face 154 of the forward assembly 102 confront the direction of bloodflow as represented by arrow 166. In general, the diameter of the fiberoptic component 150 will be in a range from about 50 to 1000 microns, and preferably falls at a range of about 100 to 500 microns for conventional catheter applications. A typical diameter for the latter applications will be about 250 microns.

The transmission and reception of investigatory light at one or more predetermined wavelengths also may be carried out using two or more fiber components. In one approach, two fiber components are positioned in immediate adjacency. Alternately, one fiberoptic component may provide a transmission aspect while a group of such fiber components surmounting a central transmission fiber component carries out the opposite or reception function. In such an arrangement, the transmitted light and reflected or emitted light are advantageously separated during their transmission to and from the blood. In FIG. 8, the forward sensor assembly is again represented at 102. The fiberoptic assemblies employed with the optical sensor may be singular fibers which are typically formed of plastic or when formed of glass, typically are provided as bundles or multiple strands of glass. In the instant figure, two optical fibers are schematically represented at 170 and 172. The lengthwise extent of each of these fibers is enclosed within a sheath as represented, respectively at 174 and 176. Tip surfaces or faces of respective fibers 170 and 172 are configured such that tip surface or face 178 is slightly canted inwardly as is the opposite surface or face 180. Tip surfaces 178 and 180 additionally may be coated as respectively represented at 182 and 184, with an optically transparent anti-coagulant such as heparin. The overall diameter of the transmission/ reflection separated assembly will be selected as the same as the overall diameter of the single fiber arrangement of FIG. 7. In the instant figure, the bloodstream is represented in general at 186, and the ammoniacal component, ammonia gas (NH$_3$), is represented for instance, at 188. With the arrangement shown, light of one or more wavelengths is transmitted through fiber assembly 170 as represented by the transmission wave arrows 190. Resultant reflection, as represented by the transmission wave arrows 192, is collected and transmitted by fiberoptic assembly 172 for analysis. With this sensing forward structure, the transmitted light and reflected light are advantageously separated during their transmission to and from the bloodstream or blood 186. In general, this enables a more accurate quantitative measurement of spectral intensity and in turn, a more accurate measurement of the concentration of ammonia (NH$_3$) as represented at 188. It may be noted, by way of example, that the direct measurement arrangement of FIGS. 7 and 8 may be used to measure both ammonia (NH$_3$) concentration as well as the oxygen saturation level of the blood. Particularly for the catheter form of embodiments, the tip surfaces of the forward assemblies and their associated coatings preferably are oriented to directly confront the direction of flowing blood in the bloodstream as represented by arrow 194. This generally reduces the interval required to evoke a valid measurement and assures an appropriate contact of the bloodflow against the forward faces of the sensor forward assemblies.

Figure 9:
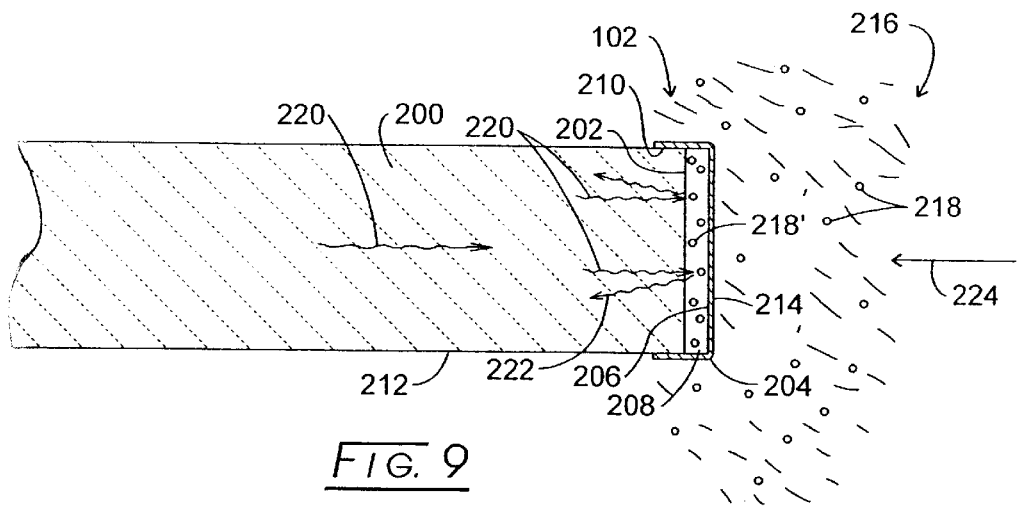
FIG. 9 is a schematic representation of a membrane containing front end assembly of a concentration sensor which may be employed with the invention.

Now considering indirect spectrometric sensor technology, reference is made to FIGS. 9, 10, 11A and 11B. In FIG. 9, the forward assembly of the sensor, as represented generally at 102 includes a fiberoptic transmission/reception assembly 200 which extends to a tip surface or face 202. Positioned over the tip surface 202 is a cap-shaped membrane 204 having a forward inner surface portion 206 which is spaced from tip surface 202 to define a gap 208. A peripheral inner surface 210 of membrane 204 is sealed to the outer surface 212 of fiberoptic assembly 200 to assure the integrity of the gap 208. The outer surface 214 of membrane 204 is in contact with blood or flowing blood of the bloodstream represented generally at 216. As before, the ammoniacal component preferred for measurement is ammonia gas (NH$_3$), particles of which are represented in exemplary fashion at 218. Membrane 204 is structured to contain microscopic pores and functions to minimize or block the ingress of water and other liquid components within the blood 216 while permitting the ammoniacal component of interest, for example, ammonia gas, to rapidly defuse across it due to a developed concentration gradient. In effect, a fluid space is developed at the gap 208 containing the measured ammoniacal component as represented at 218'. With the arrangement, an equilibrium develops between the ammoniacal component 218' and the component as at 218. One or more wavelengths of light, as represented by the transmission wave arrows 220 are transmitted into gap 208 and reflections from the ammoniacal components such as ammonia gas 218' as are represented by reflection wave arrows 222, then may be analyzed. The intensity of the reflected light is represented by these arrows 222 and the concentration of the ammoniacal component is correlatable with the intensity of the light at one or more wavelengths. Light transmitted as represented at arrows 220 may be of specific wavelengths or a spectrum of wavelengths may be employed. The advantage of this sensor structuring resides in the simplification of spectral analysis, inasmuch as the species of interest has been separated from other blood-carrying species. The membrane 204 as well as the membrane employed with other embodiments of the invention may be provided as a Teflon barrier, for example, manufactured by W. L. Gore & Associates, Inc., of Elkton, Md. These membranes contain microscopic pores whose size, for the ammonia ammoniacal component, preferably are the range from 0.02 to 3 microns. The overall thickness of the membrane 204 will be in the range of from 1 to 500 microns and, preferably, in the range of 10 to 50 microns. The hydrophobic nature of the Teflon material serves to minimize ingress of water and other liquid components within surrounding blood. As before, it is preferred that the forward face or outer sensing surface of the forward assembly 102 confront the direction of flow of the bloodstream 216, such direction being represented by arrow 224. For catheter applications of the system, this calls for positioning the measurement region of the catheter at its tip in confronting relationship with the direction of bloodflow.

Figure 10:
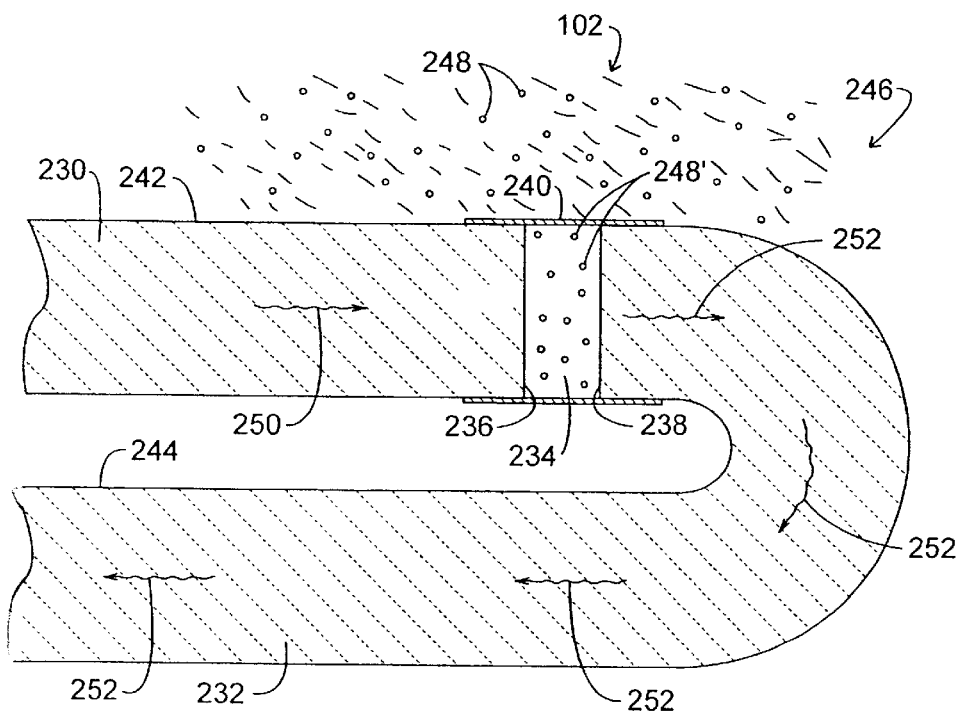
FIG. 10 is a schematic representation of a membrane containing front end assembly of a transmission-type concentration sensor which may be employed with the invention.

A transmission spectrometric sensor is illustrated in FIG. 10, forward assembly 102 of the sensor being schematically revealed for this configuration. In the figure, the fiberoptic assembly is seen to have a generally U-shaped configuration with a light transmission leg 230 and a return leg 232. With the configuration, there is, as in the case of FIG. 9, a gap 234 defined between the end face 236 of transmission leg 230 and the end face 238 of return leg 232. A surmounting membrane 240, which may be of cylindrical shape, is positioned across the gap 234 and sealed against the outer surfaces 242 and 244 of respective legs 230 and 232. As before, the membrane 240 is configured having microscopic pores which permit the ingress of the elected ammoniacal component from the blood or bloodstream. In this regard, such blood or bloodstream is represented in general at 246 and the ammoniacal component, for example, ammonia gas (NH$_3$) is represented symbolically, for example, at 248. The sensor forward assembly 102 being so configured, when it is immersed within the blood or bloodstream 246, a concentration gradient builds between such blood 246 and the gap 234 to provide for the migration of the ammoniacal component such as ammonia gas into the gap, such migrated ammonia gas being represented within the gap at 248'. Light having one or more wavelengths is transmitted toward the gap 234, as represented by transmission wave arrow 250 to be selectively attenuated by the ammonia gas 248'. The thus attenuated light then is returned for analysis, as represented by wave arrows 252. Such analysis quantifies the concentration of ammonia gas in the gap 234 and, hence, in the blood or bloodstream 246. As in the case of FIG. 9, this arrangement has the advantage of isolating the ammoniacal component of interest to simplify analysis. No blood directional arrows are shown in the instant figure, inasmuch as the forward assembly 102 may be used in longitudinally directed bloodflows moving in forward or rearward directions with respect to it as well in bypass systems wherein blood movement may be transverse to the longitudinal axis of the sensor.

Figure 11A:
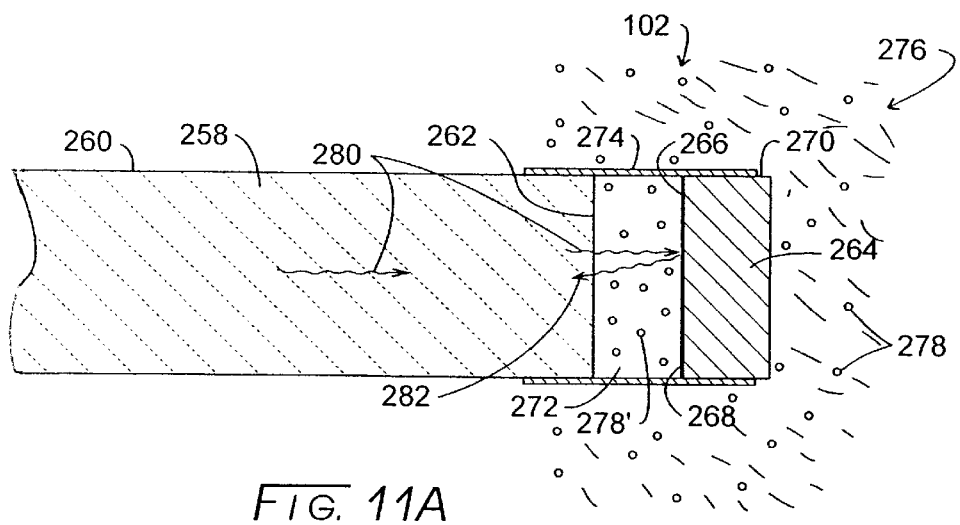
FIG. 11A is a schematic representation of a front end assembly of a concentration sensor which may be employed with the invention.
Figure 11B:
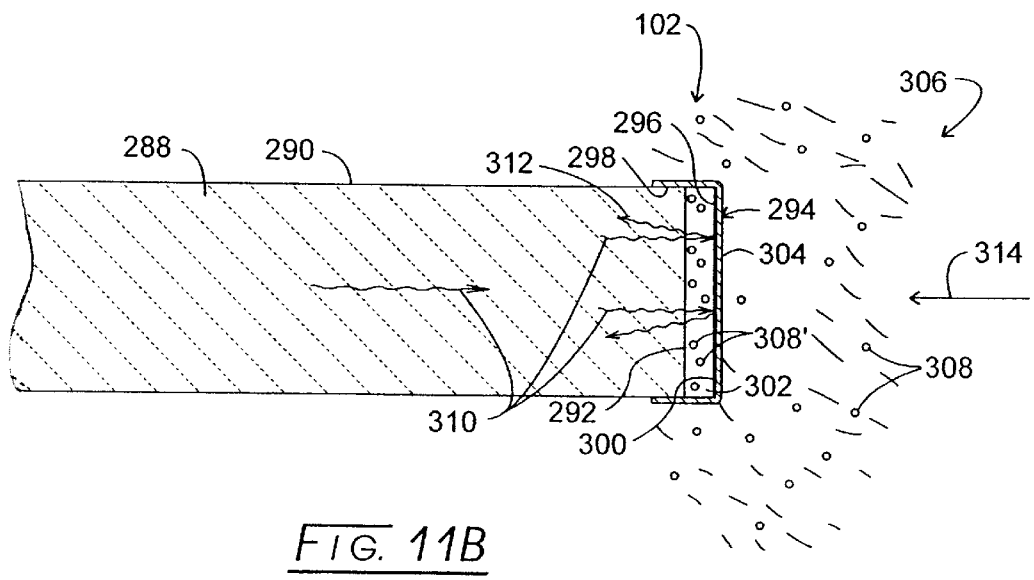
FIG. 11B is a schematic representation of the front end assembly of a concentration sensor which may be employed with the invention.

Schematic representations of transmission/reflectance spectrometric sensors are provided in FIGS. 11A and 11B. Looking to FIG. 11A, the forward assembly 102 for this embodiment is seen to comprise an optical fiber assembly 258 having a surface 260 and extending to a tip surface or face 262. Spaced from the surface 262 is a polymeric end piece 264 having an inwardly disposed surface 266 which supports a light reflector provided as a coating or the like as seen at 268. The edge surface 270 of end piece 264 is dimensioned in correspondence with the side surface 260 of the assembly 258.

Light reflecting surface 268 is spaced from tip surface 262 a distance defining a gap 272 and a cylindrical membrane 274 is seen to surround and further define gap 272. In this regard, the membrane 274 is sealed to side surfaces 260 and 270. Forward assembly 102 is immersed in the blood or bloodstream represented in general at 276. The ammonia ($NH_3$) ammoniacal component is represented within the bloodstream 276, for example, at 278. With the arrangement, a concentration gradient is developed between the bloodstream or blood 276 and the gap 272. The microstructure of the membrane 274 permits a migration of the ammoniacal component of interest, for example, ammonia, into the gap as represented at 278'. Light is transmitted along the assembly as represented by the wave transmission arrows as at 280, whereupon it is reflected from the light reflecting surface 268 and returned as represented by wave transmission arrow 282. The interaction of this light in crossing the gap 272 then is analyzed to develop values for the concentration of the ammoniacal component such as ammonia. The sensor configuration of this embodiment is particularly suited for employment within the sampling chambers of blood bypass systems where blood is flowing transversely to the longitudinal axis of a fiberoptic assembly 258.

Referring to FIG. 11B, an alternative structuring of the transmission/reflectance spectrometric sensor is revealed. The forward assembly 102 is seen to be structured incorporating a fiberoptic assembly 288 having a side surface 290 and extending to a tip surface or face 292. Positioned over the forward end of the fiberoptic assembly 288 is a cap-configured membrane represented generally at 294 having an inwardly disposed surface 296 and a peripheral, cylindrically-shaped inward surface 298. Supported by the inwardly-disposed surface 298 is a light-reflecting component present as a coating and shown at 300. The peripheral inward surface 298 of the membrane 294 is sealed to the side surface 290 of fiberoptic assembly 288 to define a gap 302. Outwardly disposed surface 304 of membrane 294 is immersed in blood or a bloodstream as represented in general at 306. As before, the membrane 294 is configured having microscopic pores permitting the migration of the analyte component such as ammonia represented at 308 into the gap 302 by virtue of the evolution of a concentration gradient between the gap 302 and blood represented at bloodstream 306. Other components of the blood essentially are blocked from movement into the gap 302. Ammoniacal component or ammonia which will have migrated into the gap 302 is represented at 308'. Analysis of concentration of the ammoniacal component for ammonia 308', which is equilibrated with the corresponding concentration of ammonia 308, is made by directing light at one or more wavelengths across the gap 302 as represented by transmission wave arrows 310. This light interacts with the ammonia or component 308' and is reflected from the reflector component or coating 300 to return for analysis as represented by wave transmission arrows 312.

With the sensor geometry shown and where the sensor is positioned within a peripheral region of the vascular system, it is desirable that the forward surface 304 be positioned so as to confront the direction of flow of the bloodstream as represented at arrow 314. In other applications such as blood bypass applications, a transversely directed bloodflow or a temporarily quiescent blood quantity may be engaged with the surface 304 to permit appropriate measurement.

Figure 12:
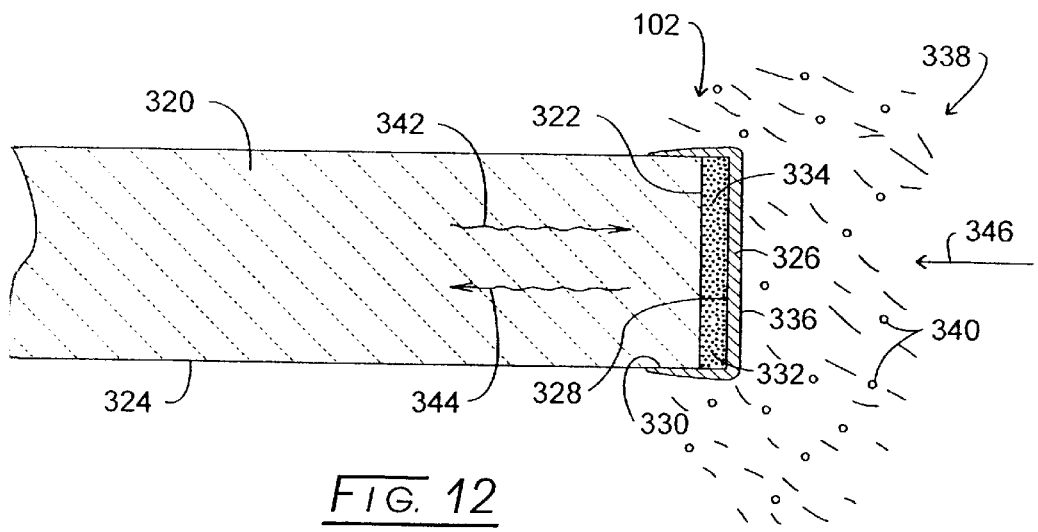
FIG. 12 is a schematic representation of a front end assembly of a concentration sensor which may be employed with the invention.

Referring to FIG. 12, a forward assembly 102 is illustrated schematically which has a structure common to both colorimetric and fluorometric sensors. The sensor arrangement includes a fiberoptic assembly 320 which extends to a tip surface or face 322 and is surrounded by a sheath 324. Mounted over the sheath 324 and fiberoptic assembly 320 is a cap-shaped membrane 326 having an inwardly-disposed surface 328 and an inwardly-peripherally-disposed surface 330. Surface 330 is sealed to the outer surface of sheath 324 in a manner spacing the inward surface 328 from the tip surface or face 322 a distance defining a gap 332. Located within this gap 332 is a reactor 334 which, for the structure shown, may be an analyte component responsive dye for the preferred colorimetric version of the sensor, or a reactor which fluoresces under light stimulation. The outward surface 336 of membrane 326 is immersed in blood or flowing blood of a bloodstream as represented in general at 338 and containing an ammoniacal component such as ammonia as represented, for example, at 340. For the preferred embodiment of the invention, wherein ammonia ($NH_3$) is the component of interest, and an ammonia-sensitive dye is employed for the reactor 334, the membrane 326 is configured having microscopic pores through which the ammonia 340 may migrate and chemically react with the dye-defined reactor 334. This will result in a change in coloration of the dye-defined reactor 334 which may be analyzed by colorimetric procedures. Accordingly, the reactor 334 is seen stimulated by light at one or more wavelengths as represented by the light wave transmission arrow 342. The resultant light reflected from the reactor dye is represented at transmission arrow 344. As before, it is preferred that for catheter based usage wherein the sensor forward assembly 102 is positioned within a vessel of the vascular system of the body, it be located to confront the direction of flow of the bloodstream as represented by arrow 346.

Figure 13:
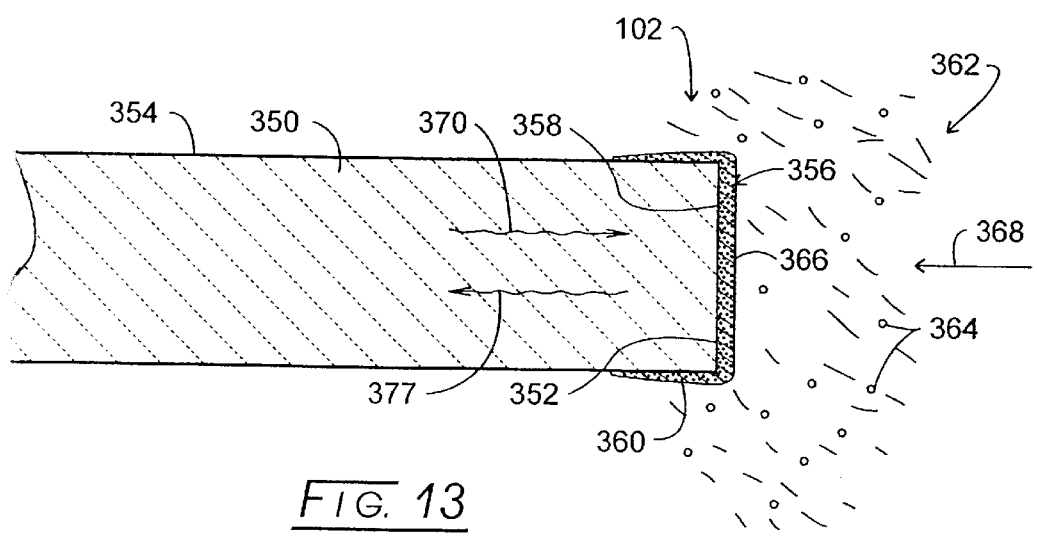
FIG. 13 is a schematic representation of a front end assembly for a concentration sensor which may be employed with the invention.

Referring to FIG. 13, a preferred arrangement for the forward assembly 102, particularly with respect to the sensing of the ammoniacal component ammonia ($NH_3$) is revealed. The sensor arrangement includes a fiberoptic assembly 350 which extends to a tip surface or face 352 and is surrounded by a sheath 354. Mounted over the sheath 354 and face 352 is a cap-shaped membrane represented generally at 356 having an inwardly-disposed surface 358 which is in intimate contact with the forward face 352 of the fiberoptic assembly 350. Surface 358 is sealed to the outer surface of sheath 354. In this regard, the membrane may be provided as a coating over the tip region 360 of fiberoptic assembly 350. The reactor of the sensor forward assembly 102 may be a dye or the like which is responsive to the ammoniacal component and which is incorporated within the membrane 356. In this regard, the reactor may be, for example, a dye which changes color with respect to the concentration of ammonia within a bloodstream 362 as represented, for example, at 364. Membrane 356 may be provided for example, as a silicone perthiorinated urethane, cellulose acetate butyrate or methymethacrylate polymer matrix incorporating a dye. The outward surface 366 of membrane 356 is shown immersed in flowing blood of the bloodstream 362 in a manner wherein it confronts the direction of flow of that bloodstream as represented at arrow 368. The ammonia affected reactor dye incorporated within the membrane 356 will respond to the migration of ammonia thereinto to evoke a change in coloration which may be analyzed, inter alia, by colorimetric procedures. Accordingly, the dye-containing membrane 356 is seen to be interrogated by light at one or more wavelengths as represented by light transmission arrow 370. The resultant light reflected from the reactor dye or the like as integrated within the matrix of membrane 356 is represented at transmission arrow 372.

Figure 14:
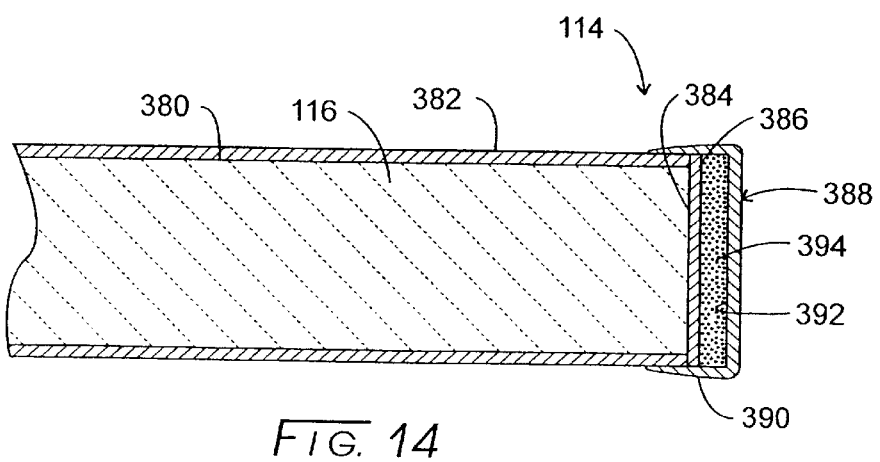
FIG. 14 is a schematic representation of a pH sensor which may be employed with the invention.

A system utilizing ammonia as the ammoniacal component and an ammonia sensitive dye as the reactor 334 which is incorporated in a membrane 356 is a preferred embodiment of the invention. Of the ammonia dyes available for use as such reactor, bromocreosol green, excited at wavelengths in a first band of 380 to 480 nm; in a second band of 520 to 680 nm; and in a third band of 700 to 900 nm; chlorophenol red excited at wavelengths in a first band of 380 to 420 nm; in a second band of 520 to 620 nm; and in a third band of 650 to 900 nm; bromophenol blue excited at wavelengths in a first band of 380 to 440 nm; in a second band of 520 to 640 nm; and in a third band of 700 to 900 nm; m-creosol purple; thymol blue; and congo red may also be considered. The light wavelengths for stimulation for interrogation conventionally are generated by light emitting diodes (LEDs) and the wavelengths utilized are based upon the wavelengths corresponding to the peak absorption intensity and wavelengths which are insensitive to changes in the ammonia concentration. If a plastic fiberoptic assembly is used, the preferred third wavelength is about 700 nm. If a glass fiberoptic light transmitting assembly is used, the preferred third wavelength of those cited above is within the range specified. Dyes serving as a reactor quite rapidly reach an equilibrium with the ammoniacal component under analysis. The intensity normalized reflectance of the responding wavelength of light 372 is utilized to quantitate the concentration of ammoniacal component (e.g., ammonia).

Where the reactor is provided as an ammoniacal component-sensitive fluorescent material upon excitation by light wavelengths, the level or intensity of fluorescence or the rate of quenching when a stimulation source is extinguished is correlated with the concentration of the ammoniacal component at hand.

Where the ammoniacal component is ammonia, as is preferred, in order to derive the value of total ammoniacal concentration, the value of the corresponding pH of the blood is utilized in a straight forward computation to find a total ammoniacal concentration. In general, the Henderson-Hasselbalch relationship is resorted to. pH may be measured with a variety of techniques using reactors which are chemical or ion selective electrode-based. A pH sensitive dye is employed in connection with the embodiment described in conjunction with FIGS. 4–6. Looking to FIG. 14, the front end assembly 114 represented generally in FIG. 5 is revealed in schematic fashion but at an enhanced level of detail. In the figure, fiberoptic strand 116 as it is present at the forward assembly 114 again is represented. The outer cylindrical surface 380 of strand 116 is covered with a sheath 382 and the tip surface or face 384 of the fiberoptic strand 116 is coated with a pH sensitive dye which is applied as a porous coating and is represented at 386. Sealingly positioned over the tip surface or face 384 and the dye or pH reactor 386 is a hydrogen ion permeable membrane represented generally at 388 which is cap-shaped having a cylindrical side component 390 sealed to the sheath 382. The inner forward surface 392 of membrane 388 is spaced from the dye layer or pH reactor 386 to accommodate a medium 394 whose pH is in equilibrium with the pH of the blood within which this forward assembly 114 is immersed. The pH sensitive dye or the like is interrogated by light at one or more wavelengths to determine the value of pH of the blood. For the present embodiment, the forward assembly 114 of the pH sensor is at the tip 70 of the catheter 60 (FIG. 4). It may perform at other locations, for example, adjacent one of the injectate ports 68 or 78. Additionally, for catheter structures of minimal size as described later herein, forward assembly 114 may be incorporated within a separate catheter or a separate support structure within an ex vivo sampling chamber of a bypass based system.

Optical sensors for the measurement of pH, particularly in connection with the in vivo measurement of pH of the blood are described, for example, in U.S. Pat. No. 5,607,644 by Olstein, et al, entitled "Optical Sensor for the Measurement of pH in a Fluid, and Related Sensing Compositions and Methods" issued Mar. 4, 1997. Additionally, description of such pH sensors is provided in the following publication:

Zhang, et al, "Evaluation of Fluorescent Dyes for In Vivo pH Measurement", Medical & Biological Engineering & Computing, March 1994, pp 224–227.

These references describe, in particular, fluorescing pH analysis techniques.

Figure 15:
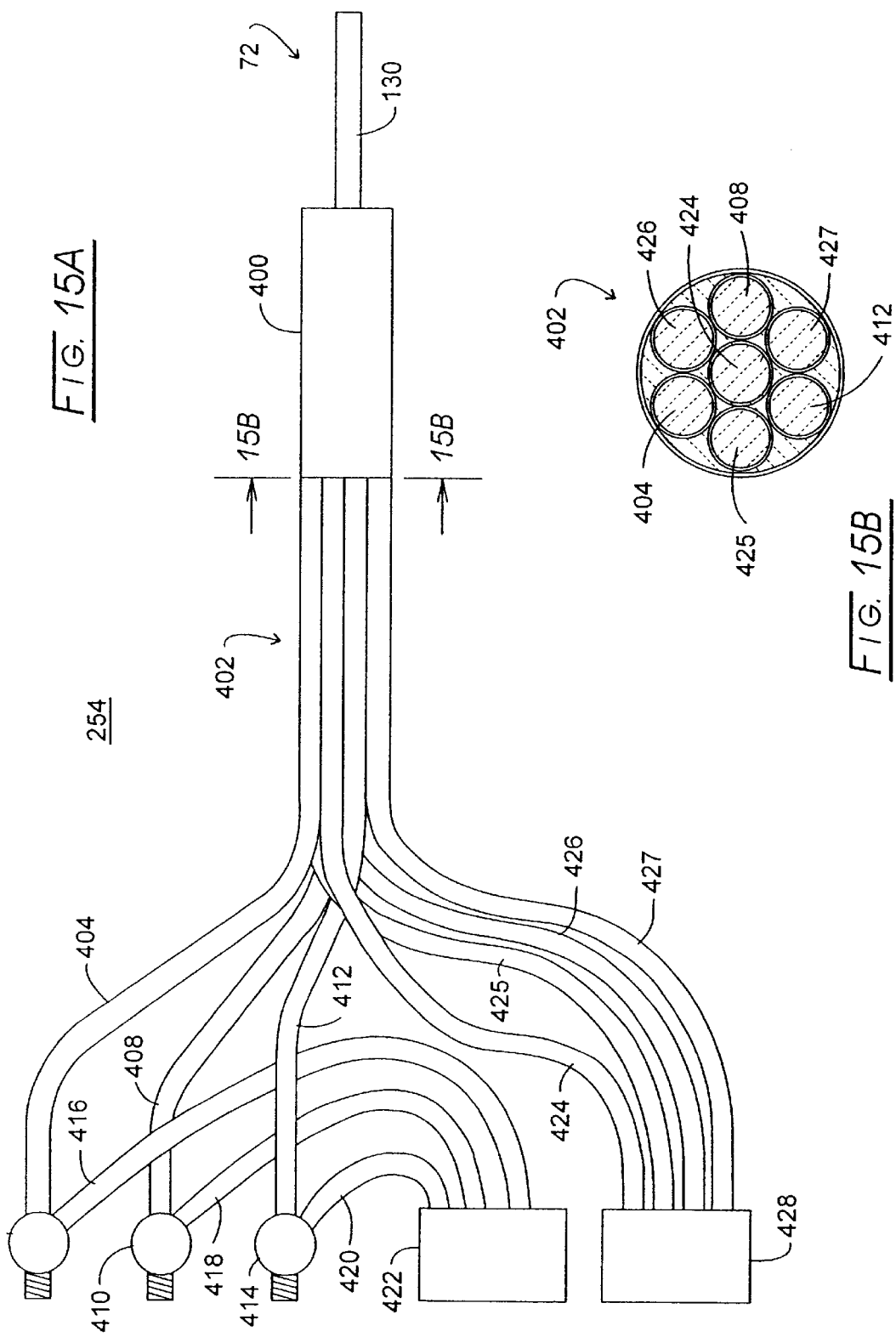
FIG. 15A is a schematic representation of optical components performing with a sensor according to the invention.
FIG. 15B is a sectional view taken through the plane 15B–15D shown in FIG. 15A.

Referring to FIGS. 15A and 15B, the light source and transducing function described that at 132 in FIG. 5, representing a component of the signal treatment system of the invention is revealed in more detail. This light source and transducing function also may be utilized for the function of that figure represented at block 138 as employed for carrying out pH analysis. The particular assembly disclosed may be utilized with the colorimetric approach to ammoniacal component evaluation wherein the reactor is a component-sensitive dye, for example, being sensitive to ammonia ($NH_3$). In FIG. 15A, the fiberoptic connector 72 described in conjunction with FIGS. 4 and 5 and, in particular, incorporating the transmission component 130 described in the latter figure is seen extending to a step-down chamber 400. Through utilization of this chamber 400, a singular fiberoptic strand or assembly 130 is positioned in light exchange relationship with an assemblage of seven fiberoptic components or channels represented generally at 402. The discrete fiberoptic components of the assemblage 402 include: a fiberoptic component 404 which transmits light at a wavelength, for example, of 450 nm from an LED source 406; a transmitting fiberoptic component or strand 408 which transmits light at a wavelength, for example, of 615 nm from an LED source 410; and a fiberoptic strand or component 412 which carries light, for example at a wavelength of 700 nm from an LED source 414. Reference fiberoptic components 416, 418 and 420 transmit light from respective sources 406, 410 and 414 to a photodiode reference function represented at block 422. Light returning from impingement upon the ammoniacal component sensitive dye is collected or gathered and transmitted by core gathering fiberoptic components 424–427. Optical components 424–427 are directed to a combining input at a photodiode sensor represented at block 428.

Looking to FIG. 15B, a cross-section of the assemblage 402 is provided. The gathering component 424 is seen centrally disposed within the assemblage 402, while remaining gathering components 425–427 are disposed symmetrically about it. Transmitting fiberoptic components 404, 408 and 412 have the same diameters and are seen to be symmetrically disposed about the centrally located collecting component 424. With this arrangement, about 11% of the source light from sources 406, 410 and 414 is transmitted to the associated reactor and about 44% of the light reflected from the reactor is transmitted to the photodiode detector 428.

Figure 16:
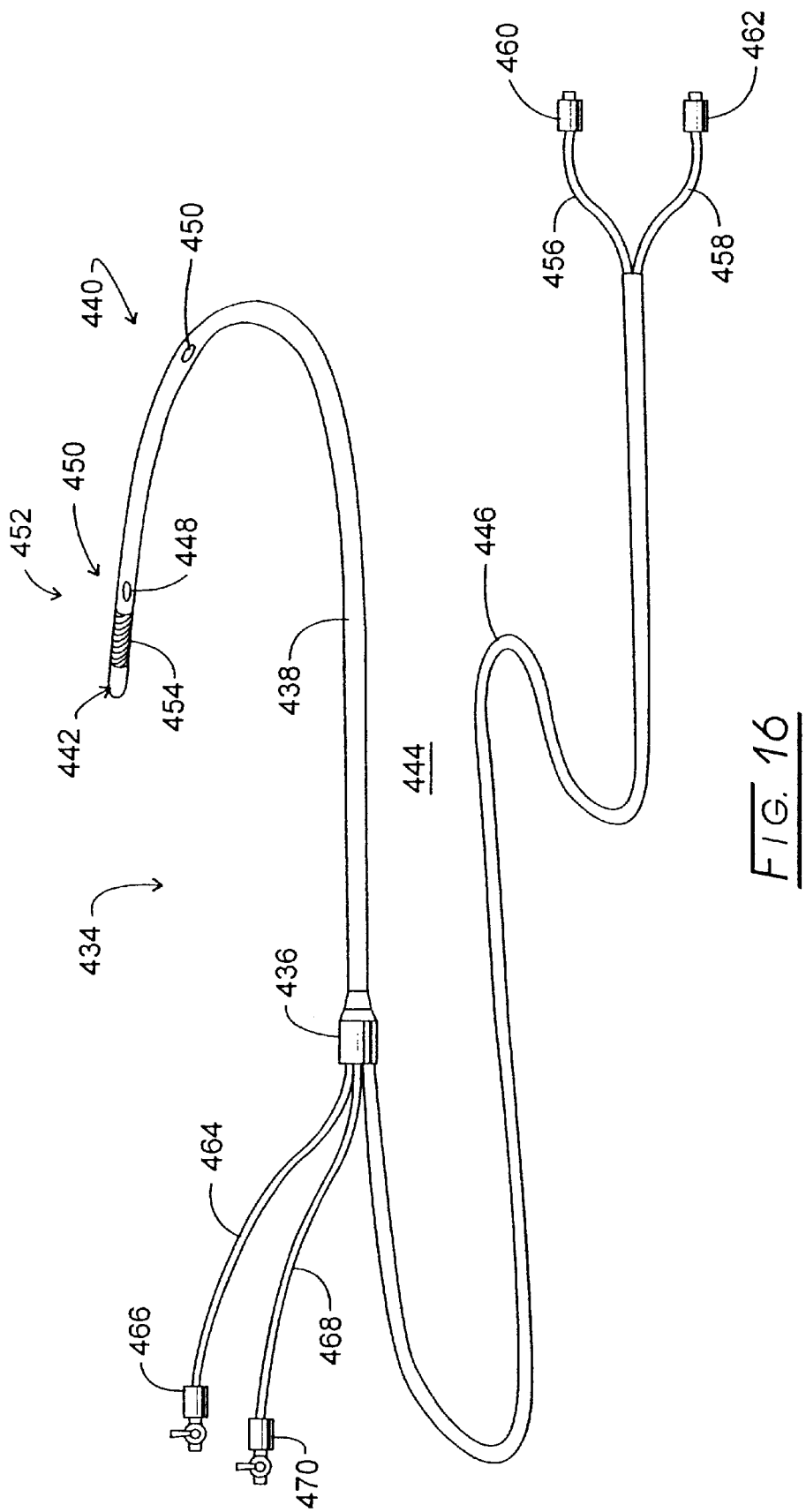
FIG. 16 is a pictorial view of a catheter incorporating a concentration sensor with non-optical technology.

Ammoniacal concentration monitoring systems may be configured using technologies other than those which are optically based. Where such alternate approaches are utilized, some modification of the design of a catheter-based embodiment is undertaken. Referring to FIG. 16, a catheter is shown at 434 being structured with a concentration sensor which is non-optical in design. Catheter 434 may employ a variety of ammoniacal concentration sensor technologies, for example, sensors based on amperometry and voltometry as well as Schottky diode-based technologies and acoustic-wave based technologies. Catheter 434 includes a base component 436 from which extends a catheter body 438 configured for positioning within a vessel of a vascular system. Body 438 incorporates a measurement region 440 which extends to a tip 442. Base 436 is located within a proximal region represented generally at 444 which includes a communication cable 446. Spaced rearwardly from the tip 442 is a distal auxiliary port 448 and, still further rearwardly positioned is a second or proximal auxiliary port 450. Ports 448 and 450 are optional within the catheter 434 and may be employed for deriving, for example, blood samples, introducing medicants or the like. The forward assembly of the ammoniacal concentration component sensor is represented generally at 452 within the measurement region 440 and preferably is located adjacent tip 442. For most implementations of this form of forward assembly 452, a membrane of the nature discussed above is employed. Catheter 434 is dimensioned having a principal cross-sectional dimension or outer diameter which is as minimal as practical to avoid blood hydraulic impedance phenomena. A membrane 454 covers a sensor assembly adjacent the tip 442. This sensor assembly is electrically associated with the proximal region 444 via cable 446 and is seen to extend to electrical leads 456 and 458 terminating, in turn, at respective electrical connectors 460 and 462. Communication with auxiliary port distal 448 is provided by a channel extending through the body portion 438 to base 436. From that location, a flexible conduit 464 is seen to extend to a connector and valve assembly 466. In similar fashion, the proximal port 450 is in fluid communication with a channel extending through the body portion 438 to base 436. At base 436, this channel is coupled in fluid transfer communication with a flexible conduit 468 extending to a connector and valve assembly 470.

Referring to FIGS. 17 and 18, the structure of catheter 434 at its forward assembly 452 is revealed. At forward assembly 452, the polymeric body portion 438 is configured of reduced diameter to accommodate for the sensor structure associated with the earlier described membrane 454. FIG. 18 reveals this reduced cylindrical outer diametric surface 480 which additionally is configured to form three channels or lumens 482, 483 and 484. Channel 483 is revealed in FIG. 18. Channels 482 and 483 communicate with respective auxiliary ports 448 and 450. These channels are plugged with a cylindrically-shaped tip plug 486 forming the outer tip 442 of catheter 434. The ammoniacal component sensor is represented generally at 488 and, being formed in conjunction with membrane 454, is structured as an ion-specific electrode-based device. Membrane 454 is provided as a microporus, hydrophobic polymer such as the earlier described Teflon or polytetrafluoroethylene. Membrane 454 is semi-permeable to the ion of interest, in the present embodiment that ion is the ammonium ion ($NH_4^+$). FIG. 18 reveals that the cylindrical body surface 480 at the sensor assembly 488 forms the inner wall of an electrolyte retaining chamber or gap 490, the outer wall of that gap or chamber 490 being the membrane 454. Within the gap 490 is an electrolyte or electrically conducting liquid 492. Where the sensor 488 is configured for detecting the noted ammonium ion component, the electrolyte liquid 492 may be a solution containing, for example, 0.1 molar ammonium chloride. That liquid 492 reaches equilibrium with blood carried ammonium ion flow across the membrane 454 to change or alter the pH of the solution or liquid 492. For the ammonium ion component, the higher the concentration of ammonium ion in the blood stream passing over the membrane 454, a corresponding effect will be observed in the ammonium ion concentration in liquid 492. Ion selective electrodes are employed to measure this ion concentration within liquid 492. In this regard, the cylindrical surface 480 is coated at the forward assembly 452 with a pH electrode which may be implemented as a glass electrode selective to the hydrogen ion. Such an electrode is shown at 494. Electrode 494 may be a glass comprising silicon dioxide, lithium oxide and calcium oxide in the ratio 68:25:7. Note in FIG. 17 that electrode 494 extends from an annular shoulder 496 formed in body portion 438 adjacent tip 442 to an edge or termination at 590, and is connected to an electrical lead 502 extending within channel 484. A cylindrically-shaped reference electrode 504 completes the forward assembly 452. This second electrode 504 may be provided as a metallic coating, for example, silver/silver chloride. Electrode 504 is spaced from the glass electrode 494 but remains operationally associated therewith within the electrolyte containing cavity or gap 490. Electrode 504 is connected to a lead 506 which also extends through the channel 484. Sensor 488 may perform in either a potentiometric mode wherein voltage across the reference and glass electrodes is determined, or may operate in an amperometric mode wherein the current flow between these two electrodes is evaluated during the application of a d.c. voltage difference.

Referring to FIGS. 19 and 20, sections of the catheter 434 adjacent the proximal auxiliary port 450 are revealed. In the figure, catheter body portion 438 is seen to have an enlarged diameter as compared with its diametric extent at the sensor 488. FIG. 19 reveals auxiliary channel or lumen 483 as it extends to the port 450. In this regard, while the channel 483 extends essentially the length of the catheter 434, fluid is restricted to outflow from the port 450 by a plug 508 just forward of the port. FIG. 20 reveals the electrical leads 502 and 506 extending within the electrical lead channel 484. These leads become a component of the cable 446 at base 436 and further evolve as the leads 456 and 458 leading to respective connectors 460 and 462 (FIG. 16).

Now looking to the utilization of Schottky diode-based ammoniacal sensor assemblies, reference is made to FIGS. 21–23. In these figures, the sensor assembly is represented in schematic fashion. Looking to FIG. 21, the measurement region 516 of a catheter 518 of a variety described in connection with FIGS. 4 and 16 is seen to incorporate a front end assembly 520 which employs the technology based upon the interaction of planar Schottky barrier diodes with an ammoniacal component. In this embodiment, the sensor assembly 520 is mounted upon, for example, a wall 522. Sensor 520 is formed having two metal electrodes configured in spaced relationship and in an interdigitated geometry. These electrodes are provided as a gold electrode 524 configured in conjunction with an aluminum electrode 526. Gold electrode 524 creates an ohmic contact and aluminum electrode 526 creates a Schottky barrier contact with a conducting polymer layer 528. For example, a p-doped semiconductor such as P3OT may be employed (poly (3-Octylthiophene)). The conducting polymer 528 exhibits an electrical conductivity which is correlatable with the concentration of the ammoniacal component at hand. The conducting polymer employed may be substituted polypyrroles, polythiothenes, or polyanillianes. Not shown in the drawings is an ammoniacal component permeable membrane as discussed earlier herein which covers the active sensor components. As before, the outer surface of such a membrane is in contact with flowing blood of the bloodstream. See generally:

Assadi, A et al., Interaction of Planar Polymer Schottky Barrier Diodes with Gaseous Substances", Sensors and Actuators, Vol 20, pp 71–77 (1994).

Now considering ammoniacal component sensors which are acoustic wave-based, reference is made to FIG. 24. In the figure, the sensor forward assembly as it would be mounted in the manner of the sensor of FIGS. 21–23 is depicted schematically at 530. The sensing principle of such acoustic sensors is based upon the detection of changes of wave velocity and attenuation caused by perturbations at the surface of the material in which the wave propagates. If an acoustic wave delay line is placed in an oscillator loop as the frequency-determining element, velocity shift causes a shift in the delay time of the wave. This results in a shift of the oscillation frequency. In the figure, an interdigitated transmission transducer is shown at 532 spaced from a reception transducer 534. Sound reflectance from the ammoniacal component being investigated is represented by the arrow 536. Transducers 532 and 534 are connected in a delay line oscillator circuit. The latter circuit includes an oscillator amplifier 538 having an input at line, 540 and an output at line 542. Transducers 532 and 534 are incorporated within a feedback path or delay line, transducer 532 being coupled via lines 544 and 546 to line 542 and transducer 534 being coupled via lines 548 and 550 to line 540. Accordingly, the output of the amplifier 538 is fed back by the delay line incorporating the transducers where $A(\omega)$ represents amplifier gain and $B(\omega)$ represents delay line losses. The transducers as well as the oscillator circuit may be multi-layer devices constructed using conventional integrated circuit manufacturing methods employing silicon, (base) silicon dioxide, aluminum, and zinc oxide (surface). See generally the following publication:

Velekoop, et al., "Integrated-Circuit-Compatible Design and Technology of Acoustic-Wave-Based Microsensors", Sensors and Actuators, Vol 44, pp 249–263 (1994)

In the practice of accessing the vessels of the vascular system to carry out ammoniacal component monitoring according to the invention, a variety of vessel sizes and vessel conditions will be encountered by the practitioner. In this regard, a catheter of conventional diametric extent may evoke a hydraulic impedance in the vessel carrying blood to the extent that the vascular system may divert the bloodflow or bloodstream to a branch vessel. Further in this regard, particularly where infants such as neonates are the subject of ammoniacal component monitoring, the vessels themselves may be so small as to call for a catheter structure of very minimal principal cross-sectional dimension, for example, exhibiting a diameter in a range of about 0.010 inch to 0.060 inch. In this regard, a catheter can be developed which is quite similar to a hypodermic needle wherein the central channel supports a singular fiberoptic strand to carry out monitoring. Where the ammoniacal component is gaseous ammonia, two such catheters may be employed, one to measure pH and the other to measure the component ammonia gas, the forward end assemblies of such optical devices being structured in the manner described above, for example, in connection with FIGS. 13 and 14. Looking to FIGS. 25 and 26, a catheter structure of such minimized shaft diameter is revealed generally at 560. Catheter 560 includes a rigid shaft 562 extending from a base shown generally at 564 to a pointed tip 566. Configured in similar fashion as a hypodermic needle, the shaft 562 incorporates a cylindrical channel 568 as defined by its inner, curved surface 570 (FIG. 26). Base 564 includes a cap-shaped cylindrical hub 572 the internal cavity 574 of which is enclosed by a cover member 576. Member 576 includes a circular opening 578 which extends to an aligned circular opening within a sealing gland or seal 580. Seal 580 may be formed of silicone rubber. Extending through the assembly is a fiberoptic strand 582, the forward tip 584 of which is covered with a membrane-based reactor structure 586 which is configured as described in connection with the above-noted figures. Catheters as at 560 may have overall lengths within a range of about 1.0 inch to 6.0 inch and perform with fiberoptic strands of diameter within a range of about 0.005 inch to 0.040 inch.

Figure 27:
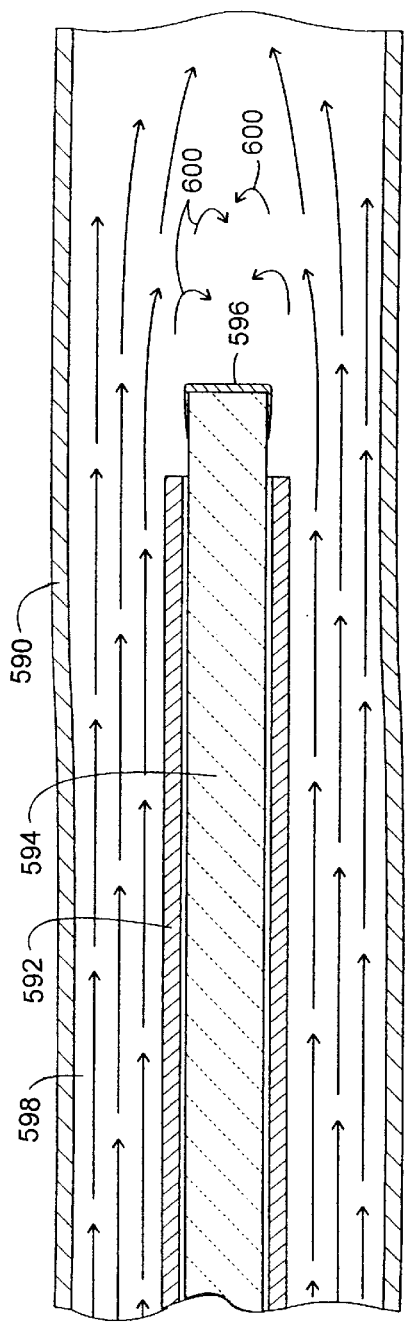
FIG. 27 is a schematic sectional view of a vessel in which a catheter has been inserted.
Figure 28:
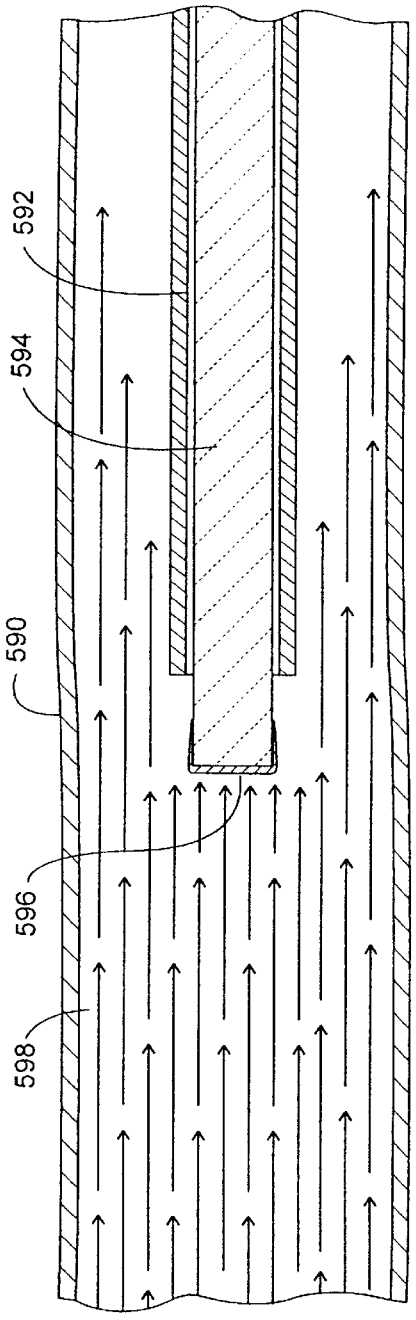
FIG. 28 is an other sectional view of a vessel within which a catheter has been inserted.

Animal testing carried out in conjunction with fiberoptic-based catheters according to the invention have shown that improved sensor response is achieved where the catheter is inserted within a vessel of the vascular system in a manner wherein the sensing tip employed with fiberoptic-types of sensors, be in a confrontational orientation with respect to bloodflow. Where the tip of such catheter sensor structures is located within a blood carrying vessel in a manner wherein blood passes over it from what may be considered a rearward location, the surface of the sensors will encounter a more or less quiescent or back flowing blood. Looking to FIG. 27, the wall of a vessel such as an artery is shown at 590. Within the interior of the vessel wall 590 there is schematically illustrated a catheter 592 incorporating a fiberoptic strand 594 having a sensing assembly 596 at its tip. Bloodstream flow is represented in the drawing by the arrows as at 598 and 600. Note that the bloodflow arrows at 600 adjacent the sensor 596 illustrate the noted quiescent or back flow association with sensor 596. Where such an arrangement is at hand, the interval required to derive a sensor output is more extended than when the catheter is positioned in a confronting orientation with respect to bloodflow. Such an orientation is revealed in FIG. 28. In the figure, catheter 592 reappears with tip 596 in a confrontational orientation with respect to the flow of the bloodstream as represented at arrows 598. Note that in the vicinity of the sensor 596, the blood directly confronts the surface of the sensor. With such an orientation for the catheter 592, the response time for achieving a readout from sensor 596 is substantially improved.

Figure 29:
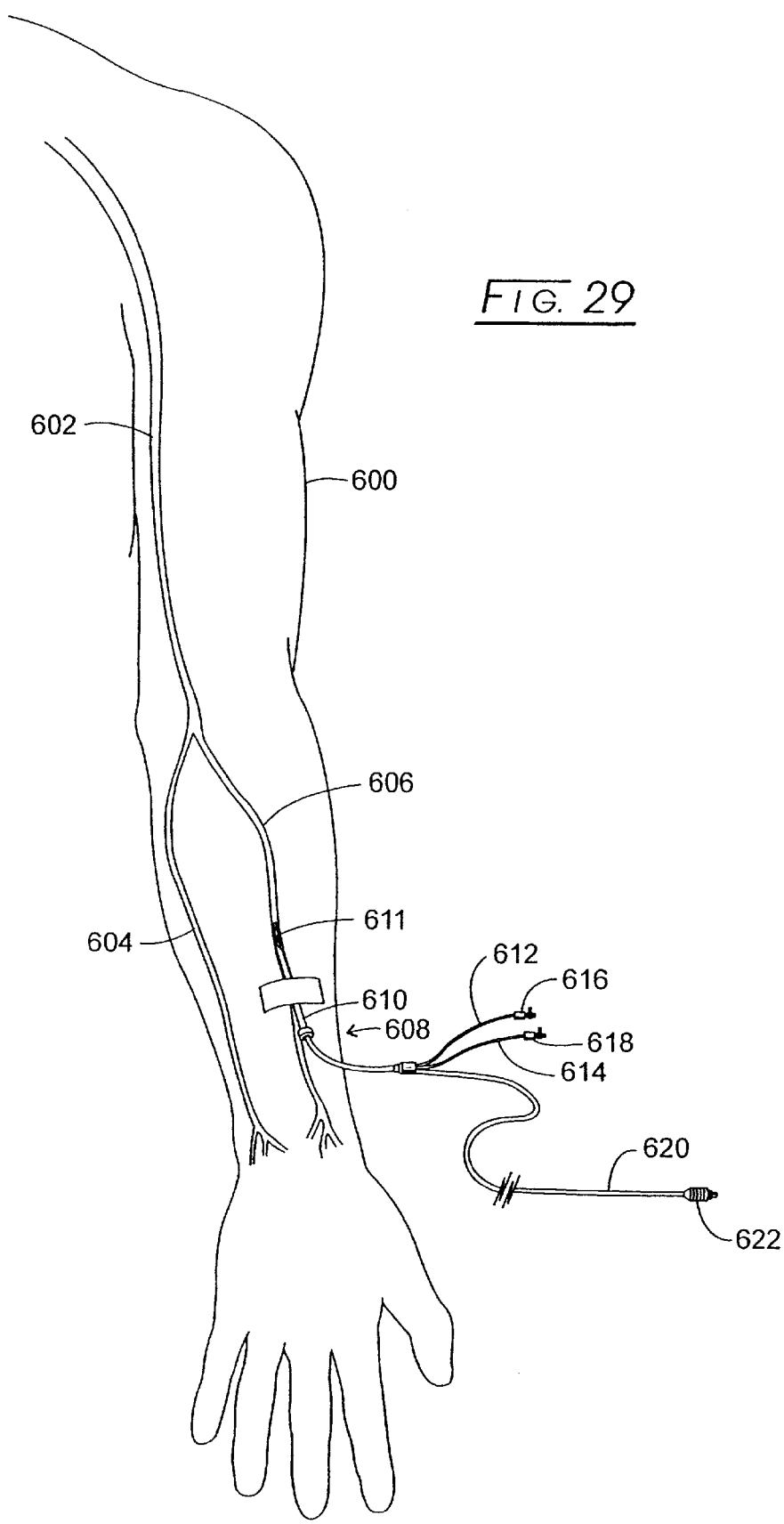
FIG. 29 is a pictorial representation of a human arm with a catheter insertion according to the invention.
Figure 30:
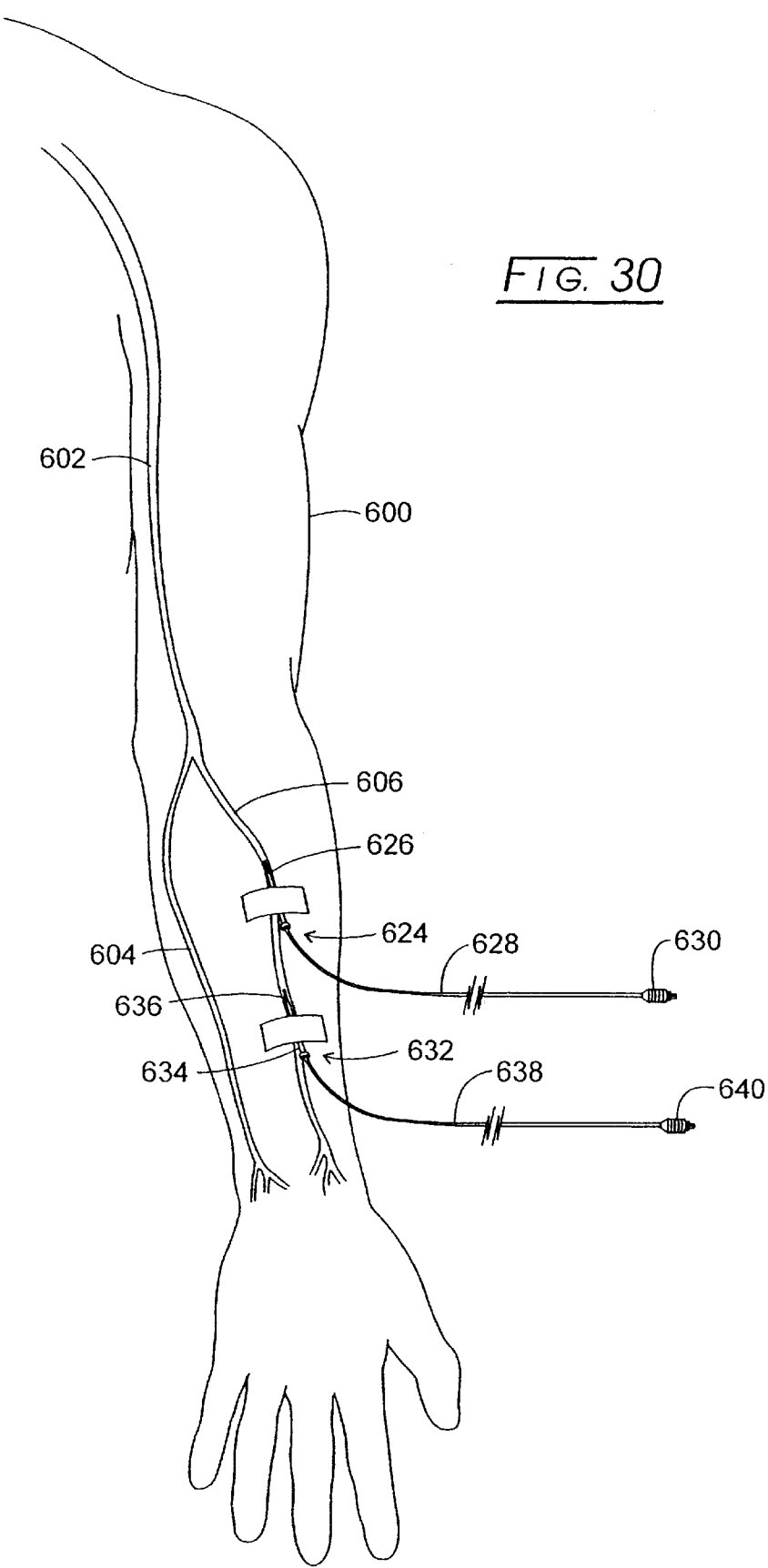
FIG. 30 is a pictorial representation of a human arm with the insertion of a pair of catheters of minimal dimension according to the invention.

In a typical application, the ammoniacal concentration monitoring according to the invention is carried out with catheters which preferably are located in a peripheral region of the vascular system of the body. The term "peripheral" as used herein is intended to refer to those portions of this vascular system which are beyond or without the region of the heart. While monitoring of neonates typically will be carried out with the noted catheters of minimal dimension and utilizing, for example, an umbilical vein or artery, the catheter utilization for normal adults will typically involve a peripherally located artery such as the brachial, radial or ulnar arteries, the latter two residing in the forearm. As noted above, where blood hydraulic impedance becomes problematic, the catheter may be extended from a branch artery, i.e., into the brachial artery. Looking at FIG. 29, arterial, in-line employment of a catheter assembly according to the invention is illustrated. In the figure, the brachial artery is represented at 602 branching to the ulnar artery at 604 and the radial artery at 606. A catheter assembly, for example, as described in conjunction with FIG. 4 is shown generally at 608 positioned within the radial artery 606. In this regard, the catheter is located within and extending from an introducer 610 which is positioned within the artery 606. The catheter assembly measurement region 611 extends from the introducer 610 within the artery 606 in an orientation confronting the direction of bloodflow as above discussed. Auxiliary channels of the catheter assembly 608 extend to conduits 612 and 614 terminating in respective connector and valve assemblies 616 and 618. The fiberoptic components of the catheter assembly 608 are seen to extend via a cable 620 to an optical connector 622. Catheter assembly 608 will incorporate, for example, both a pH sensing channel and an ammonia gas sensing channel. Where blood flow in the radial artery 606 may encounter excessive impedance evoked by the presence of the introducer 610 and catheter assembly 608, the vascular system or body may react to evoke a hydraulic diversion toward the ulnar artery 604. For such conditions, minimally dimensioned catheter structures as described in connection with FIGS. 25 and 26 may be employed. Alternatively, measurement region 611 may be inserted until it resides in brachial artery 602 which avoids blood hydraulic diversion in the parallel bronches represented by the radial and ulnar arteries. Looking to FIG. 30, the arm 600 again is reproduced with the earlier identifying vascular system vessel numerical identification as in FIG. 29. A minimally sized catheter assembly 624 is shown inserted within the radial artery 606 without utilization of an introducer (e.g., through the utilization of what, in effect, is a hypodermic needle as shown in FIG. 25), the sensor component being located at its tip 626 positioned within the artery 606. The catheter assembly 624 will be of a single channel variety in keeping with its minimization of size and will provide an output from its sensor at fiber cable 628 which terminates in an optical connector 630. Positioned downstream within the radial artery 606 is another catheter assembly 632 which, as in the case of assembly 624 is positioned within the artery 606 without utilization of an introducer, the hypodermic needle-shaped catheter body being represented at 634 extending to a sensor supporting tip 636. The single channel optical output is directed along cable 638 which is seen to extend to an optical connector 640. With the arrangement shown, where the ammoniacal component monitored is ammonia gas, one of the catheter assemblies, for example that at 624, is utilized to derive a pH valuation, while the second catheter, for example that at assembly 632 is utilized to monitor the ammonia component.

Figure 31:
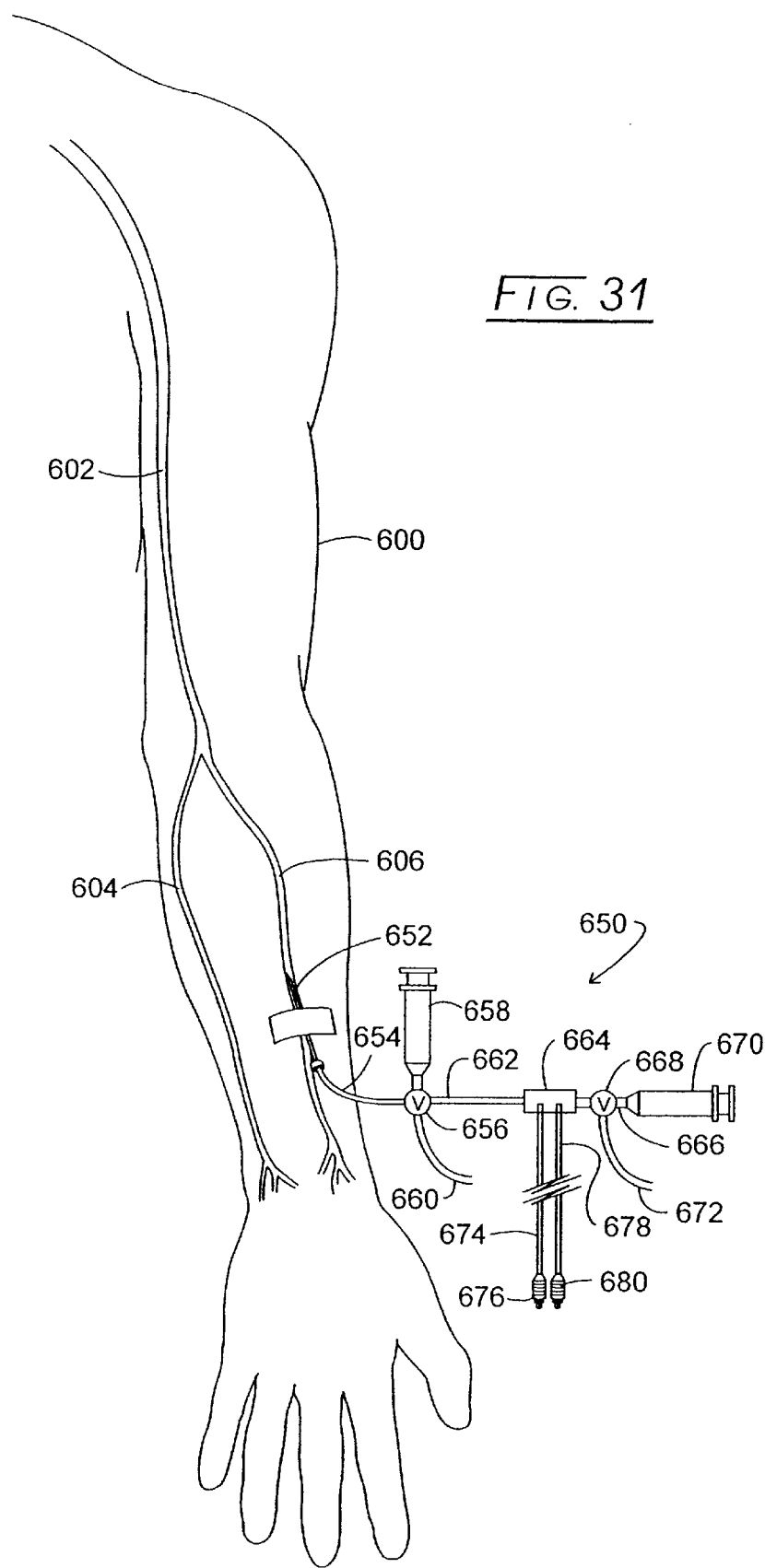
FIG. 31 is a pictorial representation of a human arm with a bypass sampling arrangement for carrying out the monitoring procedure of the invention.

The monitoring system and method of the invention also may be employed with sampling techniques wherein a catheter is not utilized. For example, the monitoring system and method may be carried out with a variety of blood bypassing systems or assemblies such as a hand actuated blood sample collecting system; a cardiac bypass system; or a hemodialysis system. Referring to FIG. 31, the former approach is illustrated. In the figure, arm 600 again is reproduced along with arterial vessels 602, 604 and 606. A blood bypass assembly is represented in general at 650. The bypass assembly includes a hypodermic needle or the like 652, which has been positioned such that its tip extends within the radial artery 606. A conduit 654 extends to a valve represented at symbol 656 which is coupled to a hypodermic syringe 658 utilized for flushing purposes in conjunction with a flushing fluid input at conduit 660. Valve 656 additionally is coupled to conduit 662 which extends to a sampling chamber 664. From the chamber 664, a conduit 666 incorporating a valve 668 extends to a sampling syringe or pump 670. A flushing drain conduit 672 is coupled to valve 668. Sampling chamber 664 is accessed, for the instant embodiment, by a fiberoptic based pH sensor having an output cable 674 extending to an optical connector 676. Also communicating with the sampling chamber 674 is a fiberoptic based ammonia sensor having an output cable 678 extending to an optical connector 680. For the arrangement at hand, the syringe 670 is actuated by the practitioner to draw a sample of blood into sampling chamber 664. As the blood enters chamber 664 it is monitored for ammonia concentration and pH level and the resultant values are submitted to a controller (not shown) via connectors 676 and 680. Following monitoring, the syringe 670 again may be actuated to return the sample of blood to the radial artery 606 via the hypodermic needle 652. It may be desirable from time to time to flush such bypass systems. For such an arrangement, the syringe 658 withdraws a quantity of flushing liquid from conduit 660 with appropriate manipulation of valve 656 to cut off fluid communication with conduit 654. The syringe 658 then is actuated to pump the flushing liquid through conduit 662 and sampling chamber 664. Valve 668 is manipulated such that the flushing liquid will drain through conduit 672 and the input to pumping syringe 670 is blocked.

Figure 32:
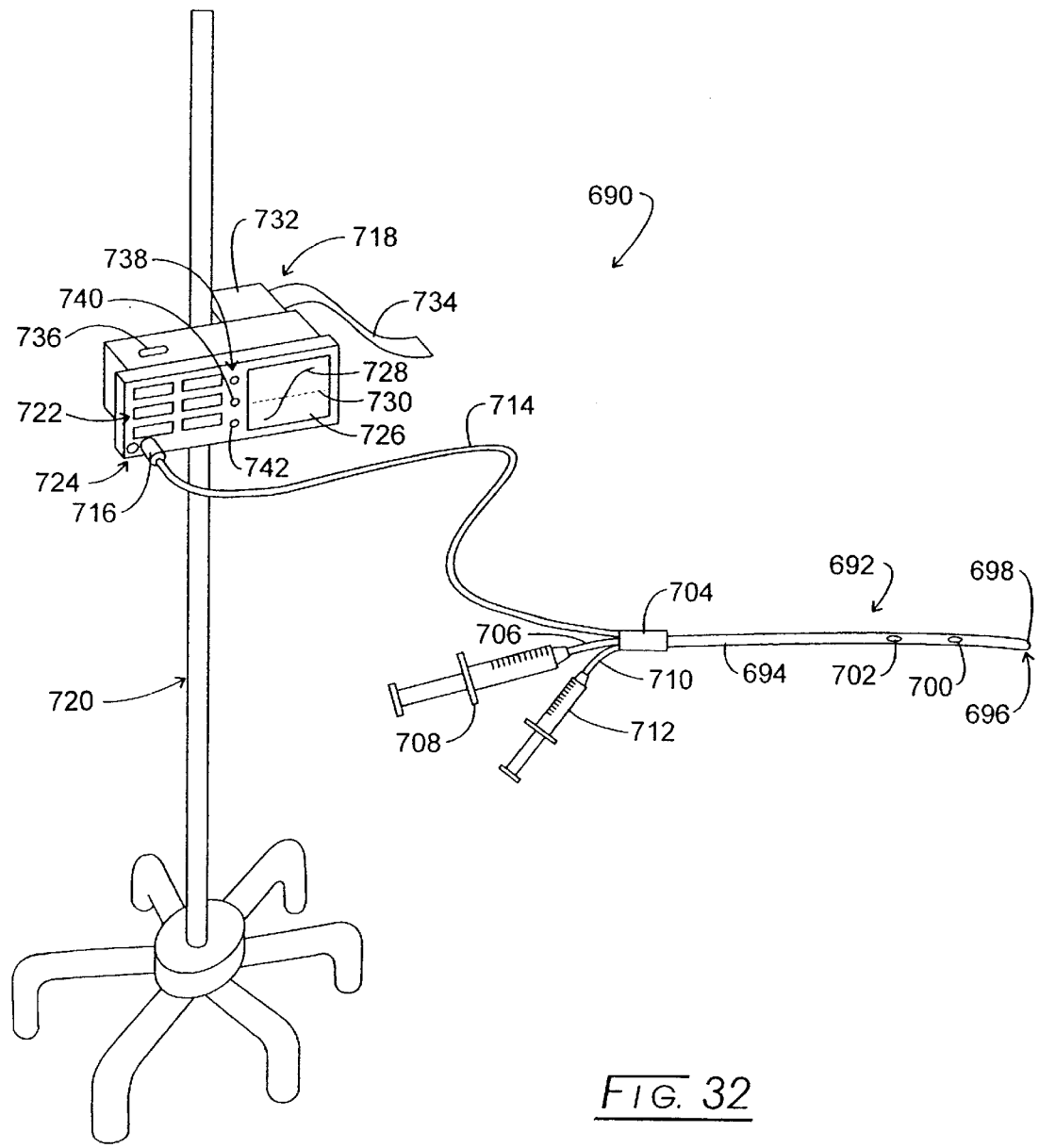
FIG. 32 is a pictorial representation of a system according to the invention.

A pictorial representation of the overall system of the invention for monitoring ammoniacal concentration is presented in FIG. 32. In the figure, the system, represented generally at 690, includes a monitoring catheter assembly represented generally at 692 which is seen having a cylindrical body portion 694 and a measurement region 696 extending to a tip 698. Auxiliary ports 700 and 702 are provided with the assembly 692 for the purpose of withdrawing samples for blood assays or introducing medicants or the like. The catheter body 694 extends to a base 704 having a conduit 706 communicating with distal auxiliary port 700 and a hypodermic syringe 708. Similarly, a conduit 710 extends from base 704 and is in fluid transfer communication with distal auxiliary port 702 and a syringe 712. Monitoring readouts from a fiberoptic based ammonia sensor and a fiberoptic based pH sensor are conveyed via an elongate cable 714 and optical connector 716 to an appropriate input of a controller represented generally at 718. Controller 718 is mounted upon a conventional IV pole or stand represented generally at 720. The controller 718 includes an array of keys represented generally at 722 which are utilized for entering or inputting control parameters such as the type of sensor utilized, total ammoniacal concentration level threshold; real time information; total ammoniacal concentration rate-of-rise threshold and pH value where no sensor is employed for that measurement. Below the key array 722 is an array of connectors represented generally at 724 which may provide for a separate pH signal input, a dual pH and ammoniacal component sensor input as provided from connector 716; amprometric, potentiametric and acoustic system inputs as derived from the particular sensing system employed. A display is shown at 726 having a total ammoniacal content (trend) readout with respect to real time as shown at 728. Displayed with the graphics or curve 728 is a threshold level visual cue 730. A permanent record may be printed with the system via a printing assembly 732 providing a strip-type paper readout 734. A serial input/output port 736 is mounted upon the upper surface of the controller 718. The controller 718 also may supply aural cues to the practitioner indicating an alarm condition. Visual cuing is provided, for example, by light emitting diodes (LEDs) three of which are shown at 738, 740 and 742. Diode 738 may be, for example, of an amber or yellow color indicating a warning that total ammoniacal concentration is rising from one display interval to the next. Diode 740 provides a red coloration output to indicate an alarm condition such as the meeting or exceeding of an inputted threshold value. Diode 742 provides a visual output, for example, in the red color of the spectrum where the rate of rise of total ammoniacal concentration exceeds a rate-of-rise threshold.

Figure 33:
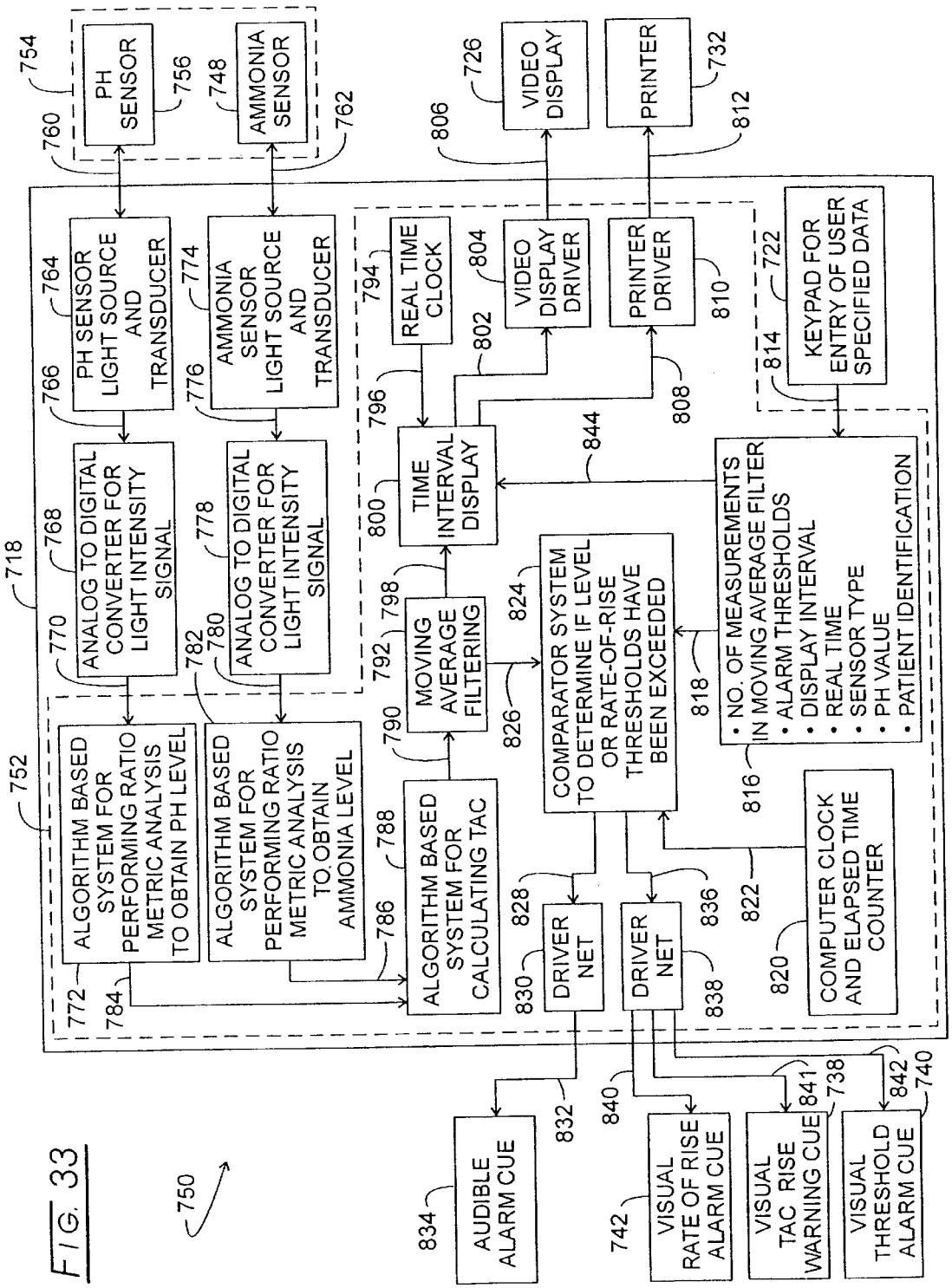
FIG. 33 is a block schematic diagram of the controller arrangement of the invention.
Figure 34A:
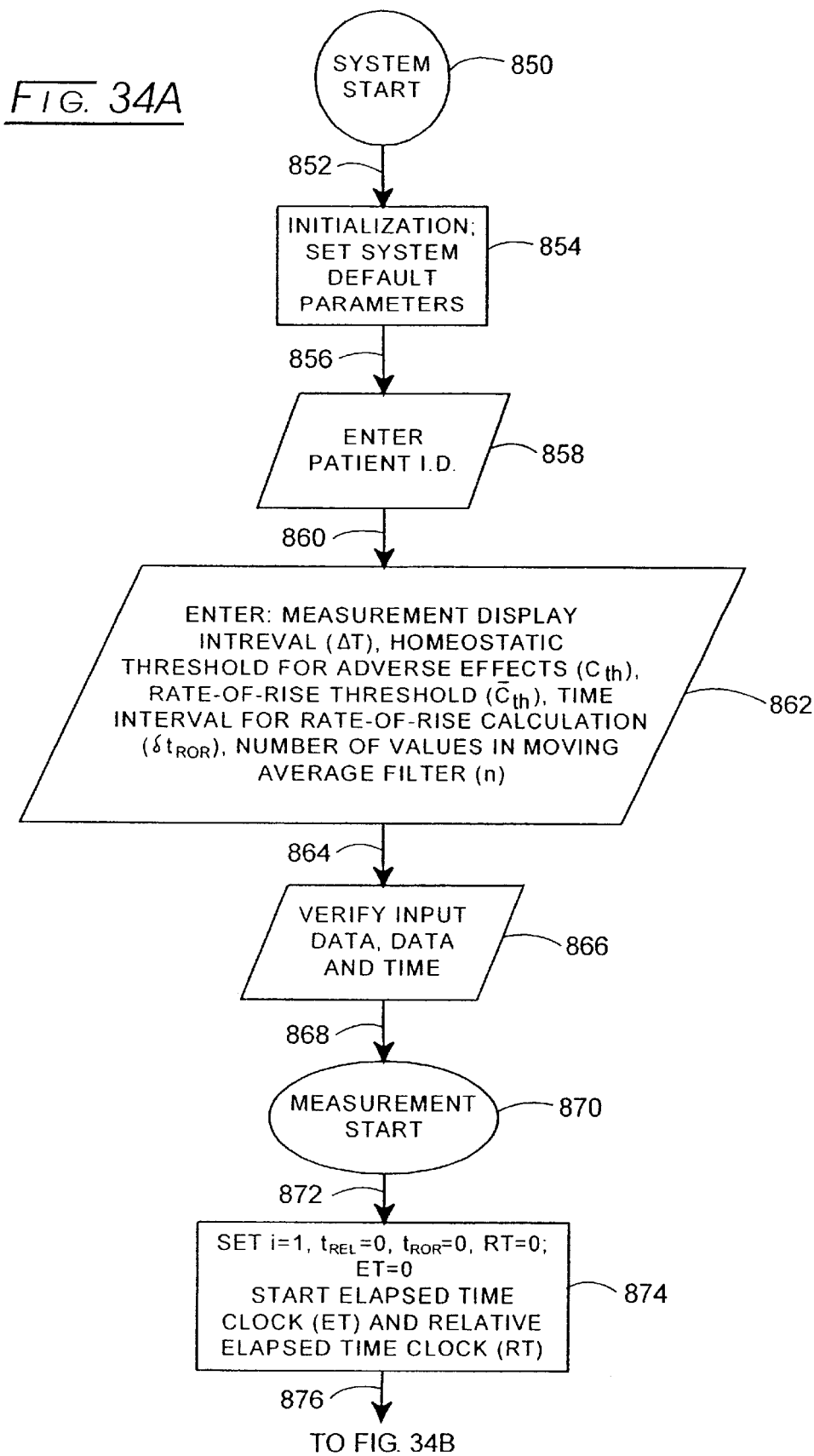
FIGS. 34A–34E combine as labeled thereon to provide a flow chart describing the operation of a controller employed with the invention.
Figure 34B:
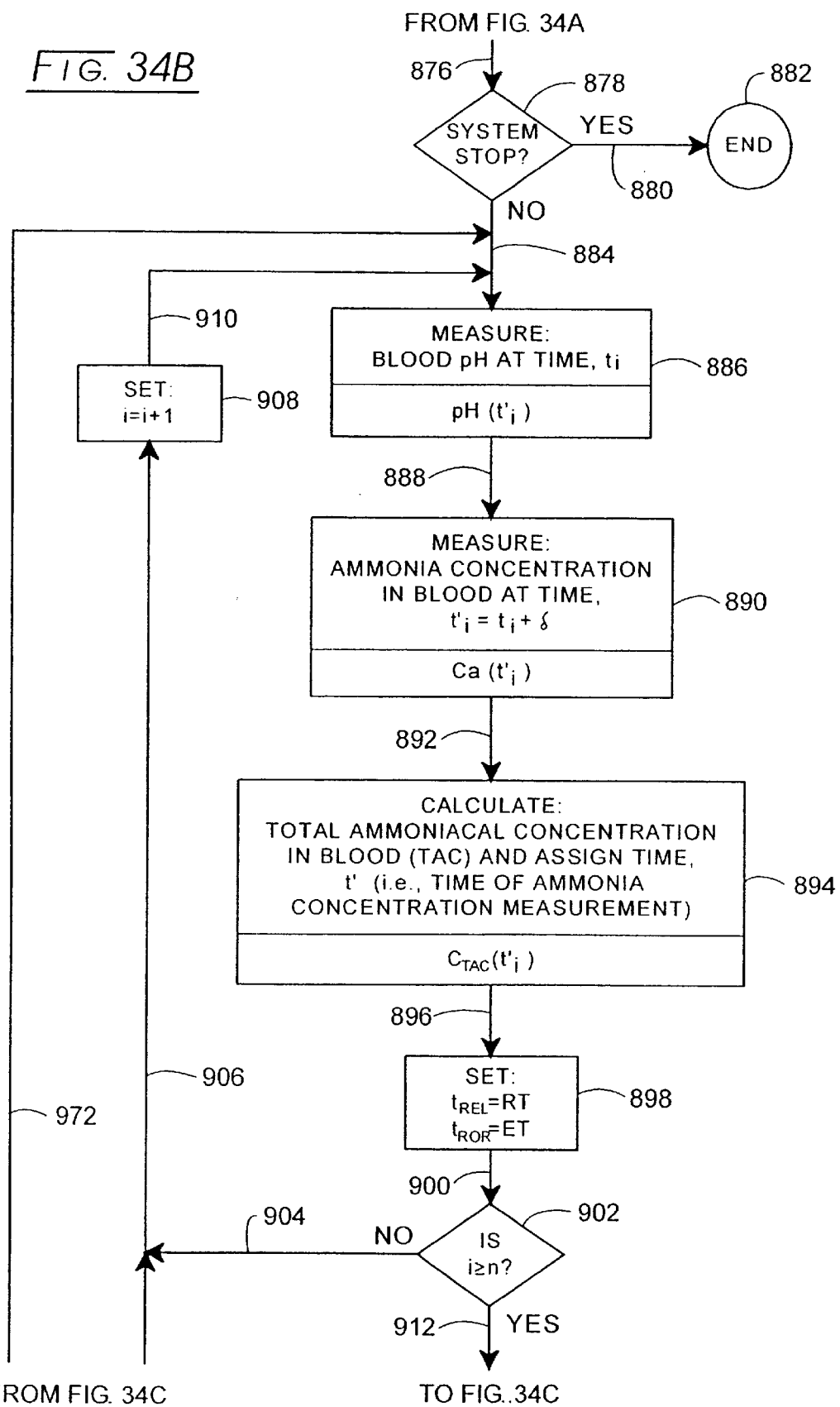
Figure 34C:
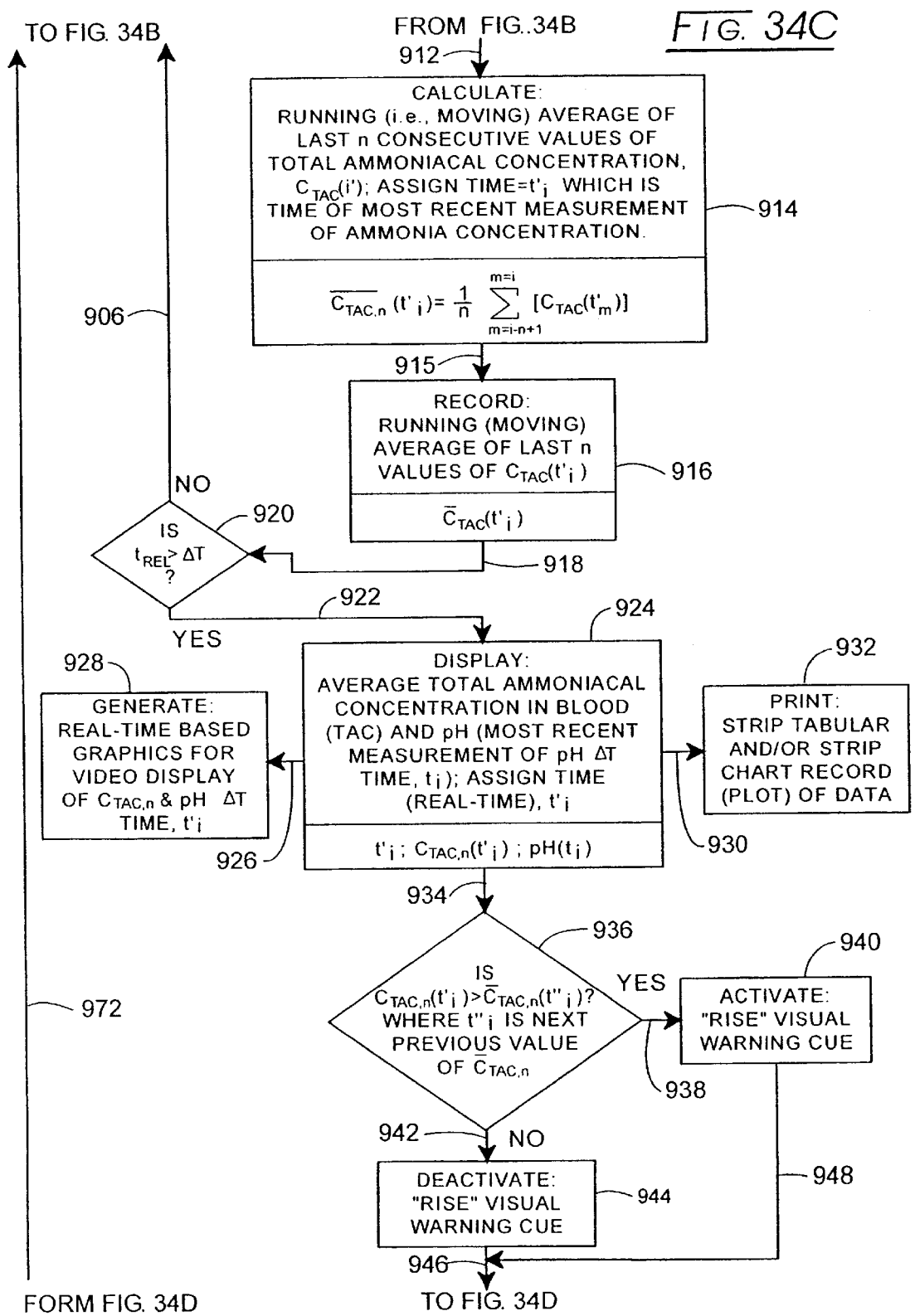
Figure 34D:
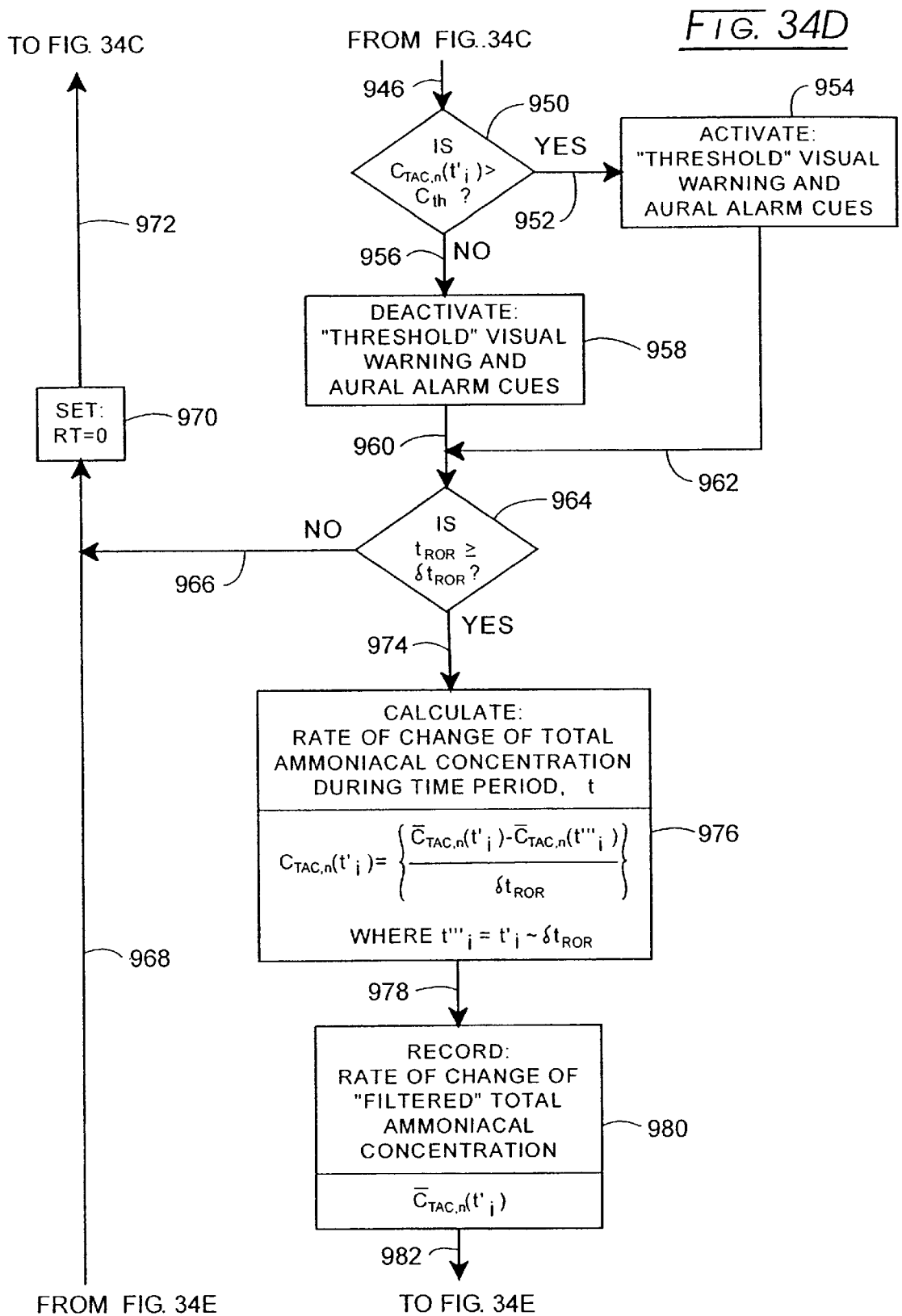
Figure 34E:
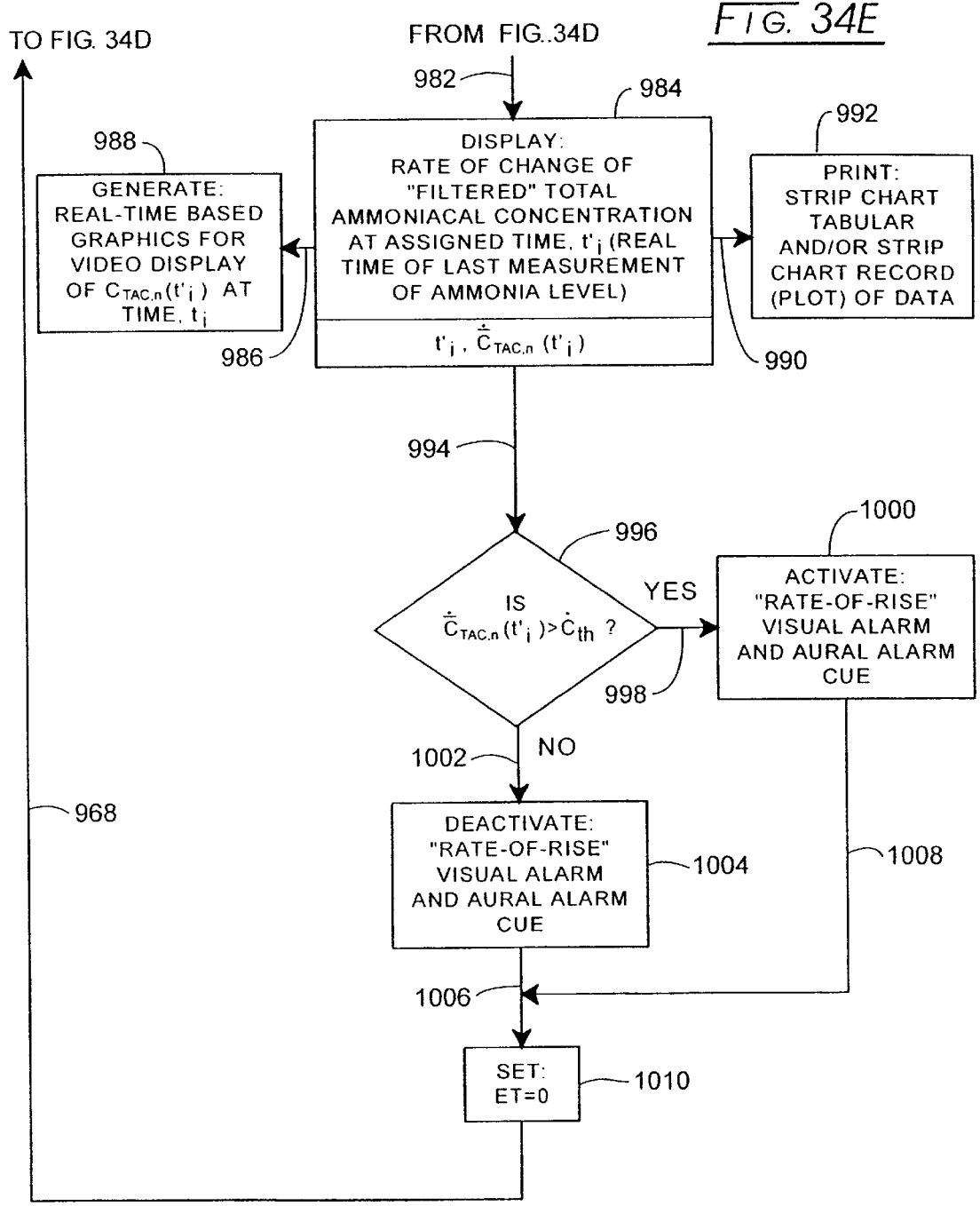

Referring to FIG. 33, a block diagram is provided illustrating the overall system 750 of the invention. In the figure, the controller function again is identified at 718 and now represented by a boundary. Video display 726 is represented symbolically, printer 732 is represented symbolically and the LED warning and alarm outputs again are represented with the same numeration at blocks 738, 740 and 742. Controller 718 is microprocessor driven and the microprocessing or software functions of it are represented within a dashed boundary 752.

FIG. 33 is configured in accordance with the preferred arrangement of the invention wherein the ammoniacal component monitored is ammonia gas (NH$_3$), an election which further requires the value of pH of the blood. Preferably, this pH value is monitored within the vascular system of the body in adjacency with the ammonia monitoring function. Recall that the embodiment of FIG. 4 provides a catheter with each such parameter being monitored within distinct channels of the instrument. The bloodstream of the patient is represented in the drawing within dashed boundary 754, a pH sensor function being represented at block 756 and an ammonia sensor being represented at block 748. A fiberoptic based approach is preferred for these sensing functions and the fiberoptic interaction for the functions at blocks 756 and 748 is represented by dual directional arrows shown respectively at 760 and 762. The fiberoptic input represented at arrow 760 is directed to a pH sensor light source and transducer function as represented at block 764. The pH related analog signal evoked from this function at block 764 is directed as represented at arrow 766 to an analog-to-digital conversion function represented at block 768. The resultant digitized pH value then, as represented at arrow 770 is introduced to the microprocessor function 752 and a software program under processor control carries out a ratiometric analysis to obtain pH level as represented at block 772.

Correspondingly, the ammonia sensor function 748 is implemented with an ammonia sensor light source and transducer function as represented at block 774. Light intensity related analog signals corresponding with ammonia concentration, then, as represented at arrow 776 are digitized as represented at block 778. Resultant digital signals, having been converted at the analog-to-digital function block 778 are then directed to the processing function as represented at arrow 780. Arrow 780 is seen to be directed to the software algorithm function represented at block 782 wherein a ratiometric analysis is carried out to obtain ammonia levels. The pH level or value and ammonia level concentration value, then, as represented at respective arrows 784 and 786 are directed to an algorithm-based system which functions to calculate total ammoniacal concentration.

Total ammoniacal concentration in blood may be computed by applying the well known Henderson-Hasselbalch equation with respect to the equilibrated ammonia gas-ammonium ion (NH$_3$)–(NH$_4^+$) system. See generally in this regard:

Hindfelt, D., "The Distribution of Ammonia Between Extracellular and Intracellular Compartments of the Rat Brain", Clinical Science and Molecular Medicine, Vol 48, pp 33–37, (1975).

The relative distribution of ammonia gas (NH$_3$) and ammonium ion (NH$_4^+$) in solution is given by that Henderson-Hasselbalch equation as follows:

$$pH = pK_a + \log \frac{[C_a(NH_3)]}{[C_a(NH_4^+)]} \quad (1)$$

This equation can be restated in terms of the unknown $C_a(NH_4^+)$ as follows:

$$C_a(NH_4^+) = C_a(NH_3)/[10 \exp(pH-pK_a)] \quad (2)$$

where $C_a(NH_4^+)$=concentration of ammonium ions (NH$_4^+$) in blood (micromole/liter)

$C_a(NH_3)$=measured concentration of ammonia gas (NH$_3$) in blood (micromole/liter)

pH=measured blood pH pKa=pH level of solution above which all ammonia exists as a gas (NH$_3$) where pKa=9.15 (Hindfelt, ibid).

The total ammonia content of the blood, $C_a$ (total) may be calculated as follows:

$$C_a(\text{total}) = C_a(NH_3) + C_a(NH_4^+) \quad (3)$$

The above computations are represented in FIG. 33 block 788. Once these total values are obtained on a regular measurement interval basis, the system carries out a moving average filtering as represented by arrow 790 and block 792. In this regard, in as much as the measurements of total ammoniacal concentration are carried out quite frequently with the system, an immediate display update of the numerical values or a graphical representation of those values may become distracting to the practitioner. Thus, the practitioner is afforded the opportunity of electing a number, n, of measurements which are compiled or queued in a first in, last out basis to provide a display both numerically and graphically which is "smooth" in its observable nature. The moving average filter is available for this purpose, inasmuch as very rapid excursions in ammoniacal concentration values will not occur in the realm of practical medical monitoring. Preferably, the display output 726 will provide a compilation of total ammoniacal concentration values as well as pH values in conjunction with that real time at which the filter values are developed. Accordingly, a real time clock function as represented at block 794 is incorporated with the system 718 and a time parameter, as represented at arrow 796 is combined with a pH value and the filtered total ammoniacal concentration value as represented at arrow 798 to provide a display update function as represented at block 800. The display output from that update function, along with corresponding real time information is directed to the video display drive function as represented at arrow 802 and block 804. Drive 804 then provides a video display as represented at arrow 806 and symbol 726. A permanent record also is developed. As represented at arrow 808 and block 810 the real time, pH level and total ammoniacal concentration data also are directed to a printer drive and a paper record is created as represented at arrow 812 and symbol 732.

The processing function 752 also carries out a variety of comparative functions generally associated with operator inputted threshold data. In this regard, the keypad function 722 is symbolically represented with the same numeration in the instant figure. That user inputted data, as represented at arrow 814 and block 816 will provide the value, n, for the number of measurements in a moving average filtering function, alarm limits with respect to the threshold for total ammoniacal concentration, the threshold for rates-of-rise of total ammoniacal concentration, a real time input, a sensor-type input, a display interval input and a pH value input where that parameter is not separately monitored. Such data, as represented at arrow 818 as well as the computer clock time function as represented at block 820 and arrow 822 is submitted to a comparative function wherein software provides a determination as to whether a threshold for total ammoniacal concentration has been equaled or exceeded and whether the rate-of-rise total ammoniacal concentration has exceeded a rate-of-rise threshold. This comparative function is represented at block 824 and performs in conjunction with the submitted total ammoniacal concentration values developed at block 788 as represented at arrow 826. Where either of the noted two thresholds are exceeded, then the system provides an oral cue to the practitioner. As represented at arrow 828 an alarm signal is submitted to a driver network represented at block 830, and as shown at arrow 832 and symbol 834, an audible alarm cue is provided upon an excursion above the noted thresholds. Real time adjustments are submitted to time block 800 as represented by arrow 844. The keypad input 722 provides for a resetting or acknowledgement function cutting off such alarms. As discussed in connection with FIG. 32, LED types of visual cuing also are provided. In this regard, as represented at arrow 836, an alarm signal is directed to a driver network 838, whereupon, as represented at arrows 840–842 leading to respective blocks 738, 740 and 742, the driver network 838 provides, where appropriate, a visual warning cue showing a rising total ammoniacal concentration; a visual alarm threshold cue showing that the inputted threshold for total ammoniacal concentration has been equaled or exceeded; or a visual rate rise alarm indicating that the inputted rate-of-rise of total ammoniacal concentration threshold has been equaled or exceeded.

FIGS. 34A–34E combine as labeled thereon to present a flowchart describing the monitoring methodology of the invention. In the discourse to follow concerning that flowchart, a variety of system parameters are employed. These parameters are defined in the tabulation set forth in Table II below.

Table II i=index t=real time $t_i$=real time of measurement of pH $t_i'$=real time of measurement of ammonia level in blood Ca(ti')

$t_i''$=next previous real time $t_{ROR}$=elapsed time from start @ time 0 for rate-of-rise $\delta t_{ROR}$=time interval used for rate-of-rise calculation $t_{rel}$=elapsed time from start of each displayable measurement set (pH, TAC, rate-of-rise)

ET=elapsed time between display of rate of change of TAC

RT=elapsed time between displays of TAC

ΔT=display update interval n=filter number

δ=interval between pH and TAC (variable)

$C_{TAC}(t_i')$=total ammoniacal concentration (TAC) calculated for real time $t_i'$ $\overline{C}_{TAC,n}(t_i)$=filtered TAC (n values average taken at time of last TAC calculated i.e., at time $t_i$ $\dot{\overline{C}}_{TAC}(t_i')$=rate of change of TAC taken over interval, $\delta t_{ROR}$ $$\dot{\overline{C}}_{TAC,n}(t_i') = \left\{ \frac{[\overline{C}_{TAC,n}(t_i') - \overline{C}_{TAC,n}(t_i''')]}{\delta t_{ROR}} \right\}$$

where $t_i'''=t_i'-\delta t_{ROR}$ $C_{th}$=Threshold for adverse effects $\dot{C}_{th}$=Rate of Rise Threshold System start is represented at node 850 and arrow 852. At startup, as represented at block 854, conventional initialization activities are carried out, including the entry of any default parameters. Then, as represented at arrow 856 and block 858, patient identification is entered at the keypad array 722. As represented at arrow 860 and block 862, the practitioner then enters the measurement display interval, ΔT, the homeostatic threshold for adverse effects ($C_{th}$); the rate-of-rise threshold, $\dot{C}_{th}$; the time interval for rate-of-rise calculation ($\delta t_{ROR}$) the number of values (n) for utilization with the moving average filter. Then, as represented at arrow 864 and block 866, the real time, i.e., time of day and date is entered by the practitioner. As represented at arrow 868 and symbol 870, the measurement function of the system then commences. As represented at arrow 872 and block 874 an index i, is said equal to one. Next, the parameter $t_{rel}$ representing the elapsed time from the start of each displayable measurement is set to equal zero; the parameter $t_{ROR}$ is set to equal zero. This parameter represents the time interval used for rate-of-rise calculation; and a parameter ET representing elapsed time, as well as the parameter RT representing the running time or relative elapsed time is started. The program then continues as represented at arrow 876 and block 878 wherein a query is posed as to whether a system stop command has been received. In the event that it has been received, then as represented at arrow 880 and node 882, the program ends. In the event that no system stop command has been received, then as represented at arrow 884 and block 886, the pH of the blood is measured at time, $t_i$. In this regard, the system at hand is one wherein ammonia gas concentration is measured and combined with a corresponding pH measurement to derive total ammoniacal concentration. The program then continues as represented at arrow 888 and block 890 which provides for measuring the ammonia concentration at time $t_i'$ which is the real time of measurement of ammonia level in blood Ca ($t_i'$). The parameter, δ, represents the interval between measurement of pH and ammonia content. Following such measurement, as represented at arrow 892 and block 894, total ammoniacal concentration in blood (TAC) is computed and that computation is assigned the real time $t_i'$. The resultant value is represented as: $C_{TAC}(t_i')$. As represented at arrow 896 and block 898, the system then sets the relative time, $t_{rel}$ or elapsed time from the start of each displayable measurement as equal to the running time, RT, and the elapsed time from the start for determining rate-of-rise, $t_{ROR}$ is set equal to elapsed time, ET, as provided as an elapsed time counter which, in general, is not reset. Then, as represented at arrow 900 and block 902, a gate keeping function is carried out wherein a determination is made as to whether the index, i, is greater than or equal to the number of components elected for the moving average filtering function or, n. Where the value, n, is not reached, then as represented at arrows 904 and 906 and block 908, the index, i, is incremented by one and, as represented at arrows 910 and 884, the program returns to commence measuring blood pH again as set forth at block 886.

In the event that the index counter indicates that a number, n, of measurements has been obtained, then as represented at arrow 912, the computations represented at block 914 are carried out. In this regard, the moving average filtering approach utilizes, n, total ammoniacal concentration values to derive an average value. For each additional TAC measurement entered into the queue, from which the last oldest value is dropped. Additionally, the time assigned for the TAC value which is published at the display is the time, $t_i'$ of the most recent measurement which is entered into the queue. The value which is published or displayed is represented as: $\overline{C}_{TAC,n}(t_i'$. Then, as represented at arrow 915 and block 916 the filtered total ammoniacal concentration (TAC) is recorded in memory and the program moves as represented at arrow 918 to the query posed at block 920 determining whether the elapsed time from the start of each displayable measurement $t_{REL}$ is greater than $\Delta T$ or the display update interval. In the event that it is not equal to or greater than that value, then as represented at arrow 906, the index, i, is incremented and the program loops to arrow 884. Where the time interval for display is at hand, then as represented at arrow 922 and block 924, the filtered or average total ammoniacal concentration in blood (TAC) and the pH measurement most recently taken are displayed at a real time, $t_i'$. As a correlative to this display of the numerical values, the system generates a real time graphics output displaying a time versus TAC value curve as well as an associated TAC level threshold. Additionally, a graphics display for pH is developed. This arrangement is represented at arrow 926 and block 928. Correspondingly, a printed document or strip may be generated as represented at arrow 930 and block 932. Next, as represented at arrow 934 and block 936, a determination is made as to whether the computed and filtered total ammoniacal concentration assigned for the time, $t_i'$ has a value greater than the corresponding filtered TAC value at the next previous measurement time, $t_i''$. Where the contemporaneous value is greater, then a rise in TAC is at hand and, as represented at arrow 938 and block 940, a visual warning cue is activated. This warning cue may be provided, as discussed above, as an illumination of an amber or yellow spectrum colored LED. In the event of a negative determination with respect to the query posed at block 936, then as represented at arrow 942 and block 944, any preexisting visual warning is deactivated and the program continues as represented at arrow 946. Correspondingly, where the warning cue is activated as represented at block 940, the program continues to arrow 946 as represented at arrow 948.

The program then proceeds as represented at arrow 946 and block 950 wherein a determination is made to whether the filtered value for a total ammoniacal concentration as currently measured, $\overline{C}_{TAC,n}(t_i')$ is greater than an inputted threshold value, $C_{th}$. In the event that the threshold is exceeded, then as represented at arrow 952 and block 954 both visual and aural cues are activated to alert the practitioner. In the event that the threshold is not exceeded, then as represented at arrow 956 and block 958, any threshold warning is deactivated. The program then continues as represented at arrow 960. Where a warning activation has been developed as represented at block 954, the program continues to arrow 960 as represented at arrow 962. Arrow 960 leads to the query posed at block 964 determining whether the time elapsed from the start time, $t_{ROR}$ is or equal to the time interval utilized for carrying out a rate-of-rise calculation with respect to TAC. In the event that the elapsed time has not reached that value, then the program proceeds as represented at arrows 966, 968 and block 970. At block 970, the elapsed time between displays of TAC, RT, is set to zero. The program then loops as represented at arrows 972 and 884.

In the event of an affirmative response to the query posed at block 964, then the time interval for calculating rate-of-rise of filtered TAC is at hand and, as represented at arrow 974 and block 976 the rate of change of total ammoniacal concentration during the period $\delta t_{ROR}$ is computed, the resulting value being identified as: $\dot{\overline{C}}_{TAC,n}(t_i')$. As represented at arrow 978 and block 980 the program then records the rate of change of filtered total ammoniacal concentration in memory and continues as represented at arrow 982. Arrow 982 leads to the display operation represented at block 984. In this regard, the rate of change of the filtered total ammoniacal concentration is assigned a real time, $t_i'$ for the time of the last measurement of ammonia level and that value is numerically displayed and may be incorporated graphically in the display program, for example, as or the like. The latter approach is represented by dual arrow 986 and block 988. Correspondingly, as represented at arrow 990 and block 992 a printout is provided showing this rate valuation. The program then continues as represented at arrow 994 and block 996, where a query is posed as to whether the computed rate-of-change of filtered total ammoniacal content is greater than an inputted rate-of-rise threshold, $C_{th}$. In the event that the threshold is exceeded, then as represented at arrow 998 and block 1000, visual and aural alarm cues are activated. In this regard, an LED in the red spectrum is illuminated and a warning sound is provided. Where the inquiry as posed at block 996 indicates that no rate-of-rise threshold is exceeded, then as represented at arrow 1002 and block 1004 any rate-of-rise warning is deactivated and the program continues as represented at arrow 1006. Where the rate-of-rise alarms have been activated as represented at block 1000, the program then continues to this arrow 1006 as represented at arrow 1008. Arrow 1006 leads to the instructions at block 1010 wherein the parameter ET or elapsed time between the displays of rate-of-change of filtered TAC is set to zero. The program then loops as represented at arrow 968, block 970 and arrow 972 to arrow 884.

Since certain changes may be made in the above system and method without departing from the scope of the invention herein involved, it is intended that all matter contained in the above description or shown in the accompanying drawings shall be interpreted as illustrative and not in a limiting sense.

What is claimed is:

1. A system for monitoring the ammoniacal concentration in blood, such blood exhibiting a pH value and being within a vascular system directing a bloodstream extending to peripheral regions of a body remotely disposed from the heart, comprising:

a blood by-passing assembly including:

a blood transport conduit extending from a proximal end to a distal tip, said distal tip being positionable in blood exchange relationship within said bloodstream at one of said peripheral regions, a blood sampling chamber coupled in blood exchange communication with said blood transport conduit proximal end, and a pump coupled with said sampling chamber and actuable to urge the transport of blood from said bloodstream into said sampling chamber;

an ammoniacal component sensor assembly having an ammoniacal component forward assembly located within said sampling chamber and contactable with blood within said sampling chamber, said sensor assembly being controllable to provide an ammoniacal sensor output; and a controller, controllable to control said ammoniacal component sensor assembly, and responsive to said ammoniacal sensor output for deriving a sequence of ammoniacal component parameters under said control, responsive to said ammoniacal component parameters to derive total ammoniacal concentration values and display signals corresponding therewith; and a display assembly responsive to said display signals to provide visibly perceptible information outputs corresponding therewith.

2. The system of claim 1 in which:

said controller includes an inputting assembly manually controllable to provide a total ammoniacal concentration threshold value;

said controller is responsive to said total ammoniacal concentration threshold value to retain it in memory;

said controller is responsive to a given said total ammoniacal concentration value and to said memory retained total ammoniacal concentration threshold value to derive an alarm signal when said given total ammoniacal concentration value is greater than said memory retained total ammoniacal concentration threshold value; and said display assembly is responsive to said alarm signal to provide a perceptible alarm output.

3. The system of claim 1 in which:

said controller includes an inputting assembly manually controllable to provide a rate of change of total ammoniacal concentration threshold value;

said controller is responsive to a given said total ammoniacal concentration value and to a previous such concentration value to derive a current total ammoniacal concentration rate of change value, and is responsive to said rate of change of total ammoniacal concentration threshold value and to said current total ammoniacal concentration rate of change value to derive an alarm signal when said current total ammoniacal concentration rate of change value is greater than or equal to said rate of change of total ammoniacal concentration threshold value, and said display assembly is responsive to said alarm signal to provide a perceptible alarm output.

4. The system of claim 1 in which:

said controller is responsive to a first said total ammoniacal concentration value and is responsive to a second said total ammoniacal concentration value derived subsequent to said first total ammoniacal concentration value, and is responsive to derive a warning signal when said second total ammoniacal concentration value is greater than said first total ammoniacal concentration value; and said display assembly is responsive to said warning signal to provide a perceptible warning output.

5. The system of claim 1 in which:

said controller includes a time clock providing a time output;

said controller is responsive to said real time output with the contemporaneous derived occurrence of a said display signal to derive a time associated display signal; and said display assembly is responsive to each of a sequence said of said time associated display signals to produce a trend defining graphics display thereof.

6. The system of claim 1 in which:

said controller is responsive to retain each said total ammoniacal concentration value in memory, is responsive to a given said total ammoniacal concentration and n−1 memory retained previously occurring said values of total ammoniacal concentration to derive a filtered total ammoniacal concentration value representing the moving average filtering of n values of said total ammoniacal concentration value and provided as said display signal.

7. The system of claim 1 in which:

said ammoniacal component forward assembly comprises:

an ammoniacal component concentration reactor having an output condition responsive to the concentration of said ammoniacal component in blood;

a membrane forming a blood confronting surface of said reactor, permeable to said ammoniacal component, said surface being contactable with said blood within said sampling chamber; and said ammoniacal component sensor includes: a transmission assembly for conveying said ammoniacal sensor output as a signal corresponding with said output condition.

8. The system of claim 7 in which:

said ammoniacal component is ammonia ($NH_3$);

said membrane is permiable to gaseous ammonia;

said reactor is a gaseous ammonia sensitive dye;

said transmission assembly is a fiberoptic colorimetric measurement assembly which quantiates a change in color of the dye and is mounted within said first sensor channel; and said controller additionally is responsive to said pH value to derive said total ammoniacal concentration value.

9. The system of claim 7 in which:

said ammoniacal component is ammonium;

said membrane is permeable to ammonium ion ($NH_4^+$);

said reactor comprises first and second electrodes immersed within an electrolyte sensitive to said ammonium ion; and said transmission assembly comprises a potentiometric assembly coupled with said first and second electrodes.

10. The system of claim 7 in which:

said ammoniacal component is ammonium;

said membrane is permeable to ammonium ion ($NH_4^+$);

said reactor comprises first and second electrodes immersed within an electrolyte sensitive to said ammonium ion; and said transmission assembly comprises an amperometric assembly coupled with said first and second electrodes.

11. The system of claim 7 wherein:

said reactor comprises an ammoniacal component-sensitive fluorescent material having a fluorescence intensity as said output condition; and said transmission component is a fiberoptic assembly for stimulating said reactor and conveying said fluorescence intensity as said ammoniacal sensor output.

12. The system of claim 7 wherein said reactor comprises an ammoniacal component-sensitive fluorescent material stimulatable into fluorescence, the rate of quenching of said fluorescence being said output condition; and said transmission component is a fiberoptic assembly for stimulating said reactor and conveying resultant generated light as said ammoniacal sensor output.

13. The system of claim 7 in which said ammoniacal component reactor is configured as a Schottky diode array having a conductive polymer responsive to said ammoniacal component to effect a forward bias alteration as said ammoniacal sensor output.

14. The system of claim 7 in which said ammoniacal component sensor forward assembly is configured as a Schottky diode array having a conductive polymer responsive to said ammoniacal component to effect a forward bias alteration as said ammoniacal sensor output.

15. The system of claim 7 in which:

said ammoniacal component is ammonia ($NH_3$);

said ammoniacal component sensor comprises a fiberoptic assembly having a forward face as said forward assembly in blood contacting position within said blood sampling chamber, said forward face being adapted for direct light exchange communication with said blood within said sampling chamber, said fiberoptic assembly being extensible to a light source and photoresponsive assembly for deriving said ammoniacal sensor output; and said controller is additionally responsive to said pH value to derive said total ammoniacal concentration value.

16. The system of claim 1 in which said ammoniacal component sensor comprises:

a fiberoptic assembly extending from a proximal end to a fiberoptic tip forming a component of said forward assembly of said ammoniacal component sensor assembly;

a membrane coupled with said fiberoptic assembly at said forward assembly, permeable to said ammoniacal component, having an outer surface in blood contacting position within said blood sampling chamber, and an inner surface spaced from said fiberoptic tip to define an equilibration cavity; and including a light transmission and reception assembly optically coupled with said fiberoptic assembly at said proximal end and controllable to derive said ammoniacal sensor output with respect to ammoniacal component at said equilibrium cavity.

17. The system of claim 1 in which said ammoniacal component sensor comprises:

a fiberoptic assembly extending from a proximal end to said forward assembly and having a forward light transmission leg and a return leg spaced from said forward light transmission leg to define a gap situated at said forward assembly; and a membrane permeable to said ammoniacal component, having an outer surface in blood contacting position within said blood sampling chamber, said membrane sealingly extending about said gap to define an equilibriation cavity.

18. A system for monitoring the ammoniacal concentration in blood, such blood exhibiting a pH value, and being within a vascular system directing a bloodstream extending to a peripheral region of the body remotely disposed from the heart, comprising:

a catheter assembly having a proximal end region, a measurement region spaced therefrom extending to a tip, having a first sensor channel extending from said proximal region to said measurement region, said measurement region being adapted to be positionable within said bloodstream;

an ammoniacal component sensor assembly, supported by said first sensor channel, having an ammoniacal component responsive forward assembly at said measurement region contactable with flowing blood within said bloodstream, said sensor assembly being controllable to provide an ammoniacal sensor output at said proximal end region;

a controller coupled to effect operational control of said ammoniacal component sensor assembly, and responsive to said ammoniacal sensor output for deriving an ammoniacal component parameter at repeating measurement intervals, responsive to said ammoniacal component parameter to derive a total ammoniacal concentration value and a display signal corresponding therewith;

said controller including an inputting assembly manually controllable to provide a total ammoniacal concentration threshold value, is further responsive to said total ammoniacal concentration threshold value to retain it in memory, and said controller is responsive to a given said total ammoniacal concentration value and to said memory retained total ammoniacal concentration threshold value to derive an alarm signal when said given total ammoniacal concentration value is greater than said memory retained total ammoniacal concentration threshold value; and a display assembly responsive to said display signal to provide a visibly perceptible information output corresponding therewith, and is responsive to said alarm signal to provide a perceptible alarm output.

19. The system of claim 18 in which:

said ammoniacal component responsive forward assembly comprises:

an ammoniacal component concentration reactor having an output condition responsive to the concentration of said ammoniacal component in blood;

a membrane forming a blood confronting surface of said reactor, permeable to said ammoniacal component, said surface being contactable with blood within said bloodstream; and said ammoniacal component sensor includes; a transmission assembly for conveying a signal corresponding with said output condition to said catheter proximal end region as said ammoniacal sensor output.

20. The system of claim 19 in which:

said ammoniacal component is ammonium;

said membrane is permeable to ammonium ion ($NH_4^+$);

said reactor comprises first and second electrodes immersed within an electrolyte sensitive to said ammonium ion; and said transmission assembly comprises a potentiometric assembly coupled with said first and second electrodes.

21. The system of claim 19 in which:

said ammoniacal component is ammonium;

said membrane is permeable to ammonium ion ($NH_4^+$);

said reactor comprises first and second electrodes immersed within an electrolyte sensitive to said ammonium ion; and said transmission assembly comprises an amperometric assembly coupled with said first and second electrodes.

22. The system of claim 19 wherein:

said reactor comprises an ammoniacal component-sensitive fluorescent material having a fluorescence intensity as said output condition; and said transmission component is a fiberoptic assembly for stimulating said reactor and conveying said fluorescence intensity as said ammoniacal sensor output.

23. The system of claim 19 wherein
said reactor comprises an ammoniacal component-sensitive fluorescent material stimulatable into fluorescence, the rate of quenching of said fluorescence being said output condition; and
said transmission component is a fiberoptic assembly for stimulating said reactor and conveying resultant generated light as said ammoniacal sensor output.

24. The system of claim 18 in which said ammoniacal component sensor comprises:
a fiberoptic assembly extending within said first sensor channel from said catheter assembly proximal end region to a fiberoptic tip located at and forming a component of said forward assembly;
a membrane forming a component of said forward assembly, permeable to said ammoniacal component, having an outer surface contactable with said bloodstream and an inner surface spaced from said fiberoptic tip to define an equilibration cavity; and
including a light transmission and reception assembly optically coupled with said fiberoptic assembly at said proximal end region and controllable to derive said ammoniacal sensor output with respect to ammoniacal component at said equilibration cavity.

25. The system of claim 24 in which said membrane inner surface is light reflecting.

26. The system of claim 18 in which said ammoniacal component sensor comprises:
a fiberoptic assembly extending from said catheter proximal end region to a fiberoptic tip at said forward assembly, including an outer surface extending inwardly from said fiberoptic tip;
an end plug impervious to blood having an inwardly disposed surface spaced from said fiberoptic tip to define the length of an equilibration cavity;
a membrane permeable to said ammoniacal component having an outer surface contactable with said bloodstream, said membrane extending sealingly about said outer surface and said end plug to define the sides of said equilibration cavity.

27. The system of claim 26 in which said ammoniacal component sensor comprises:
a fiberoptic assembly extending from said catheter proximal end region to said forward assembly and having a forward light transmission leg and a return transmission leg spaced from said forward light transmission leg to define a gap situated at said forward assembly; and
a membrane permeable to said ammoniacal component, having an outer surface contactable with said bloodstream, said membrane sealingly extending about said gap to define an equilibration cavity.

28. The system of claim 18 in which:
said ammoniacal component is ammonia ($NH_3$);
said ammoniacal sensor output is provided in correspondence with the concentration of ammonia gas ($NH_3$) in said bloodstream; and
said controller derives said total ammoniacal concentration value in correspondence with the expressions:

$$Ca(NH_4^+)=Ca(NH_3)/[10\ exp(pH-pKa)]$$

$$Ca=Ca(NH_3)+Ca(NH_4^+)$$

where: $Ca(NH_4^+)$ is the concentration of ammonium ions in blood, $Ca(NH_3)$ is the measured concentration of ammonia gas in blood, pH is measured blood pH, pKa is the pH level of solution above which ammoniacal fluid exists only as a gas, and Ca is the total ammoniacal concentration in blood.

29. The system of claim 18 in which:
said catheter assembly includes a second sensor channel extending from said proximal region to said measurement region;
including a pH sensor assembly supported by said second sensor channel, having a pH responsive forward assembly and a fiberoptic transmission component extending therefrom to said proximal region, said pH sensor assembly being controllable to provide a pH output at said proximal region;
said ammoniacal component is ammonia ($NH_3$); and
said controller is responsive to control said pH sensor, and is responsive to said pH output to derive aid total ammoniacal concentration value.

30. The system of claim 29 in which:
said pH sensor forward assembly includes a membrane impervious to blood and permeable to hydrogen ions and including a pH indicator located for response to said hydrogen ions; and
said controller derives said total ammoniacal concentration value in correspondence with the expressions:

$$Ca(NH_4^+)=Ca(NH_3)/[10\ exp(pH-pKa)]$$

$$Ca=Ca(NH_3)+Ca(NH_4^+)$$

where: $Ca(NH_4^+)$ is the concentration of ammonium ions in blood, Ca ($NH_3$) is the measured concentration of ammonia gas in blood, pH is measured blood pH, pKa is the pH level of solution above which ammoniacal fluid exists only as a gas, and Ca is the total ammoniacal concentration in blood.

31. The system of claim 18 in which:
said catheter assembly has an outer principal cross-sectional dimension effective for insertion within said bloodstream at said peripheral region of said vascular system while avoiding generation of substantial hydraulic impedance to bloodflow.

32. The system of claim 31 in which said outer principal cross-sectional dimension is within a range of about 0.010 inch to 0.060 inch.

33. A system for monitoring the ammoniacal concentration in blood, such blood exhibiting a pH value, and being within a vascular system directing a bloodstream extending to a peripheral region of the body remotely disposed from the heart, comprising:
a catheter assembly having a proximal end region, a measurement region spaced therefrom extending to a tip, having a first sensor channel extending from said proximal region to said measurement region, said measurement region being adapted to be positionable within said bloodstream at said peripheral region of said vascular system;
an ammoniacal component sensor assembly, supported by said first sensor channel, having an ammoniacal component responsive forward assembly at said measurement region contactable with flowing blood within said bloodstream, said sensor assembly being controllable to provide an ammoniacal sensor output at said proximal end region;
a controller coupled to effect operational control of said ammoniacal component sensor assembly, and responsive to said ammoniacal sensor output for deriving an ammoniacal component parameter at repeating measurement intervals, responsive to said ammoniacal component parameter to derive a total ammoniacal concentration value and a display signal corresponding therewith, said controller including an inputting assembly manually controllable to provide a rate of change of total ammoniacal concentration threshold value, said controller being responsive to a given said total ammoniacal concentration value and to a previous such concentration value to derive a current total ammoniacal concentration rate of change value, and is responsive to said rate of change of total ammoniacal concentration threshold value and to said current total ammoniacal concentration rate of change value to derive an alarm signal when said current total ammoniacal concentration rate of change value is greater than or equal to said rate of change of total ammoniacal concentration threshold value, and a display assembly responsive to said display signal to provide a visibly perceptible information output corresponding therewith, and being responsive to said alarm signal to provide a perceptible alarm output.

34. The system of claim 33 in which said ammoniacal component sensor comprises:

a fiberoptic assembly extending within said first sensor channel from said catheter assembly proximal end region to a fiberoptic tip located at and forming a component of said forward assembly;

a membrane forming a component of said forward assembly, permeable to said ammoniacal component, having an outer surface contactable with said bloodstream and an inner surface spaced from said fiberoptic tip to define an equilibration cavity; and including a light transmission and reception assembly optically coupled with said fiberoptic assembly at said proximal end region and controllable to derive said ammoniacal sensor output with respect to ammoniacal component at said equilibriation cavity.

35. The system of claim 34 in which said membrane inner surface is light reflecting.

36. The system of claim 33 in which said ammoniacal component sensor comprises:

a fiberoptic assembly extending from said catheter proximal end region to a fiberoptic tip at said forward assembly, including an outer surface extending inwardly from said fiberoptic tip;

an end plug impervious to blood having an inwardly disposed surface spaced from said fiberoptic tip to define the length of an equilibriation cavity;

a membrane permeable to said ammoniacal component having an outer surface contactable with said bloodstream, said membrane extending sealingly about said outer surface and said end plug to define the sides of said equilibration cavity.

37. The system of claim 33 in which said ammoniacal component sensor comprises:

a fiberoptic assembly extending from said catheter proximal end region to said forward assembly and having a forward light transmission leg and a return transmission leg spaced from said forward light transmission leg to define a gap situated at said forward assembly; and a membrane permeable to said ammoniacal component, having an outer surface contactable with said bloodstream, said membrane sealingly extending about said gap to define an equilibration cavity.

38. The system of claim 33 in which:

said ammoniacal component is ammonia ($NH_3$);

said ammoniacal sensor output is provided in correspondence with the concentration of ammonia gas ($NH_3$) in said bloodstream; and said controller derives said total ammoniacal concentration value in correspondence with the expressions:

$$Ca(NH_4^+)=Ca(NH_3)/[10\ exp(pH-pKa)]$$

$$Ca=Ca(NH_3)+Ca(NH_4^+)$$

where: $Ca(NH_4^+)$ is the concentration of ammonium ions in blood, $Ca(NH_3)$ is the measured concentration of ammonia gas in blood, pH is measured blood pH, pKa is the pH level of solution above which ammoniacal fluid exists only as a gas, and Ca is the total ammoniacal concentration in blood.

39. The system of claim 33 in which:

said catheter assembly includes a second sensor channel extending from said proximal region to said measurement region;

including a pH sensor assembly supported by said second sensor channel, having a pH responsive forward assembly and a fiberoptic transmission component extending therefrom to said proximal region, said pH sensor assembly being controllable to provide a pH output at said proximal region;

said ammoniacal component is ammonia ($NH_3$); and said controller is responsive to control said pH sensor, and is responsive to said pH output to derive said total ammoniacal concentration value.

40. The system of claim 39 in which:

said pH sensor forward assembly includes a membrane impervious to blood and permeable to hydrogen ions and including a pH indicator located for response to said hydrogen ions; and said controller derives said total ammoniacal concentration value in correspondence with the expressions:

$$Ca(NH_4^+)=Ca(NH_3)/[10\ exp(pH-pKa)]$$

$$Ca=Ca(NH_3)+Ca(NH_4^+)$$

where: $Ca(NH_4^+)$ is the concentration of ammonium ions in blood, $Ca\ (NH_3)$ is the measured concentration of ammonia gas in blood, pH is measured blood pH, pKa is the pH level of solution above which ammoniacal fluid exists only as a gas, and Ca is the total ammoniacal concentration in blood.

41. The system of claim 33 in which:

said catheter assembly has an outer principal cross-sectional dimension effective for insertion within said bloodstream at said peripheral region of said vascular system while avoiding generation of substantial hydraulic impedance to bloodflow.

42. The system of claim 41 in which said outer principal cross-sectional dimension is within a range of about 0.010 inch to 0.060 inch.

43. The system of claim 33 in which:

said ammoniacal component responsive forward assembly comprises:

an ammoniacal component concentration reactor having an output condition responsive to the concentration of said ammoniacal component in blood;

a membrane forming a blood confronting surface of said reactor, permeable to said ammoniacal component, said surface being contactable with blood within said bloodstream; and said ammoniacal component sensor includes; a transmission assembly for conveying a signal corresponding with said output condition to said catheter proximal end region as said ammoniacal sensor output.

44. The system of claim 43 wherein:
said reactor comprises an ammoniacal component-sensitive fluorescent material having a fluorescence intensity as said output condition; and
said transmission component is a fiberoptic assembly for stimulating said reactor and conveying said fluorescence intensity as said ammoniacal sensor output.

45. The system of claim 43 wherein
said reactor comprises an ammoniacal component-sensitive fluorescent material stimulatable into fluorescence, the rate of quenching of said fluorescence being said output condition; and
said transmission component is a fiberoptic assembly for stimulating said reactor and conveying resultant generated light as said ammoniacal sensor output.

46. The system of claim 43 in which:
said ammoniacal component is ammonium;
said membrane is permeable to ammonium ion ($NH_4^+$);
said reactor comprises first and second electrodes immersed within an electrolyte sensitive to said ammonium ion; and
said transmission assembly comprises a potentiometric assembly coupled with said first and second electrodes.

47. The system of claim 43 in which:
said ammoniacal component is ammonium;
said membrane is permeable to ammonium ion ($NH_4^+$);
said reactor comprises first and second electrodes immersed within an electrolyte sensitive to said ammonium ion; and
said transmission assembly comprises a potentiometric assembly coupled with said first and second electrodes.

48. A system for monitoring the ammoniacal concentration in blood, such blood exhibiting a pH value, and being within a vascular system directing a bloodstream extending to a peripheral region of the body remotely disposed from the heart, comprising:
a catheter assembly having a proximal end region, a measurement region spaced therefrom extending to a tip, having a first sensor channel extending from said proximal region to said measurement region, said measurement region being adapted to be positionable within said bloodstream at said peripheral region;
an ammoniacal component sensor assembly, supported by said first sensor channel, having an ammoniacal component responsive forward assembly at said measurement region contactable with flowing blood within said bloodstream, said sensor assembly being controllable to provide an ammoniacal sensor output at said proximal end region;
a controller coupled to effect operational control of said ammoniacal component sensor assembly, and responsive to said ammoniacal sensor output for deriving an ammoniacal component parameter at repeating measurement intervals, responsive to said ammoniacal component parameter to derive a total ammoniacal concentration value and a display signal corresponding therewith, said controller being responsive to a first said total ammoniacal concentration value and is responsive to a second said total ammoniacal concentration value derived subsequent to said first ammoniacal concentration value, and is responsive to derive a warning signal when said second total ammoniacal concentration value is greater than said first total ammoniacal concentration value; and
a display assembly responsive to said display signal to provide a visibly perceptible information output corresponding therewith, and being responsive to said warning signal to provide a perceptible warning output.

49. The system of claim 48 in which said ammoniacal component sensor comprises:
a fiberoptic assembly extending within said first sensor channel from said catheter assembly proximal end region to a fiberoptic tip located at and forming a component of said forward assembly;
a membrane forming a component of said forward assembly, permeable to said ammoniacal component, having an outer surface contactable with said bloodstream and an inner surface spaced from said fiberoptic tip to define an equilibration cavity; and
including a light transmission and reception assembly optically coupled with said fiberoptic assembly at said proximal end region and controllable to derive said ammoniacal sensor output with respect to ammoniacal component at said equilibration cavity.

50. The system of claim 49 in which said membrane inner surface is light reflecting.

51. The system of claim 48 in which said ammoniacal component sensor comprises:
a fiberoptic assembly extending from said catheter proximal end region to a fiberoptic tip at said forward assembly, including an outer surface extending inwardly from said fiberoptic tip;
an end plug impervious to blood having an inwardly disposed surface spaced from said fiberoptic tip to define the length of an equilibration cavity;
a membrane permeable to said ammoniacal component having an outer surface contactable with said bloodstream, said membrane extending sealingly about said outer surface and said end plug to define the sides of said equilibration cavity.

52. The system of claim 48 in which said ammoniacal component sensor comprises:
a fiberoptic assembly extending from said catheter proximal end region to said forward assembly and having a forward light transmission leg and a return transmission leg spaced from said forward light transmission leg to define a gap situated at said forward assembly; and
a membrane permeable to said ammoniacal component, having an outer surface contactable with said bloodstream, said membrane sealingly extending about said gap to define an equilibration cavity.

53. The system of claim 48 in which:
said ammoniacal component is ammonia ($NH_3$);
said ammoniacal sensor output is provided in correspondence with the concentration of ammonia gas ($NH_3$) in said bloodstream; and
said controller derives said total ammoniacal concentration value in correspondence with the expressions:

$$Ca(NH_4^+)=Ca(NH_3)/[10\ exp(pH-pKa)]$$

$$Ca=Ca(NH_3)+Ca(NH_4^+)$$

where: $Ca(NH_4^+)$ is the concentration of ammonium ions in blood, $Ca(NH_3)$ is the measured concentration of ammonia gas in blood, pH is measured blood pH, pKa is the pH level of solution above which ammoniacal fluid exists only as a gas, and Ca is the total ammoniacal concentration in blood.

54. The system of claim 48 in which:

said catheter assembly includes a second sensor channel extending from said proximal region to said measurement region;

including a pH sensor assembly supported by said second sensor channel, having a pH responsive forward assembly and a fiberoptic transmission component extending therefrom to said proximal region, said pH sensor assembly being controllable to provide a pH output at said proximal region;

said ammoniacal component is ammonia ($NH_3$); and said controller is responsive to control said pH sensor, and is responsive to said pH output to derive said total ammoniacal concentration value.

55. The system of claim 54 in which:

said pH sensor forward assembly includes a membrane impervious to blood and permeable to hydrogen ions and including a pH indicator located for response to said hydrogen ions; and said controller derives said total ammoniacal concentration value in correspondence with the expressions:

$$Ca(NH_4^+) = Ca(NH_3)/[10\ exp(pH-pKa)]$$

$$Ca = Ca(NH_3) + Ca(NH_4^+)$$

where: $Ca(NH_4^+)$ is the concentration of ammonium ions in blood, $Ca\ (NH_3)$ is the measured concentration of ammonia gas in blood, pH is measured blood pH, pKa is the pH level of solution above which ammoniacal fluid exists only as a gas, and Ca is the total ammoniacal concentration in blood.

56. The system of claim 48 in which:

said catheter assembly has an outer principal cross-sectional dimension effective for insertion within said bloodstream at said peripheral region of said vascular system while avoiding generation of substantial hydraulic impedance to bloodflow.

57. The system of claim 56 in which said outer principal cross-sectional dimension is within a range of about 0.010 inch to 0.060 inch.

58. The system of claim 48 in which:

said ammoniacal component responsive forward assembly comprises:

an ammoniacal component concentration reactor having an output condition responsive to the concentration of said ammoniacal component in blood;

a membrane forming a blood confronting surface of said reactor, permeable to said ammoniacal component, said surface being contactable with blood within said bloodstream; and said ammoniacal component sensor includes; a transmission assembly for conveying a signal corresponding with said output condition to said catheter proximal end region as said ammoniacal sensor output.

59. The system of claim 58 wherein:

said reactor comprises an ammoniacal component-sensitive fluorescent material having a fluorescence intensity as said output condition; and said transmission component is a fiberoptic assembly for stimulating said reactor and conveying said fluorescence intensity as said ammoniacal sensor output.

60. The system of claim 58 wherein said reactor comprises an ammoniacal component-sensitive fluorescent material stimulatable into fluorescence, the rate of quenching of said fluorescence being said output condition; and said transmission component is a fiberoptic assembly for stimulating said reactor and conveying resultant generated light as said ammoniacal sensor output.

61. The system of claim 58 in which:

said ammoniacal component is ammonium;

said membrane is permeable to ammonium ion ($NH_4^+$);

said reactor comprises first and second electrodes immersed within an electrolyte sensitive to said ammonium ion; and said transmission assembly comprises a potentiometric assembly coupled with said first and second electrodes.

62. The system of claim 58 in which:

said ammoniacal component is ammonium;

said membrane is permeable to ammonium ion ($NH_4^+$);

said reactor comprises first and second electrodes immersed within an electrolyte sensitive to said ammonium ion; and said transmission assembly comprises a potentiometric assembly coupled with said first and second electrodes.

63. A system for monitoring the ammoniacal concentration in blood, such blood exhibiting a pH value, and being within a vascular system directing a bloodstream extending to a peripheral region of the body remotely disposed from the heart, comprising:

a catheter assembly having a proximal end region, a measurement region spaced therefrom extending to a tip, having a first sensor channel extending from said proximal region to said measurement region, said measurement region being adapted to be positionable within said bloodstream at said peripheral region of said vascular system;

an ammoniacal component sensor assembly, supported by said first sensor channel, having an ammoniacal component responsive forward assembly at said measurement region contactable with flowing blood within said bloodstream, said sensor assembly being controllable to provide an ammoniacal sensor output at said proximal end region;

a controller coupled to effect operational control of said ammoniacal component sensor assembly, and responsive to said ammoniacal sensor output for deriving an ammoniacal component parameter at repeating measurement intervals, responsive to said ammoniacal component parameter to derive a total ammoniacal concentration value and a display signal corresponding therewith, said controller including a real time clock providing a real time output, and being responsive to said real time output with the contemporaneous derived occurrence of said total ammoniacal concentration value to derive a time associated display signal; and a display assembly responsive to said display signal to provide a visibly perceptible information output corresponding therewith, and being responsive to each of a sequence of said time associated display signals to produce a trend defining graphics display thereof.

64. The system of claim 63 in which said ammoniacal component sensor comprises:

a fiberoptic assembly extending within said first sensor channel from said catheter assembly proximal end region to a fiberoptic tip located at and forming a component of said forward assembly;

a membrane forming a component of said forward assembly, permeable to said ammoniacal component, having an outer surface contactable with said bloodstream and an inner surface spaced from said fiberoptic tip to define an equilibration cavity; and including a light transmission and reception assembly optically coupled with said fiberoptic assembly at said proximal end region and controllable to derive said ammoniacal sensor output with respect to ammoniacal component at said equilibration cavity.

65. The system of claim 64 in which said membrane inner surface is light reflecting.

66. The system of claim 63 in which said ammoniacal component sensor comprises:
a fiberoptic assembly extending from said catheter proximal end region to a fiberoptic tip at said forward assembly, including an outer surface extending inwardly from said fiberoptic tip;
an end plug impervious to blood having an inwardly disposed surface spaced from said fiberoptic tip to define the length of an equilibration cavity;
a membrane permeable to said ammoniacal component having an outer surface contactable with said bloodstream, said membrane extending sealingly about said outer surface and said end plug to define the sides of said equilibration cavity.

67. The system of claim 63 in which said ammoniacal component sensor comprises:
a fiberoptic assembly extending from said catheter proximal end region to said forward assembly and having a forward light transmission leg and a return transmission leg spaced from said forward light transmission leg to define a gap situated at said forward assembly; and
a membrane permeable to said ammoniacal component, having an outer surface contactable with said bloodstream, said membrane sealingly extending about said gap to define an equilibration cavity.

68. The system of claim 63 in which:
said ammoniacal component is ammonia ($NH_3$);
said ammoniacal sensor output is provided in correspondence with the concentration of ammonia gas ($NH_3$) in said bloodstream; and
said controller derives said total ammoniacal concentration value in correspondence with the expressions:

$$Ca(NH_4^+) = Ca(NH_3)/[10 \exp(pH-pKa)]$$

$$Ca = Ca(NH_3) + Ca(NH_4^+)$$

where: $Ca(NH_4^+)$ is the concentration of ammonium ions in blood, $Ca(NH_3)$ is the measured concentration of ammonia gas in blood, pH is measured blood pH, pKa is the pH level of solution above which ammoniacal fluid exists only as a gas, and Ca is the total ammoniacal concentration in blood.

69. The system of claim 63 in which:
said catheter assembly includes a second sensor channel extending from said proximal region to said measurement region;
including a pH sensor assembly supported by said second sensor channel, having a pH responsive forward assembly and a fiberoptic transmission component extending therefrom to said proximal region, said pH sensor assembly being controllable to provide a pH output at said proximal region;
said ammoniacal component is ammonia ($NH_3$); and
said controller is responsive to control said pH sensor, and is responsive to said pH output to derive said total ammoniacal concentration value.

70. The system of claim 69 in which:
said pH sensor forward assembly includes a membrane impervious to blood and permeable to hydrogen ions and including a pH indicator located for response to said hydrogen ions; and
said controller derives said total ammoniacal concentration value in correspondence with the expressions:

$$Ca(NH_4^+) = Ca(NH_3)/[10 \exp(pH-pKa)]$$

$$Ca = Ca(NH_3) + Ca(NH_4^+)$$

where: $Ca(NH_4^+)$ is the concentration of ammonium ions in blood, Ca ($NH_3$) is the measured concentration of ammonia gas in blood, pH is measured blood pH, pKa is the pH level of solution above which ammoniacal fluid exists only as a gas, and Ca is the total ammoniacal concentration in blood.

71. The system of claim 63 in which:
said catheter assembly has an outer principal cross-sectional dimension effective for insertion within said bloodstream at said peripheral region of said vascular system while avoiding generation of substantial hydraulic impedance to bloodflow.

72. The system of claim 71 in which said outer principal cross-sectional dimension is within a range of about 0.010 inch to 0.060 inch.

73. The system of claim 63 in which:
said ammoniacal component responsive forward assembly comprises:
an ammoniacal component concentration reactor having an output condition responsive to the concentration of said ammoniacal component in blood;
a membrane forming a blood confronting surface of said reactor, permeable to said ammoniacal component, said surface being contactable with blood within said bloodstream; and
said ammoniacal component sensor includes; a transmission assembly for conveying a signal corresponding with said output condition to said catheter proximal end region as said ammoniacal sensor output.

74. The system of claim 73 wherein:
said reactor comprises an ammoniacal component-sensitive fluorescent material having a fluorescence intensity as said output condition; and
said transmission component is a fiberoptic assembly for stimulating said reactor and conveying said fluorescence intensity as said ammoniacal sensor output.

75. The system of claim 73 wherein
said reactor comprises an ammoniacal component-sensitive fluorescent material stimulatable into fluorescence, the rate of quenching of said fluorescence being said output condition; and
said transmission component is a fiberoptic assembly for stimulating said reactor and conveying resultant generated light as said ammoniacal sensor output.

76. The system of claim 73 in which:
said ammoniacal component is ammonium;
said membrane is permeable to ammonium ion ($NH_4^+$);
said reactor comprises first and second electrodes immersed within an electrolyte sensitive to said ammonium ion; and
said transmission assembly comprises a potentiometric assembly coupled with said first and second electrodes.

77. The system of claim 73 in which:
said ammoniacal component is ammonium;
said membrane is permeable to ammonium ion ($NH_4^+$);
said reactor comprises first and second electrodes immersed within an electrolyte sensitive to said ammonium ion; and said transmission assembly comprises a potentiometric assembly coupled with said first and second electrodes.

78. A system for monitoring the ammoniacal concentration in blood, such blood exhibiting a pH value, and being within a vascular system directing a bloodstream extending to a peripheral region of the body remotely disposed from the heart, comprising:

a catheter assembly having a proximal end region, a measurement region spaced therefrom extending to a tip, having a first sensor channel extending from said proximal region to said measurement region, said measurement region being adapted to be positionable within said bloodstream at said peripheral region;

an ammoniacal component sensor assembly, supported by said first sensor channel, having an ammoniacal component responsive forward assembly at said measurement region contactable with flowing blood within said bloodstream, said sensor assembly being controllable to provide an ammoniacal sensor output at said proximal end region;

a controller coupled to effect operational control of said ammoniacal component sensor assembly, and responsive to said ammoniacal sensor output for deriving an ammoniacal component parameter at repeating measurement intervals, responsive to said ammoniacal component parameter to derive a total ammoniacal concentration value and a display signal corresponding therewith, said controller being responsive to retain each said total ammoniacal concentration value in memory, being responsive to a given said total ammoniacal concentration and n−1 memory retained previously occurring said values of total ammoniacal concentration to derive a filtered total ammoniacal concentration value representing the moving average filtering of n values of said total ammoniacal concentration value and provided as said display signal; and a display assembly responsive to said display signal to provide a visibly perceptible information output corresponding therewith.

79. The system of claim 78 in which said ammoniacal component sensor comprises:

a fiberoptic assembly extending within said first sensor channel from said catheter assembly proximal end region to a fiberoptic tip located at and forming a component of said forward assembly;

a membrane forming a component of said forward assembly, permeable to said ammoniacal component, having an outer surface contactable with said bloodstream and an inner surface spaced from said fiberoptic tip to define an equilibration cavity; and including a light transmission and reception assembly optically coupled with said fiberoptic assembly at said proximal end region and controllable to derive said ammoniacal sensor output with respect to ammoniacal component at said equilibration cavity.

80. The system of claim 79 in which said membrane inner surface is light reflecting.

81. The system of claim 78 in which said ammoniacal component sensor comprises:

a fiberoptic assembly extending from said catheter proximal end region to a fiberoptic tip at said forward assembly, including an outer surface extending inwardly from said fiberoptic tip;

an end plug impervious to blood having an inwardly disposed surface spaced from said fiberoptic tip to define the length of an equilibration cavity;

a membrane permeable to said ammoniacal component having an outer surface contactable with said bloodstream, said membrane extending sealingly about said outer surface and said end plug to define the sides of said equilibration cavity.

82. The system of claim 78 in which said ammoniacal component sensor comprises:

a fiberoptic assembly extending from said catheter proximal end region to said forward assembly and having a forward light transmission leg and a return transmission leg spaced from said forward light transmission leg to define a gap situated at said forward assembly; and a membrane permeable to said ammoniacal component, having an outer surface contactable with said bloodstream, said membrane sealingly extending about said gap to define an equilibration cavity.

83. The system of claim 78 in which:

said ammoniacal component is ammonia ($NH_3$);

said ammoniacal sensor output is provided in correspondence with the concentration of ammonia gas ($NH_3$) in said bloodstream; and said controller derives said total ammoniacal concentration value in correspondence with the expressions:

$$Ca(NH_4^+)=Ca(NH_3)/[10\ exp(pH-pKa)]$$

$$Ca=Ca(NH_3)+Ca(NH_4^+)$$

where: $Ca(NH_4^+)$ is the concentration of ammonium ions in blood, $Ca(NH_3)$ is the measured concentration of ammonia gas in blood, pH is measured blood pH, pKa is the pH level of solution above which ammoniacal fluid exists only as a gas, and Ca is the total ammoniacal concentration in blood.

84. The system of claim 78 in which:

said catheter assembly includes a second sensor channel extending from said proximal region to said measurement region;

including a pH sensor assembly supported by said second sensor channel, having a pH responsive forward assembly and a fiberoptic transmission component extending therefrom to said proximal region, said pH sensor assembly being controllable to provide a pH output at said proximal region;

said ammoniacal component is ammonia ($NH_3$); and said controller is responsive to control said pH sensor, and is responsive to said pH output to derive said total ammoniacal concentration value.

85. The system of claim 84 in which:

said pH sensor forward assembly includes a membrane impervious to blood and permeable to hydrogen ions and including a pH indicator located for response to said hydrogen ions; and said controller derives said total ammoniacal concentration value in correspondence with the expressions:

$$Ca(NH_4^+)=Ca(NH_3)/[10\ exp(pH-pKa)]$$

$$Ca=Ca(NH_3)+Ca(NH_4^+)$$

where: $Ca(NH_4^+)$ is the concentration of ammonium ions in blood, Ca ($NH_3$) is the measured concentration of ammonia gas in blood, pH is measured blood pH, pKa is the pH level of solution above which ammoniacal fluid exists only as a gas, and Ca is the total ammoniacal concentration in blood.

86. The system of claim 78 in which:

said catheter assembly has an outer principal cross-sectional dimension effective for insertion within said bloodstream at said peripheral region of said vascular system while avoiding generation of substantial hydraulic impedance to bloodflow.

87. The system of claim 86 in which said outer principal cross-sectional dimension is within a range of about 0.010 inch to 0.060 inch.

88. The system of claim 78 in which:
said ammoniacal component responsive forward assembly comprises:
an ammoniacal component concentration reactor having an output condition responsive to the concentration of said ammoniacal component in blood;
a membrane forming a blood confronting surface of said reactor, permeable to said ammoniacal component, said surface being contactable with blood within said bloodstream; and
said ammoniacal component sensor includes; a transmission assembly for conveying a signal corresponding with said output condition to said catheter proximal end region as said ammoniacal sensor output.

89. The system of claim 88 wherein:
said reactor comprises an ammoniacal component-sensitive fluorescent material having a fluorescence intensity as said output condition; and
said transmission component is a fiberoptic assembly for stimulating said reactor and conveying said fluorescence intensity as said ammoniacal sensor output.

90. The system of claim 88 wherein
said reactor comprises an ammoniacal component-sensitive fluorescent material stimulatable into fluorescence, the rate of quenching of said fluorescence being said output condition; and
said transmission component is a fiberoptic assembly for stimulating said reactor and conveying resultant generated light as said ammoniacal sensor output.

91. The system of claim 88 in which:
said ammoniacal component is ammonium;
said membrane is permeable to ammonium ion ($NH_4^+$);
said reactor comprises first and second electrodes immersed within an electrolyte sensitive to said ammonium ion; and
said transmission assembly comprises a potentiometric assembly coupled with said first and second electrodes.

92. The system of claim 88 in which:
said ammoniacal component is ammonium;
said membrane is permeable to ammonium ion ($NH_4^+$);
said reactor comprises first and second electrodes immersed within an electrolyte sensitive to said ammonium ion; and
said transmission assembly comprises a potentiometric assembly coupled with said first and second electrodes.

93. A system for monitoring the ammoniacal concentration in blood, such blood exhibiting a pH value, and being within a vascular system directing a bloodstream extending to a peripheral region of the body remotely disposed from the heart, comprising:
a catheter assembly having a proximal end region, a measurement region spaced therefrom extending to a tip, having a first sensor channel extending from said proximal region to said measurement region, said measurement region being adapted to be positionable within said bloodstream at said peripheral region;
an ammoniacal component sensor assembly, supported by said first sensor channel, having an ammoniacal component responsive forward assembly at said measurement region contactable with flowing blood within said bloodstream, said sensor assembly being controllable to provide an ammoniacal sensor output at said proximal end region;
a controller coupled to effect operational control of said ammoniacal component sensor assembly, and responsive to said ammoniacal sensor output for deriving an ammoniacal component parameter at repeating measurement intervals, responsive to said ammoniacal component parameter to derive a total ammoniacal concentration value and a display signal corresponding therewith, said controller including a time clock providing a time output;
said controller is responsive to said time output with the corresponding occurrence of said display signal to derive a time associated display signal; and
a display assembly responsive to said time associated display signal and a corresponding total ammoniacal concentration derived display signal to provide an associative display of each as a visible perceptible information output.

94. The system of claim 93 in which said catheter assembly measurement region is adapted to be located within said vascular system at said peripheral region.

95. The system of claim 93 in which said ammoniacal component sensor comprises:
a fiberoptic assembly extending within said first sensor channel from said catheter assembly proximal end region to a fiberoptic tip located at and forming a component of said forward assembly;
a membrane forming a component of said forward assembly, permeable to said ammoniacal component, having an outer surface contactable with said bloodstream and an inner surface spaced from said fiberoptic tip to define an equilibration cavity; and
including a light transmission and reception assembly optically coupled with said fiberoptic assembly at said proximal end region and controllable to derive said ammoniacal sensor output with respect to ammoniacal component at said equilibration cavity.

96. The system of claim 95 in which said membrane inner surface is light reflecting.

97. The system of claim 93 in which said ammoniacal component sensor comprises:
a fiberoptic assembly extending from said catheter proximal end region to a fiberoptic tip at said forward assembly, including an outer surface extending inwardly from said fiberoptic tip;
an end plug impervious to blood having an inwardly disposed surface spaced from said fiberoptic tip to define the length of an equilibration cavity;
a membrane permeable to said ammoniacal component having an outer surface contactable with said bloodstream, said membrane extending sealingly about said outer surface and said end plug to define the sides of said equilibration cavity.

98. The system of claim 93 in which said ammoniacal component sensor comprises:
a fiberoptic assembly extending from said catheter proximal end region to said forward assembly and having a forward light transmission leg and a return transmission leg spaced from said forward light transmission leg to define a gap situated at said forward assembly; and
a membrane permeable to said ammoniacal component, having an outer surface contactable with said bloodstream, said membrane sealingly extending about said gap to define an equilibration cavity.

99. The system of claim 93 in which:

said ammoniacal component is ammonia ($NH_3$);

said ammoniacal sensor output is provided in correspondence with the concentration of ammonia gas ($NH_3$) in said bloodstream; and said controller derives said total ammoniacal concentration value in correspondence with the expressions:

$$Ca(NH_4^+) = Ca(NH_3)/[10\ exp(pH-pKa)]$$

$$Ca = Ca(NH_3) + Ca(NH_4^+)$$

where: $Ca(NH_4^+)$ is the concentration of ammonium ions in blood, $Ca(NH_3)$ is the measured concentration of ammonia gas in blood, pH is measured blood pH, pKa is the pH level of solution above which ammoniacal fluid exists only as a gas, and Ca is the total ammoniacal concentration in blood.

100. The system of claim 93 in which:

said catheter assembly includes a second sensor channel extending from said proximal region to said measurement region;

including a pH sensor assembly supported by said second sensor channel, having a pH responsive forward assembly and a fiberoptic transmission component extending therefrom to said proximal region, said pH sensor assembly being controllable to provide a pH output at said proximal region;

said ammoniacal component is ammonia ($NH_3$); and said controller is responsive to control said pH sensor, and is responsive to said pH output to derive said total ammoniacal concentration value.

101. The system of claim 100 in which:

said pH sensor forward assembly includes a membrane impervious to blood and permeable to hydrogen ions and including a pH indicator located for response to said hydrogen ions; and said controller derives said total ammoniacal concentration value in correspondence with the expressions:

$$Ca(NH_4^+) = Ca(NH_3)/[10\ exp(pH-pKa)]$$

$$Ca = Ca(NH_3) + Ca(NH_4^+)$$

where: $Ca(NH_4^+)$ is the concentration of ammonium ions in blood, Ca ($NH_3$) is the measured concentration of ammonia gas in blood, pH is measured blood pH, pKa is the pH level of solution above which ammoniacal fluid exists only as a gas, and Ca is the total ammoniacal concentration in blood.

102. The system of claim 93 in which:

said catheter assembly has an outer principal cross-sectional dimension effective for insertion within said bloodstream at said peripheral region of said vascular system while avoiding generation of substantial hydraulic impedance to bloodflow.

103. The system of claim 102 in which said outer principal cross-sectional dimension is within a range of about 0.010 inch to 0.060 inch.

104. The system of claim 93 in which:

said ammoniacal component responsive forward assembly comprises:

an ammoniacal component concentration reactor having an output condition responsive to the concentration of said ammoniacal component in blood;

a membrane forming a blood confronting surface of said reactor, permeable to said ammoniacal component, said surface being contactable with blood within said bloodstream; and said ammoniacal component sensor includes; a transmission assembly for conveying a signal corresponding with said output condition to said catheter proximal end region as said ammoniacal sensor output.

105. The system of claim 104 wherein:

said reactor comprises an ammoniacal component-sensitive fluorescent material having a fluorescence intensity as said output condition; and said transmission component is a fiberoptic assembly for stimulating said reactor and conveying said fluorescence intensity as said ammoniacal sensor output.

106. The system of claim 104 wherein said reactor comprises an ammoniacal component-sensitive fluorescent material stimulatable into fluorescence, the rate of quenching of said fluorescence being said output condition; and said transmission component is a fiberoptic assembly for stimulating said reactor and conveying resultant generated light as said ammoniacal sensor output.

107. The system of claim 104 in which:

said ammoniacal component is ammonium;

said membrane is permeable to ammonium ion ($NH_4^+$);

said reactor comprises first and second electrodes immersed within an electrolyte sensitive to said ammonium ion; and said transmission assembly comprises a potentiometric assembly coupled with said first and second electrodes.

108. The system of claim 104 in which:

said ammoniacal component is ammonium;

said membrane is permeable to ammonium ion ($NH_4^+$);

said reactor comprises first and second electrodes immersed within an electrolyte sensitive to said ammonium ion; and said transmission assembly comprises a potentiometric assembly coupled with said first and second electrodes.

109. A system for monitoring the ammoniacal concentration in blood, such blood exhibiting a pH value, and being within a vascular system directing a bloodstream extending to a peripheral region of the body remotely disposed from the heart, comprising:

a catheter assembly having a proximal end region, a measurement region spaced therefrom extending to a tip, having a first sensor channel extending from said proximal region to said measurement region, said measurement region being adapted to be positionable within said bloodstream at said peripheral region;

an ammoniacal component sensor assembly, supported by said first sensor channel, having an ammoniacal component responsive forward assembly at said measurement region contactable with flowing blood within said bloodstream, said sensor assembly being controllable to provide an ammoniacal sensor output at said proximal end region, said ammoniacal component responsive forward assembly comprising:

an ammoniacal component concentration reactor having an output condition responsive to the concentration of said ammoniacal component in blood, a membrane forming a blood confronting surface of said reactor, permeable to said ammoniacal component, said surface being contactable with blood within said bloodstream, said ammoniacal component sensor including a transmission assembly for conveying a signal corresponding with said output condition to said catheter proximal end region as said ammoniacal sensor output, said ammoniacal component is ammonia ($NH_3$), said membrane is permeable to gaseous ammonia, said reactor is a gaseous ammonia sensitive dye, and said transmission assembly is a fiberoptic colorimetric measurement assembly which quantiates a change in color of the dye and is mounted within said first sensor channel;

a controller coupled to effect operational control of said ammoniacal component sensor assembly, and responsive to said ammoniacal sensor output for deriving an ammoniacal component parameter at repeating measurement intervals, responsive to said ammoniacal component parameter to derive a total ammoniacal concentration value and a display signal corresponding therewith, said controller additionally being responsive to said pH value to derive said total ammoniacal concentration value; and a display assembly responsive to said display signal to provide a visibly perceptible information output corresponding therewith.

110. The system of claim 109 in which:

said fiberoptic extends to a forward face positionable at said catheter tip for immersion within said bloodstream;

said gaseous ammonia sensitive dye is incorporated within said membrane; and said membrane is formed over said fiberoptic in intimate abutment with said fiberoptic forward face.

111. A system for monitoring the ammoniacal concentration in blood, such blood exhibiting a pH value, and being within a vascular system directing a bloodstream extending to a peripheral region of the body remotely disposed from the heart, comprising:

a catheter assembly having a proximal end region, a measurement region spaced therefrom extending to a tip, having a first sensor channel extending from said proximal region to said measurement region, said measurement region being adapted to be positionable within said bloodstream at said peripheral region;

an ammoniacal component sensor assembly, supported by said first sensor channel, having an ammoniacal component responsive forward assembly at said measurement region contactable with flowing blood within said bloodstream, said sensor assembly being controllable to provide an ammoniacal sensor output at said proximal end region, said ammoniacal component is ammonia ($NH_3$);

said ammoniacal component sensor further comprising a fiberoptic assembly within said first sensor channel having a forward face at said forward assembly adapted for direct light exchange communication with said bloodstream, said fiberoptic assembly being extensible to a light source and photoresponsive assembly for measuring the concentration of ammonia gas ($NH_3$) in the bloodstream and providing said ammoniacal sensor output;

a controller coupled to effect operational control of said ammoniacal component sensor assembly, and responsive to said ammoniacal sensor output for deriving an ammoniacal component parameter at repeating measurement intervals, responsive to said ammoniacal component parameter to derive a total ammoniacal concentration value and a display signal corresponding therewith, said controller being additionally responsive to said pH value to derive said total ammoniacal concentration value, and a display assembly responsive to said display signal to provide a visibly perceptible information output corresponding therewith.

112. A system for monitoring the ammoniacal concentration in blood, such blood exhibiting a pH value, and being within a vascular system directing a bloodstream extending to a peripheral region of the body remotely disposed from the heart, comprising:

a catheter assembly having a proximal end region, a measurement region spaced therefrom extending to a tip, having a first sensor channel extending from said proximal region to said measurement region, said measurement region being adapted to be positionable within said bloodstream at said peripheral region;

an ammoniacal component sensor assembly, supported by said first sensor channel, having an ammoniacal component responsive forward assembly at said measurement region contactable with flowing blood within said bloodstream, said sensor assembly being controllable to provide an ammoniacal sensor output at said proximal end region, said ammoniacal component responsive forward assembly comprising:

an ammoniacal component concentration reactor having an output condition responsive to the concentration of said ammoniacal component in blood, a membrane forming a blood confronting surface of said reactor, permeable to said ammoniacal component, said surface being contractable with blood within said bloodstream, said ammoniacal component sensor includes a transmission assembly for conveying a signal corresponding with said output condition to said catheter proximal end region as said ammoniacal sensor output, said ammoniacal component reactor being configured as Schottky diode array having a conductive polymer responsive to said ammoniacal component to effect a forward bias alternation as said ammoniacal sensor output;

a controller coupled to effect operational control of said ammoniacal component sensor assembly, and responsive to said ammoniacal sensor output for deriving an ammoniacal component parameter at repeating measurement intervals, responsive to said ammoniacal component parameter to derive a total ammoniacal concentration value and a display signal corresponding therewith, and a display assembly responsive to said display signal to provide a visibly perceptible information output corresponding therewith.

113. A system for monitoring the ammoniacal concentration in blood, such blood exhibiting a pH value, and being within a vascular system directing a bloodstream extending to a peripheral region of the body remotely disposed from the heart, comprising:

a catheter assembly having a proximal end region, a measurement region spaced therefrom extending to a tip, having a first sensor channel extending from said proximal region to said measurement region, said measurement region being adapted to be positionable within said bloodstream;

an ammoniacal component sensor assembly, supported by said first sensor channel, having an ammoniacal component responsive forward assembly at said measurement region contactable with flowing blood within said bloodstream, said sensor assembly being controllable to provide an ammoniacal sensor output at said proximal end region, said ammoniacal component sensor forward assembly being configured as a Schottky diode array having a conductive polymer responsive to said ammoniacal component to effect a forward bias alteration as said ammoniacal sensor output;

a controller coupled to effect operational control of said ammoniacal component sensor assembly, and responsive to said ammoniacal sensor output for deriving an ammoniacal component parameter at repeating measurement intervals, responsive to said ammoniacal component parameter to derive a total ammoniacal concentration value and a display signal corresponding therewith, and a display assembly responsive to said display signal to provide a visibly perceptible information output corresponding therewith.

114. A system for monitoring the ammoniacal concentration in blood, such blood exhibiting a pH value, and being within a vascular system directing a bloodstream extending to a peripheral region of the body remotely disposed from the heart, comprising:

a catheter assembly having a proximal end region, a measurement region spaced therefrom extending to a tip, having a first sensor channel extending from said proximal region to said measurement region, said measurement region being adapted to be positionable within said bloodstream;

an ammoniacal component sensor assembly, supported by said first sensor channel, having an ammoniacal component responsive forward assembly at said measurement region contactable with flowing blood within said bloodstream, said sensor assembly being controllable to provide an ammoniacal sensor output at said proximal end region, said ammoniacal component sensor forward assembly comprising an acoustic-wave sensor having an acoustic wave delay line within an oscillator loop to derive said ammoniacal sensor output as a frequency shift;

a controller coupled to effect operational control of said ammoniacal component sensor assembly, and responsive to said ammoniacal sensor output for deriving an ammoniacal component parameter at repeating measurement intervals, responsive to said ammoniacal component parameter to derive a total ammoniacal concentration value and a display signal corresponding therewith, and a display assembly responsive to said display signal to provide a visibly perceptible information output corresponding therewith.

115. A system for monitoring the ammoniacal concentration in blood, such blood exhibiting a pH value, and being within a vascular system directing a bloodstream extending to a peripheral region of the body remotely disposed from the heart, comprising:

a catheter assembly having a proximal end region, a measurement region spaced therefrom extending to a tip, having a first sensor channel extending from said proximal region to said measurement region, said measurement region being adapted to be positionable within said bloodstream at said peripheral region of said vascular system and including a second sensor channel extending from said proximal region to said measurement region;

an ammoniacal component sensor assembly, supported by said first sensor channel, having an ammoniacal component responsive forward assembly at said measurement region contactable with flowing blood within said bloodstream, said sensor assembly being controllable to provide an ammoniacal sensor output at said proximal end region, a pH sensor assembly supported by said second sensor channel, having a pH responsive forward assembly and a fiberoptic transmission component extending therefrom to said proximal region, said pH sensor assembly being controllable to provide a pH output at said proximal region;

said ammoniacal component is ammonia ($NH_3$);

a controller coupled to effect operational control of said ammoniacal component sensor assembly, and responsive to said ammoniacal sensor output for deriving an ammoniacal component parameter at repeating measurement intervals, responsive to control said pH sensor responsive to said ammoniacal component parameter and to said pH output to derive a total ammoniacal concentration value and a display signal corresponding therewith, said controller including an inputting assembly manually controllable to provide a total ammoniacal concentration threshold value, said controller being responsive to said total ammoniacal concentration threshold value to retain it in memory, said controller being responsive to a given said total ammoniacal concentration value and to said memory retained total ammoniacal concentration threshold value to derive an alarm signal when said given total ammoniacal concentration value is greater than said memory retained total ammoniacal concentration threshold value, and a display assembly responsive to said display signal to provide a visibly perceptible information output corresponding therewith, and responsive to said alarm signal to provide a perceptible alarm output signal.

116. A system for monitoring the ammoniacal concentration in blood, such blood exhibiting a pH value, and being within a vascular system directing a bloodstream extending to a peripheral region of the body remotely disposed from the heart, comprising:

a catheter assembly having a proximal end region, a measurement region spaced therefrom extending to a tip, having a first sensor channel extending from said proximal region to said measurement region, said measurement region being adapted to be positionable within said blood stream at said peripheral region, and including a second sensor channel extending from said proximal region to said measurement region;

an ammoniacal component sensor assembly, supported by said first sensor channel, having an ammoniacal component responsive forward assembly at said measurement region contactable with flowing blood within said bloodstream, said sensor assembly being controllable to provide an ammoniacal sensor output at said proximal end region, a pH sensor assembly supported by said second sensor channel, having a pH responsive forward assembly and a fiberoptic transmission component extending therefrom to said proximal region, said pH sensor assembly being controllable to provide a pH output at said proximal region;

said ammoniacal component is ammonia ($NH_3$);

a controller coupled to effect operational control of said ammoniacal component sensor assembly and said pH sensor, and responsive to said ammoniacal sensor output for deriving an ammoniacal component parameter at repeating measurement intervals, responsive to said ammoniacal component parameter and to said pH output to derive a total ammoniacal concentration value and a display signal corresponding therewith, said controller including an inputting assembly manually controllable to provide a rate of change of ammoniacal concentration threshold value, said controller being responsive to a given said total ammoniacal concentration value and to a previous such concentration value to derive a current total ammoniacal concentration rate of change value, and responsive to said rate of change of total ammoniacal concentration threshold value and to said current total ammoniacal concentration rate of change value to derive an alarm signal when said current total ammoniacal concentration rate of change value is greater than said rate of change of total ammoniacal concentration threshold value; and a display assembly responsive to said display signal to provide a visibly perceptible information output corresponding therewith, and responsive to said alarm signal to provide a perceptible alarm output.

117. A system for monitoring the ammoniacal concentration in blood, such blood exhibiting a pH value, and being within a vascular system directing a bloodstream extending to a peripheral region of the body remotely disposed from the heart, comprising:

a catheter assembly having a proximal end region, a measurement region spaced therefrom extending to a tip, having a first sensor channel extending from said proximal region to said measurement region, said measurement region being adapted to be positionable within said bloodstream at said peripheral region, and including a second sensor channel extending from said proximal region to said measurement region;

an ammoniacal component sensor assembly, supported by said first sensor channel, having an ammoniacal component responsive forward assembly at said measurement region contactable with flowing blood within said bloodstream, said sensor assembly being controllable to provide an ammoniacal sensor output at said proximal end region, a pH sensor assembly supported by said second sensor channel, having a pH responsive forward assembly and a fiberoptic transmission component extending therefrom to said proximal region, said pH sensor assembly being controllable to provide a pH output at said proximal region;

said ammoniacal component is ammonia ($NH_3$);

a controller coupled to effect operational control of said ammoniacal component sensor assembly and said pH sensor assembly, and responsive to said ammoniacal sensor output for deriving an ammoniacal component parameter at repeating measurement intervals, responsive to said ammoniacal component parameter and to said pH output to derive a total ammoniacal concentration value and a display signal corresponding therewith, responsive to a first said total ammoniacal concentration value and responsive to a second said total ammoniacal concentration value derived subsequent to said first total ammoniacal concentration value, and responsive to derive a warning signal when said second total ammoniacal concentration value is greater than said first total ammoniacal concentration value; and a display assembly responsive to said display signal to provide a visibly perceptible information output corresponding therewith, and responsive to said warning signal to provide a perceptible warning output.

118. A system for monitoring the ammoniacal concentration in blood, such blood exhibiting a pH value, and being within a vascular system directing a bloodstream extending to a peripheral region of the body remotely disposed from the heart, comprising:

a catheter assembly having a proximal end region, a measurement region spaced therefrom extending to a tip, having a first sensor channel extending from said proximal region to said measurement region, said measurement region being adapted to be positionable within said bloodstream at said peripheral region, and including a second sensor channel extending from said proximal region to said measurement region;

an ammoniacal component sensor assembly, supported by said first sensor channel, having an ammoniacal component responsive forward assembly at said measurement region contactable with flowing blood within said bloodstream, said sensor assembly being controllable to provide an ammoniacal sensor output at said proximal end region, a pH sensor assembly supported by said second sensor channel, having a pH responsive forward assembly and a fiberoptic transmission component extending therefrom to said proximal region, said pH sensor assembly being controllable to provide a pH output at said proximal region;

said ammoniacal component is ammonia ($NH_3$);

a controller coupled to effect operational control of said ammoniacal component sensor assembly and said pH sensor, and responsive to said ammoniacal sensor output for deriving an ammoniacal component parameter at repeating measurement intervals, responsive to said ammoniacal component parameter and to said pH output to derive a total ammoniacal concentration value and a display signal corresponding therewith, said controller including a time clock providing a time output, and being responsive to said real time output with the contemporaneous derived occurrence of said total ammoniacal concentration value to derive a time associated display signal; and a display assembly responsive to said display signal to provide a visibly perceptible information output corresponding therewith, and responsive to each of a sequence said of said time associated display signals to publish a trend defining graphics display thereof.

119. A system for monitoring the ammoniacal concentration in blood, such blood exhibiting a pH value, and being within a vascular system directing a bloodstream extending to a peripheral region of the body remotely disposed from the heart, comprising:

catheter assembly comprising:

a first catheter having a first proximal region, a first measurement region spaced therefrom extending to a first tip, having an outer first principal cross-sectional dimension effective for insertion within said bloodstream at said peripheral region while avoiding generation of substantial hydraulic impedance to blood flow, said first catheter having a first sensor channel, said first sensor channel extending from said first proximal region to said first measurement region, and a second catheter having a second proximal region, a second measurement region spaced therefrom extending to a second tip, having an outer second principal cross-sectional dimension effective for insertion within said bloodstream, in spaced relationship from said first catheter at said peripheral region while avoiding generation of substantial hydraulic impedance to blood flow, said second catheter having a second sensor channel, said second sensor channel extending from said second proximal region to a said second measurement region;

an ammoniacal component sensor assembly, supported by said first sensor channel, having an ammoniacal component responsive forward assembly at said first measurement region contactable with flowing blood within said bloodstream, said sensor assembly being controllable to provide an ammoniacal sensor output at said first proximal end region, said ammoniacal component is ammonia ($NH_3$);

said ammoniacal component sensor assembly ammoniacal component forward assembly is an ammonia sensor forward assembly, said sensor assembly being controllable to provide said ammoniacal sensor output as an ammonia sensor output;

a pH sensor assembly supported by said second sensor channel, having a pH responsive forward assembly and a fiberoptic transmission component extending therefrom to said second proximal region, said pH sensor assembly being controllable to provide a pH output at said second proximal region; and a controller coupled to effect operational control of said ammoniacal component sensor assembly and said pH sensor assembly, and responsive to said ammoniacal sensor output for deriving an ammoniacal component parameter at repeating measurement intervals, responsive to said ammoniacal component parameter and to said pH output to derive a total ammoniacal concentration value and deriving a display signal corresponding with said total ammoniacal concentration value; and a display assembly responsive to said display signal to provide a visibly perceptible information output corresponding therewith.

120. The system of claim 119 in which said first and second outer principal cross-sectional dimensions are within a range of about 0.010 inch to 0.060 inch.

121. The method for monitoring the ammoniacal concentration in blood within the vascular system contained bloodstream of the body, such system directing blood exhibiting a given pH value along given path directions and extending to peripheral regions of such body without the immediate region of the heart, comprising the steps of:

(a) providing a catheter assembly having a proximal end region, a measurement region spaced therefrom extending to a tip, having a first sensor channel extending from said proximal region to said measurement region, an ammoniacal component sensor supported by said first sensor channel, having an ammoniacal component responsive forward assembly at said measurement region contactable with flowing blood within said bloodstream, said sensor assembly being controllable to provide ammoniacal sensor outputs at said proximal end region;

(b) providing a controller actuable to control said ammoniacal component sensor assembly to derive said ammoniacal sensor outputs over a sequence of measurement intervals, and responsive to said ammoniacal sensor outputs to derive a sequence of total ammoniacal concentration values over a measurement period and deriving display signals corresponding with said sequence of values, said controller further being responsive to said total ammoniacal concentration values and to a memory retained total ammoniacal concentration threshold value to derive an alarm signal when one of said total ammoniacal concentration values is greater than or equal to said memory retained total ammoniacal concentration threshold value;

(c) providing a display assembly responsive to said display signals to derive a visibly perceptible information output corresponding therewith, and responsive to said alarm signal to provide a perceptible alarm output;

(d) positioning said catheter assembly measurement region within said bloodstream at one of said peripheral regions; and (e) actuating said controller to derive said display signals and effect derivation of said perceptible information output, including the step of:
   inputting to said memory of said controller said ammoniacal concentration threshold value.

122. The method of claim 121 in which:

said step (d) positions said catheter assembly measurement region within said blood supply in a manner wherein said tip is in confronting relationship with respect to one of said given path directions of said directed blood.

123. The method of claim 121 in which:

said step (a) provides said catheter assembly ammoniacal component responsive forward assembly as being responsive to an ammonia ($NH_3$) ammoniacal component; and said step (b) provides said controller as being responsive to said ammoniacal sensor outputs and to said given pH value to derive said total ammoniacal concentration values in correspondence with the expressions:

$$Ca(NH_4^+)=Ca(NH_3)/[10 \exp(pH-pKa)]$$

$$Ca=Ca(NH_3)+Ca(NH_4^+)$$

where: Ca ($NH_4^+$) is the concentration of ammonium ions in blood, Ca ($NH_3$) is the measured concentration of ammonia gas in blood, pH is measured blood pH, pKa is the pH level of solution above which ammoniacal fluid exists only as a gas, and Ca is the total ammoniacal concentration in blood.

124. The method of claim 121, in which:

said step (a) provides said catheter assembly ammoniacal component sensor as being responsive to an ammonia gas ($NH_3$) ammoniacal component, said ammoniacal component sensor including a fiberoptic assembly within said first sensor channel having a forward face at said measurement region adapted for direct light exchange communication with said bloodstream, said fiberoptic assembly being extensible to a light source and photoresponsive assembly for deriving said ammoniacal sensor outputs or concentrations of ammonia gas in said bloodstream; and said step (b) provides said controller as being responsive to said ammoniacal sensor outputs and to said given pH value to derive said total ammoniacal concentration values.

125. The method of claim 121 in which:
said step (a) provides said catheter assembly as having an outer principal cross-sectional dimension effective for insertion within said bloodstream at one of said peripheral regions of said vascular system while avoiding generation of substantial hydraulic impedance to bloodflow.

126. The method of claim 125 wherein said step (a) provides said catheter assembly as having a said outer principal cross-sectional dimension within a range of about 0.018 inch to 0.060 inch.

127. The method of claim 121 in which:
said step (a) provides said catheter assembly as comprising:
  a first catheter, having an outer first principal cross-sectional dimension effective for insertion within said bloodstream at said peripheral region of said vascular system while avoiding generation of substantial hydraulic impedance to bloodflow, said first catheter having said first sensor channel and said ammoniacal component sensor is responsive to an ammonia ($NH_3$) ammoniacal component and deriving said ammoniacal sensor outputs as concentrations of ammonia gas in said bloodstream, and
  a second catheter, having an outer second principal cross-sectional dimension effective for insertion within said bloodstream at said peripheral region of said vascular system while avoiding generation of substantial hydraulic impedance to bloodflow, said second catheter having a second sensor channel extending from a second proximal region to a second measurement region extending to a second tip, said second catheter having a pH sensor assembly supported by said second sensor channel, having a second forward assembly which is pH responsive and said pH sensor assembly being controllable to provide a pH output at said second proximal region;
said step (b) provides said controller as actuable to control said ammoniacal component sensor of said first catheter and said pH sensor assembly of said second catheter to respectively derive said ammoniacal sensor outputs and said pH output and is responsive to said ammoniacal sensor outputs and to said pH output to derive said sequence of total ammoniacal concentration values; and
said step (b) includes the steps of:
  (b1) positioning said first catheter measurement region within said bloodstream at one of said peripheral regions, and
  (b2) positioning said second catheter second measurement region at one of said peripheral regions in spaced relationship from said first catheter.

128. The method of claim 127 in which said step (a) provides said outer first principal cross-sectional dimension and said outer second principal cross-sectional dimension as being less than about 0.18 inch.

129. The method for monitoring the ammoniacal concentration in blood within the vascular system contained bloodstream of the body, such system directing blood exhibiting a given pH value along given path directions and extending to peripheral regions of such body without the immediate region of the heart, comprising the steps of:
(a) providing a catheter assembly having a proximal end region, a measurement region spaced therefrom extending to a tip, having a first sensor channel extending from said proximal region to said measurement region, an ammoniacal component sensor supported by said first sensor channel, having an ammoniacal component responsive forward assembly at said measurement region contactable with flowing blood within said bloodstream, said sensor assembly being controllable to provide ammoniacal sensor outputs at said proximal end region;
(b) providing a controller actuable to control said ammoniacal component sensor assembly to derive said ammoniacal sensor outputs over a sequence of measurement intervals, and responsive to said ammoniacal sensor outputs to derive a sequence of total ammoniacal concentration values over a measurement period and deriving display signals corresponding with said sequence of values, said controller being responsive to a first one of said total ammoniacal concentration values and being responsive to a second one of said total ammoniacal concentration value derived subsequent to said first one of said total ammoniacal concentration values and being responsive to derive a warning signal when said second one of said ammoniacal concentration values is greater than said first one of said ammoniacal concentration values;
(c) providing a display assembly responsive to said display signals to derive a visibly perceptible information output corresponding therewith, and responsive to said warning signal to provide a perceptible warning output;
(d) positioning said catheter assembly measurement region within said bloodstream at one of said peripheral regions; and
(e) actuating said controller to derive said display signals and effect derivation of said perceptible information output.

130. The method of claim 129 in which:
said step (d) positions said catheter assembly measurement region within said blood supply in a manner wherein said tip is in confronting relationship with respect to one of said given path directions of said directed blood.

131. The method of claim 129 in which:
said step (a) provides said catheter assembly ammoniacal component responsive forward assembly as being responsive to an ammonia ($NH_3$) ammoniacal component; and
said step (b) provides said controller as being responsive to said ammoniacal sensor outputs and to said given pH value to derive said total ammoniacal concentration values in correspondence with the expressions:

$$Ca(NH_4^+) = Ca(NH_3)/[10\ exp(pH-pKa)]$$

$$Ca = Ca(NH_3) + Ca(NH_4^+)$$

where: Ca ($NH_4^+$) is the concentration of ammonium ions in blood, Ca ($NH_3$) is the measured concentration of ammonia gas in blood, pH is measured blood pH, pKa is the pH level of solution above which ammoniacal fluid exists only as a gas, and Ca is the total ammoniacal concentration in blood.

132. The method of claim 129 in which:
said step (a) provides said catheter assembly ammoniacal component sensor as being responsive to an ammonia gas ($NH_3$) ammoniacal component, said ammoniacal component sensor including a fiberoptic assembly within said first sensor channel having a forward face at said measurement region adapted for direct light exchange communication with said bloodstream, said fiberoptic assembly being extensible to a light source and photoresponsive assembly for deriving said ammoniacal sensor outputs or concentrations of ammonia gas in said bloodstream; and said step (b) providers provides said controller or as being responsive to said ammoniacal sensor outputs and to said given pH value to derive said total ammoniacal concentration values.

133. The method of claim 129 in which:

said step (a) provides said catheter assembly as having an outer principal cross-sectional dimension effective for insertion within said bloodstream at one of said peripheral regions of said vascular system while avoiding generation of substantial hydraulic impedance to bloodflow.

134. The method of claim 133 wherein said step (a) provides said catheter assembly as having a said outer principal cross-sectional dimension within a range of about 0.018 inch to 0.060 inch.

135. The method of claim 129 in which:

said step (a) provides said catheter assembly as comprising:
  a first catheter, having an outer first principal cross-sectional dimension effective for insertion within said bloodstream at said peripheral region of said vascular system while avoiding generation of substantial hydraulic impedance to bloodflow, said first catheter having said first sensor channel and said ammoniacal component sensor is responsive to an ammonia (NH3) ammoniacal component and deriving said ammoniacal sensor outputs as concentrations of ammonia gas in said bloodstream, and
  a second catheter, having an outer second principal cross-sectional dimension effective for insertion within said bloodstream at said peripheral region of said vascular system while avoiding generation of substantial hydraulic impedance to bloodflow, said second catheter having a second sensor channel extending from a second proximal region to a second measurement region extending to a second tip, said second catheter having a pH sensor assembly supported by said second sensor channel, having a second forward assembly which is pH responsive and said pH sensor assembly being controllable to provide a pH output at said second proximal region;

said step (b) provides said controller as actuable to control said ammoniacal component sensor of said first catheter and said pH sensor assembly of said second catheter to respectively derive said ammoniacal sensor outputs and said pH output and is responsive to said ammoniacal sensor outputs and to said pH output to derive said sequence of total ammoniacal concentration values; and said step (b) includes the steps of:
  (b1) positioning said first catheter measurement region within said bloodstream at one of said peripheral regions, and
  (b2) positioning said second catheter second measurement region at one of said peripheral regions in spaced relationship from said first catheter.

136. The method of claim 135 in which said step (a) provides said outer first principal cross-sectional dimension and said outer second principal cross-sectional dimension as being less than about 0.18 inch.

137. The method for monitoring the ammoniacal concentration in blood within the vascular system contained bloodstream of the body, such system directing blood exhibiting a given pH value along given path directions and extending to peripheral regions of such body without the immediate region of the heart, comprising the steps of:

(a) providing a catheter assembly having a proximal end region, a measurement region spaced therefrom extending to a tip, having a first sensor channel extending from said proximal region to said measurement region, an ammoniacal component sensor supported by said first sensor channel, having an ammoniacal component responsive forward assembly at said measurement region contactable with flowing blood within said bloodstream, said sensor assembly being controllable to provide ammoniacal sensor outputs at said proximal end region;

(b) providing a controller actuable to control said ammoniacal component sensor assembly to derive said ammoniacal sensor outputs over a sequence of measurement intervals, and responsive to said ammoniacal sensor outputs to derive a sequence of total ammoniacal concentration values over a measurement period and deriving display signals corresponding with said sequence of values,
  said controller including a time clock providing a time output, and being responsive to said time output with the contemporaneous derived occurrence of one of said display signals to derive a time associated display signal;

(c) providing a display assembly responsive to said display signals to derive a visibly perceptible information output corresponding therewith, said display assembly being responsive to each of a sequence of said time associated display signals to produce a trend defining graphics display thereof;

(d) positioning said catheter assembly measurement region within said bloodstream at one of said peripheral regions; and (e) actuating said controller to derive said display signals and said time associated display signals and effect derivation of said perceptible information output with said trend defining graphics display.

138. The method of claim 137 in which:

said step (d) positions said catheter assembly measurement region within said blood supply in a manner wherein said tip is in confronting relationship with respect to one of said given path directions of said directed blood.

139. The method of claim 137 in which:

said step (a) provides said catheter assembly ammoniacal component responsive forward assembly as being responsive to an ammonia (NH$_3$) ammoniacal component; and said step (b) provides said controller as being responsive to said ammoniacal sensor outputs and to said given pH value to derive said total ammoniacal concentration values in correspondence with the expressions:

$$Ca(NH_4^+) = Ca(NH_3)/[10\ exp(pH-pKa)]$$

$$Ca = Ca(NH_3) + Ca(NH_4^+)$$

where: Ca (NH$_4^+$) is the concentration of ammonium ions in blood, Ca (NH$_3$) is the measured concentration of ammonia gas in blood, pH is measured blood pH, pKa is the pH level of solution above which ammoniacal fluid exists only as a gas, and Ca is the total ammoniacal concentration in blood.

140. The method of claim 137 in which:
said step (a) provides said catheter assembly ammoniacal component sensor as being responsive to an ammonia gas ($NH_3$) ammoniacal component, said ammoniacal component sensor including a fiberoptic assembly within said first sensor channel having a forward face at said measurement region adapted for direct light exchange communication with said bloodstream, said fiberoptic assembly being extensible to a light source and photoresponsive assembly for deriving said ammoniacal sensor outputs or concentrations of ammonia gas in said bloodstream; and
said step (b) providers provides said controller or as being responsive to said ammoniacal sensor outputs and to said given pH value to derive said total ammoniacal concentration values.

141. The method of claim 137 in which:
said step (a) provides said catheter assembly as having an outer principal cross-sectional dimension effective for insertion within said bloodstream at one of said peripheral regions of said vascular system while avoiding generation of substantial hydraulic impedance to bloodflow.

142. The method of claim 141 wherein said step (a) provides said catheter assembly as having a said outer principal cross-sectional dimension within a range of about 0.018 inch to 0.060 inch.

143. The method of claim 137 in which:
said step (a) provides said catheter assembly as comprising:
a first catheter, having an outer first principal cross-sectional dimension effective for insertion within said bloodstream at said peripheral region of said vascular system while avoiding generation of substantial hydraulic impedance to bloodflow, said first catheter having said first sensor channel and said ammoniacal component sensor is responsive to an ammonia (NH3) ammoniacal component and deriving said ammoniacal sensor outputs as concentrations of ammonia gas in said bloodstream, and
a second catheter, having an outer second principal cross-sectional dimension effective for insertion within said bloodstream at said peripheral region of said vascular system while avoiding generation of substantial hydraulic impedance to bloodflow, said second catheter having a second sensor channel extending from a second proximal region to a second measurement region extending to a second tip, said second catheter having a pH sensor assembly supported by said second sensor channel, having a second forward assembly which is pH responsive and said pH sensor assembly being controllable to provide a pH output at said second proximal region;
said step (b) provides said controller as actuable to control said ammoniacal component sensor of said first catheter and said pH sensor assembly of said second catheter to respectively derive said ammoniacal sensor outputs and said pH output and is responsive to said ammoniacal sensor outputs and to said pH output to derive said sequence of total ammoniacal concentration values; and
said step (b) includes the steps of:
(b1) positioning said first catheter measurement region within said bloodstream at one of said peripheral regions, and
(b2) positioning said second catheter second measurement region at one of said peripheral regions in spaced relationship from said first catheter.

144. The method of claim 143 in which said step (a) provides said outer first principal cross-sectional dimension and said outer second principal cross-sectional dimension as being less than about 0.18 inch.

145. The method for monitoring the ammoniacal concentration in blood within the vascular system contained bloodstream of the body, such system directing blood exhibiting a given pH value along given path directions and extending to peripheral regions of such body without the immediate region of the heart, comprising the steps of:
(a) providing a catheter assembly having a proximal end region, a measurement region spaced therefrom extending to a tip, having a first sensor channel extending from said proximal region to said measurement region, an ammoniacal component sensor supported by said first sensor channel, having an ammoniacal component responsive forward assembly at said measurement region contactable with flowing blood within said bloodstream, said sensor assembly being controllable to provide ammoniacal sensor outputs at said proximal end region;
(b) providing a controller actuable to control said ammoniacal component sensor assembly to derive said ammoniacal sensor outputs over a sequence of measurement intervals, and responsive to said ammoniacal sensor outputs to derive a sequence of total ammoniacal concentration values over a measurement period and deriving display signals corresponding with said sequence of values, said controller including a time clock providing a time output, and being responsive to said time output and the occurrence of a derived ones of said display signals to derive associated time of occurrence display signals;
(c) providing a display assembly responsive to said display signals and said associated time of occurrence display signals to provide visually perceptible representations of each as a visibly perceptible information output;
(d) positioning said catheter assembly measurement region within said bloodstream at one of said peripheral regions; and
(e) actuating said controller to derive said display signals and associated time of occurrence display signals and effect derivation of said perceptible information output.

146. The method of claim 145 in which:
said step (d) positions said catheter assembly measurement region within said blood supply in a manner wherein said tip is in confronting relationship with respect to one of said given path directions of said directed blood.

147. The method of claim 145 in which:
said step (a) provides said catheter assembly ammoniacal component responsive forward assembly as being responsive to an ammonia ($NH_3$) ammoniacal component; and
said step (b) provides said controller as being responsive to said ammoniacal sensor outputs and to said given pH value to derive said total ammoniacal concentration values in correspondence with the expressions:

$$Ca(NH_4^+) = Ca(NH_3)/[10\ exp(pH-pKa)]$$

$$Ca = Ca(NH_3) + Ca(NH_4^+)$$

where: Ca ($NH_4^+$) is the concentration of ammonium ions in blood, Ca ($NH_3$) is the measured concentration of ammonia gas in blood, pH is measured blood pH, pKa is the pH level of solution above which ammoniacal fluid exists only as a gas, and Ca is the total ammoniacal concentration in blood.

148. The method of claim 145 in which:
said step (a) provides said catheter assembly ammoniacal component sensor as being responsive to an ammonia gas ($NH_3$) ammoniacal component, said ammoniacal component sensor including a fiberoptic assembly within said first sensor channel having a forward face at said measurement region adapted for direct light exchange communication with said bloodstream, said fiberoptic assembly being extensible to a light source and photoresponsive assembly for deriving said ammoniacal sensor outputs or concentrations of ammonia gas in said bloodstream; and
said step (b) providers provides said controller or as being responsive to said ammoniacal sensor outputs and to said given pH value to derive said total ammoniacal concentration values.

149. The method of claim 145 in which:
said step (a) provides said catheter assembly as having an outer principal cross-sectional dimension effective for insertion within said bloodstream at one of said peripheral regions of said vascular system while avoiding generation of substantial hydraulic impedance to bloodflow.

150. The method of claim 149 wherein said step (a) provides said catheter assembly as having a said outer principal cross-sectional dimension within a range of about 0.018 inch to 0.060 inch.

151. The method of claim 145 in which:
said step (a) provides said catheter assembly as comprising:
a first catheter, having an outer first principal cross-sectional dimension effective for insertion within said bloodstream at said peripheral region of said vascular system while avoiding generation of substantial hydraulic impedance to bloodflow, said first catheter having said first sensor channel and said ammoniacal component sensor is responsive to an ammonia (NH3) ammoniacal component and deriving said ammoniacal sensor outputs as concentrations of ammonia gas in said bloodstream, and
a second catheter, having an outer second principal cross-sectional dimension effective for insertion within said bloodstream at said peripheral region of said vascular system while avoiding generation of substantial hydraulic impedance to bloodflow, said second catheter having a second sensor channel extending from a second proximal region to a second measurement region extending to a second tip, said second catheter having a pH sensor assembly supported by said second sensor channel, having a second forward assembly which is pH responsive and said pH sensor assembly being controllable to provide a pH output at said second proximal region;
said step (b) provides said controller as actuable to control said ammoniacal component sensor of said first catheter and said pH sensor assembly of said second catheter to respectively derive said ammoniacal sensor outputs and said pH output and is responsive to said ammoniacal sensor outputs and to said pH output to derive said sequence of total ammoniacal concentration values; and
said step (b) includes the steps of:
(b1) positioning said first catheter measurement region within said bloodstream at one of said peripheral regions, and
(b2) positioning said second catheter second measurement region at one of said peripheral regions in spaced relationship from said first catheter.

152. The method of claim 151 in which said step (a) provides said outer first principal cross-sectional dimension and said outer second principal cross-sectional dimension as being less than about 0.18 inch.

153. The method for monitoring the ammoniacal concentration in blood within the vascular system contained bloodstream of the body, such system directing blood exhibiting a given pH value along given path directions and extending to peripheral regions of such body without the immediate region of the heart, comprising the steps of:
(a) providing a catheter assembly having a proximal end region, a measurement region spaced therefrom extending to a tip, having a first sensor channel extending from said proximal region to said measurement region, an ammoniacal component sensor supported by said first sensor channel, having an ammoniacal component responsive forward assembly at said measurement region contactable with flowing blood within said bloodstream, said sensor assembly being controllable to provide ammoniacal sensor outputs at said proximal end region;
(b) providing a controller actuable to control said ammoniacal component sensor assembly to derive said ammoniacal sensor outputs over a sequence of measurement intervals, and responsive to said ammoniacal sensor outputs to derive a sequence of total ammoniacal concentration values over a measurement period and deriving display signals corresponding with said sequence of values, said controller being responsive to a given one of said total ammoniacal concentration values and to a previous such concentration value to derive a current total ammoniacal concentration rate of change value, and being responsive to said rate of change of total ammoniacal concentration threshold value and to said current total ammoniacal concentration rate of change value to derive an alarm signal when said current total ammoniacal concentration rate of change value is greater than said rate of change of total ammoniacal concentration threshold value;
(c) providing a display assembly responsive to said display signals to derive a visibly perceptible information output corresponding therewith, and responsive to said alarm signal to provide a perceptible alarm output;
(d) positioning said catheter assembly measurement region within said bloodstream at one of said peripheral regions; and
(e) actuating said controller to derive said display signals and effect derivation of said perceptible information output, including the step of inputting to said controller assembly a rate of change of total ammoniacal concentration threshold value.

154. The method for monitoring the ammoniacal concentration in blood within the vascular system contained bloodstream of the body, such system directing blood exhibiting a given pH value along given path directions and extending to peripheral regions of such body without the immediate region of the heart, comprising the steps of:
(a) providing a catheter assembly having a proximal end region, a measurement region spaced therefrom extending to a tip, having a first sensor channel extending from said proximal region to said measurement region, an ammoniacal component sensor supported by said first sensor channel, having an ammoniacal component responsive forward assembly at said measurement region contactable with flowing blood within said bloodstream, said sensor assembly being controllable to provide ammoniacal sensor outputs at said proximal end region;

(b) providing a controller actuable to control said ammoniacal component sensor assembly to derive said ammoniacal sensor outputs over a sequence of measurement intervals, and responsive to said ammoniacal sensor outputs to derive a sequence of total ammoniacal concentration values over a measurement period and deriving display signals corresponding with said sequence of values, said controller being responsive to retain said total ammoniacal concentration values in memory, being responsive to a given one of said total ammoniacal concentration value and n−1 memory retained previously occurring said total ammoniacal concentration values to derive a filtered total ammoniacal concentration value representing the moving average filtering of n of said total ammoniacal concentration values and provided as one of said display signals;

(c) providing a display assembly responsive to said display signals to derive a visibly perceptible information output corresponding therewith;

(d) positioning said catheter assembly measurement region within said bloodstream at one of said peripheral regions; and (e) actuating said controller to derive said display signals and effect derivation of said perceptible information output.

155. The method of claim 154 in which:
said step (d) positions said catheter assembly measurement region within said blood supply in a manner wherein said tip is in confronting relationship with respect to one of said given path directions of said directed blood.

156. The method of claim 154 in which:
said step (a) provides said catheter assembly ammoniacal component responsive forward assembly as being responsive to an ammonia ($NH_3$) ammoniacal component; and
said step (b) provides said controller as being responsive to said ammoniacal sensor outputs and to said given pH value to derive said total ammoniacal concentration values in correspondence with the expressions:

$Ca(NH_4^+)=Ca(NH_3)/[10\ exp(pH-pKa)]$ $Ca=Ca(NH_3)+Ca(NH_4^+)$ where: Ca ($NH_4^+$) is the concentration of ammonium ions in blood, Ca ($NH_3$) is the measured concentration of ammonia gas in blood, pH is measured blood pH, pKa is the pH level of solution above which ammoniacal fluid exists only as a gas, and Ca is the total ammoniacal concentration in blood.

157. The method of claim 154 in which:
said step (a) provides said catheter assembly ammoniacal component sensor as being responsive to an ammonia gas ($NH_3$) ammoniacal component, said ammoniacal component sensor including a fiberoptic assembly within said first sensor channel having a forward face at said measurement region adapted for direct light exchange communication with said bloodstream, said fiberoptic assembly being extensible to a light source and photoresponsive assembly for deriving said ammoniacal sensor outputs or concentrations of ammonia gas in said bloodstream; and said step (b) providers provides said controller or as being responsive to said ammoniacal sensor outputs and to said given pH value to derive said total ammoniacal concentration values.

158. The method of claim 154 in which:
said step (a) provides said catheter assembly as having an outer principal cross-sectional dimension effective for insertion within said bloodstream at one of said peripheral regions of said vascular system while avoiding generation of substantial hydraulic impedance to bloodflow.

159. The method of claim 158 wherein said step (a) provides said catheter assembly as having a said outer principal cross-sectional dimension within a range of about 0.018 inch to 0.060 inch.

160. The method of claim 154 in which:
said step (a) provides said catheter assembly as comprising:
a first catheter, having an outer first principal cross-sectional dimension effective for insertion within said bloodstream at said peripheral region of said vascular system while avoiding generation of substantial hydraulic impedance to bloodflow, said first catheter having said first sensor channel and said ammoniacal component sensor is responsive to an ammonia (NH3) ammoniacal component and deriving said ammoniacal sensor outputs as concentrations of ammonia gas in said bloodstream, and
a second catheter, having an outer second principal cross-sectional dimension effective for insertion within said bloodstream at said peripheral region of said vascular system while avoiding generation of substantial hydraulic impedance to bloodflow, said second catheter having a second sensor channel extending from a second proximal region to a second measurement region extending to a second tip, said second catheter having a pH sensor assembly supported by said second sensor channel, having a second forward assembly which is pH responsive and said pH sensor assembly being controllable to provide a pH output at said second proximal region;
said step (b) provides said controller as actuable to control said ammoniacal component sensor of said first catheter and said pH sensor assembly of said second catheter to respectively derive said ammoniacal sensor outputs and said pH output and is responsive to said ammoniacal sensor outputs and to said pH output to derive said sequence of total ammoniacal concentration values; and
said step (b) includes the steps of:
(b1) positioning said first catheter measurement region within said bloodstream at one of said peripheral regions, and
(b2) positioning said second catheter second measurement region at one of said peripheral regions in spaced relationship from said first catheter.

161. The method of claim 160 in which said step (a) provides said outer first principal cross-sectional dimension and said outer second principal cross-sectional dimension as being less than about 0.18 inch.

162. The method for monitoring the ammoniacal concentration in blood within the vascular system contained bloodstream of the body, such system directing blood exhibiting a given pH value along given path directions and extending to peripheral regions of such body without the immediate region of the heart, comprising the steps of:
(a) providing a catheter assembly having a proximal end region, a measurement region spaced therefrom extending to a tip, having a first sensor channel extending from said proximal region to said measurement region, an ammoniacal component sensor supported by said first sensor channel, having an ammoniacal component responsive forward assembly at said measurement region contactable with flowing blood within said bloodstream, said sensor assembly being controllable to provide ammoniacal sensor outputs at said proximal end region, said catheter assembly ammoniacal component sensor being responsive to an ammonia ($NH_3$) ammoniacal component, said ammoniacal component sensor including a fiberoptic colorimetric measurement assembly which quantiates a change in color and is mounted within said first sensor channel, extending from a face at said forward assembly to a sensor output at said proximal region, said forward assembly comprising a gaseous ammonia sensitive dye and a membrane encompassing said dye, permeable to gaseous ammonia mounted over said fiberoptic face;

(b) providing a controller actuable to control said ammoniacal component sensor assembly to derive said ammoniacal sensor outputs over a sequence of measurement intervals, and responsive to said ammoniacal sensor outputs to derive a sequence of total ammoniacal concentration values over a measurement period and deriving display signals corresponding with said sequence of values;

(c) providing a display assembly responsive to said display signals to derive a visibly perceptible information output corresponding therewith;

(d) positioning said catheter assembly measurement region within said bloodstream at one of said peripheral regions; and (e) actuating said controller to derive said display signals and effect derivation of said perceptible information output.

163. The method of claim 162 in which said step (a) provides said forward assembly dye as being incorporated within said membrane.

164. The method for monitoring the ammoniacal concentration in blood within the vascular system contained bloodstream of the body, such system directing blood exhibiting a given pH value along given path directions and extending to peripheral regions of such body without the immediate region of the heart, comprising the steps of:

(a) providing a catheter assembly having a proximal end region, a measurement region spaced therefrom extending to a tip, having a first sensor channel extending from said proximal region to said measurement region, an ammoniacal component sensor supported by said first sensor channel, having an ammoniacal component responsive forward assembly at said measurement region contactable with flowing blood within said bloodstream, said sensor assembly being controllable to provide ammoniacal sensor outputs at said proximal end region, said catheter assembly having a second sensor channel extending from said proximal region to said measurement region, having a pH sensor including a pH responsive forward assembly and a fiberoptic transmission component extending therefrom to said proximal region, said pH sensor assembly being controllable to provide a pH output at said proximal region, said ammoniacal component sensor is provided as an ammonia ($NH_3$) sensor and said ammoniacal sensor outputs are provided in correspondence with the concentration of ammonia gas in said bloodstream;

(b) providing a controller actuable to control said ammoniacal component sensor and said pH sensor to derive said ammoniacal sensor outputs over a sequence of measurement intervals, and responsive to said ammoniacal sensor outputs and to said pH output to derive a sequence of total ammoniacal concentration values over a measurement period and deriving display signals corresponding with said sequence of values;

(c) providing a display assembly responsive to said display signals to derive a visibly perceptible information output corresponding therewith;

(d) positioning said catheter assembly measurement region within said bloodstream at one of said peripheral regions; and (e) actuating said controller to derive said display signals and effect derivation of said perceptible information output.

* * * * *